US010736923B2

(12) United States Patent
Keller et al.

(10) Patent No.: US 10,736,923 B2
(45) Date of Patent: Aug. 11, 2020

(54) METHODS AND COMPOSITIONS FOR GENERATING CHONDROCYTE LINEAGE CELLS AND/OR CARTILAGE LIKE TISSUE

(71) Applicant: UNIVERSITY HEALTH NETWORK, Toronto, Ontario (CA)

(72) Inventors: Gordon Keller, Toronto (CA); April M. Craft, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 16 days.

(21) Appl. No.: 15/977,536

(22) Filed: May 11, 2018

(65) Prior Publication Data
US 2019/0111086 A1 Apr. 18, 2019

Related U.S. Application Data

(63) Continuation of application No. 14/782,070, filed as application No. PCT/CA2014/000312 on Apr. 2, 2014, now Pat. No. 9,993,504.

(60) Provisional application No. 61/809,050, filed on Apr. 5, 2013.

(51) Int. Cl.
*C12N 5/077* (2010.01)
*G01N 33/50* (2006.01)
*A61K 35/32* (2015.01)

(52) U.S. Cl.
CPC ............ *A61K 35/32* (2013.01); *C12N 5/0655* (2013.01); *G01N 33/5044* (2013.01); *C12N 2501/115* (2013.01); *C12N 2501/155* (2013.01); *C12N 2501/16* (2013.01); *C12N 2501/415* (2013.01); *C12N 2501/999* (2013.01); *C12N 2503/02* (2013.01); *C12N 2506/02* (2013.01); *C12N 2506/03* (2013.01)

(58) Field of Classification Search
None
See application file for complete search history.

(56) References Cited

U.S. PATENT DOCUMENTS

2011/0229440 A1\* 9/2011 Dealy .................. C12N 5/0655
424/93.7
2013/0052729 A1 2/2013 Pourquie et al.

FOREIGN PATENT DOCUMENTS

| WO | 2010/008100 A1 | 1/2010 |
| WO | 2010/122378 A1 | 10/2010 |
| WO | 2012/013969 A1 | 2/2012 |
| WO | 2013/030243 A1 | 3/2013 |

OTHER PUBLICATIONS

Nakayama et al, J Cell Science, 2003, vol. 116, pp. 2015-2028. (Year: 2003).*
Poliard et al, J Cell Biology, 1995, vol. 103, No. 6, pp. 1461-1472. (Year: 1995).*
Tsang et al, Development, Growth & Differentiation, 2015, vol. 57, pp. 179-192. (Year: 2015).*
International Search Report of International Application No. PCT/CA2014/000312, dated Jul. 10, 2014.
Craft et al., "Specification of chondrocytes and cartilage tissues from embryonic stem cells," Development, Jun. 2013, vol. 140, Issue 12, pp. 2597-2610.
Oldershaw, R.A., "Cell sources for regeneration of articular cartilage: the past, the horizon and the future," International J. of Experimental Pathology, Dec. 2012, vol. 93, pp. 389-400.
Rada et al., "Distinct stem cells subpopulations isolated from human adipose tissue exhibit different chondrogenic and osteogenic differentiation potential," Stem Cell Reviews, Apr. 16, 2010, vol. 7, pp. 64-76.
Tanaka et al., "BMP inhibition stimulates WNT-dependent generation of chondrogenic mesoderm from embryonic stem cells," Stem Cell Research, Sep. 2009, vol. 3, pp. 126-141.
(Continued)

*Primary Examiner* — Allison M Fox
(74) *Attorney, Agent, or Firm* — J.A. Lindeman & Co., PLLC

(57) ABSTRACT

A method for generating chondrocytes and/or cartilage, optionally articular like non-hypertrophic chondrocyte cells and/or cartilage like tissue and/or hypertrophic chondrocyte like cells and/or cartilage like tissue, the method comprising:
a. culturing a primitive streak-like mesoderm population, optionally a CD56+, PDGFRalpha+ KDR– primitive streak-like mesoderm population, with a paraxial mesoderm specifying cocktail comprising:
  i. a FGF agonist;
  ii. a BMP inhibitor; optionally Noggin, LDN-193189, Dorsomorphin; and
  iii. optionally one or more of a TGFbeta inhibitor, optionally SB431524; and a Wnt inhibitor, optionally DKK1, IWP2, or XAV939;
to specify a paraxial mesoderm population expressing cell surface CD73, CD105 and/or PDGFR-beta;
b. generating a chondrocyte precursor population comprising:
  i. culturing the paraxial mesoderm population expressing CD73, CD105 and/or PDGFR-beta at a high cell density optionally in serum free or serum containing media;
  ii. culturing the high cell density CD73+, CD105+ and/or PDGFRbeta+ paraxial mesoderm population with a TGFbeta3 agonist in serum free media to produce a high cell density Sox9+, collagen 2+ chondrocyte precursor population; and
c. either
  i. culturing the high cell density Sox9+, collagen 2+ chondrocyte precursor population with the TGFbeta3 agonist for an extended period of time to produce an articular like non-hypertrophic chondrocyte cells and/or cartilage like tissue; or
  ii. culturing the high cell density Sox9+ collagen2+ chondrocyte precursor population with a BMP4 agonist for an extended period of time to produce a hypertrophic chondrocyte like cells and/or cartilage like tissue.

19 Claims, 19 Drawing Sheets

(56) References Cited

OTHER PUBLICATIONS

Umeda et al., "Human chondrogenic paraxial mesoderm, directed specification and prospective isolation from pluripotent stem cells," Scientific Reports, Jun. 13, 2012, vol. 2:455, pp. 1-11.
Extended Search Report in corresponding International Application No. EP 14778943, dated Jul. 8, 2016.
English Translation of WO 2010008100.

* cited by examiner

A

B

T4 Profiles

C Day 4 primitive streak for hESCs

D Day 3 primitive streak for hiPSCs

E Without CHIR99061

A

B

C

D

D

E

F

B after 10 days in micromass (5x)

C after 2 weeks in micromass (10x)

D micromasses after 5 weeks

A

B

C

3 week micromass 5 week micromass

F      hiPSC derived cartilage tissues
Stained with Toluidine blue

G      hESC derived cartilage tissues
Stained with COL2 and lubricin

H

A  primary adult chondrocytes

B primary fetal chondrocytes

C primary fetal chondrocytes in micromass after 10 weeks

D passage 2 fetal chondrocytes in micromass after 9 weeks

E hPSC-derived chondrocytes in micromass after 11 weeks

F monolayer culture transition to micromass culture

G TGFB3-treated micromass culture

METHODS AND COMPOSITIONS FOR GENERATING CHONDROCYTE LINEAGE CELLS AND/OR CARTILAGE LIKE TISSUE

This application is a Continuation Application of U.S. patent application Ser. No. 14/782,070, filed Oct. 2, 2015; which claims priority to PCT International Application No. PCT/CA2014/000312, filed Apr. 2, 2014; which claims the benefit of Provisional Patent Application No. 61/809,050, filed Apr. 5, 2013 which is incorporated herein by reference in its entirety.

FIELD

The disclosure relates to methods for producing chondrocytes and cartilage and particularly articular chondrocytes and articular cartilage like tissue as well as hypertrophic chondrocytes and growth plate cartilage resembling tissue from human pluripotent stem cells.

BACKGROUND

The ability to efficiently and reproducibly generate differentiated cell types from pluripotent stem cells in vitro has opened the door for the development of cell-based therapies for the treatment of a broad range of degenerative and debilitating diseases. Osteoarthritis (OA) is a candidate for such therapy as it affects at least one in ten adults (Lawrence, Felson et al. 2008), leaving patients with a poor quality of life due to pain associated with joint movement. Pathogenic hallmarks of OA include the degradation of the extracellular matrix (ECM) of articular cartilage that lines the joints together with thickening of the underlying subchondral bone and the formation of osteophytes (bone spurs). Articular cartilage is generated by a distinct subpopulation of chondrocytes known as articular chondrocytes (ACs) that are specified early in development and persist throughout adult life. While ACs function to maintain integrity of the articular cartilage under normal circumstances, they display little capacity to repair cartilage damaged by injury or disease. Consequently, with disease progression, damage to the cartilage is so extensive that surgical intervention such as joint replacement is often required to improve the quality of life for the patient. ACs differ from growth plate chondrocytes (GPCs), whose primary function is to form bone through the process of endochondral ossification (Colnot, 2005). Interestingly, with the onset of OA, ACs appear to acquire some characteristics of GPCs, including hypertrophy, which may contribute to the pathogenesis of this disease.

Chondrocyte and cartilage replacement represent a potential new therapy for OA that could, at some point dramatically reduce the need for mechanical devices. This type of therapy, however, is dependent on access to appropriate tissue and sufficient numbers of highly enriched ACs. It is well established that adult mesenchymal stem cells (MSCs) are able to differentiate to chondrocytes in vitro, however, it is unclear if they are able to give rise to ACs as the cartilage-like tissue generated from them prematurely undergoes hypertrophy (Pelttari, Winter et al. 2006, Steinert, Ghivizzani et al. 2007, Pelttari, Steck et al. 2008) Alternatively, ACs have been harvested directly from patients and used for tissue generation ex vivo, despite their limited capacity to proliferate. Tissue generated by passaged chondrocytes exhibits fibrocartilage characteristics, which can improve the quality of life for the patient in the short term but ultimately undergoes degradation as it lacks sufficient weight bearing capacity (Tins, McCall et al. 2005, LaPrade, Bursch et al. 2008). Pluripotent stem cells (PSCs) such as embryonic and induced pluripotent stem cells (ESCs, iPSCs) may represent a novel and potentially unlimited source of chondrocytes and tissues for therapeutic applications as these cells are able to generate a broad spectrum of cell types under appropriate conditions in vitro.

Chondrocytes develop from paraxial mesoderm that is induced in the early embryo in an ordered temporal pattern following the generation of lateral plate mesoderm (LPM) fated to give rise to hematopoietic and cardiovascular lineages (Lawson, Meneses et al. 1991, Kinder, Tsang et al. 1999). Following induction, strips of paraxial mesoderm are segmented into somites (Tam and Tan 1992, Kulesa and Fraser 2002). Somite development is regulated, in part, by the transcription factors paraxis (TCF15) and TBX18, whose expression coincides with induction of paraxial mesoderm (Burgess, Rawls et al. 1996, Bussen, Petry et al. 2004, Singh, Petry et al. 2005). Individual somites are then patterned into the ventral sclerotome, which forms the axial skeleton, including cartilage and the vertebral column, and the dorsal dermomyotome which develops into skeletal muscles and the dermis of the back (Hirsinger, Jouve et al. 2000). Specification of the sclerotome is marked by the expression of two transcription factors, Meox1 (Mankoo, Skuntz et al. 2003) and Nkx3.2 (Bapx1). A population of collagen 2 (Col2a1) positive mesenchymal cells with chondrogenic potential develops from sclerotome-derived cells at E12.5 of mouse development (Akiyama, Chaboissier et al. 2002, Dao, Jonason et al. 2012).

While methods for differentiating progenitor cells to the chondrogenic lineage are established, the ability to specify ACs, and ultimately stable cartilage tissue containing non-hypertrophic chondrocytes, remains poorly understood. ACs are derived from interzone cells, a fibrotic population of cells that forms at future sites of synovial joints, marked by the upregulation of Wnt9a/14 and growth and differentiation factor 5 (GDF5/BMP14), a member of the TGFβ superfamily (Archer, Dowthwaite et al. 2003, Pacifici, Koyama et al. 2006). Lineage tracing studies have shown that GDF5-expressing interzone cells give rise to several joint tissues including ACs, but do not contribute to the GPC population (Koyama, Shibukawa et al. 2008). GPCs, by contrast, develop from the condensing chondrogenic mesenchyme and express BMP 2, 4 and 7, as well as hypertrophy related genes including collagen 10. Distinct regions of ACs and GPCs are observed as early as postnatal day 7-8 when the secondary ossification center begins to form (Murakami, Balmes et al. 2004, Blumer, Longato et al. 2007). These observations suggest that ACs and GPCs are generated from separate progenitor populations during development and as such, may represent distinct lineages.

A number of studies have demonstrated that it is possible to derive chondrocytes from mouse (m) and human ESCs and iPSCs in vitro. Most, however, used serum-based media to support the early stages of differentiation resulting in the generation of mixed lineage end stage cultures (Kramer, Hegert et al. 2000, zur Nieden, Kempka et al. 2005, Hwang, Kim et al. 2006, Hwang, Varghese et al. 2008, Jukes, Both et al. 2008, Yamashita, Krawetz et al. 2008). Recent studies have reported the use of defined culture media with specific pathway agonists and antagonists to direct differentiation (Nakayama, Duryea et al. 2003, Darabi, Gehlbach et al. 2008, Tanaka, Jokubaitis et al. 2009). In mESCs, Tanaka et al (2009) showed that the combination of Wnt signaling with BMP inhibition resulted in the generation of paraxial mesoderm with chondrogenic potential, identified by the expression of PDGFRalpha and a lack of expression of Flk-1. This mesoderm also displayed some cardiac potential but showed no capacity to generate hematopoietic cells indicating that dependency on BMP signaling distinguishes different types of mesoderm.

Oldershaw et al. (Oldershaw, Baxter et al. 2010) used a serum free protocol. No tissues were obtained in vitro or in vivo with the method of Oldershaw.

Umeda et al (Umeda, Zhao et al. 2012) used a method using PDGF stimulation that produced nodules comprising Runx2 expressing cells.

Osteoarthritis is a degenerative disease that mainly affects the joint-lining articular cartilage of the joint. Articular cartilage has very limited capacity to regenerate itself upon injury, thus cell and tissue replacement strategies are the only means of replacing this tissue effectively. Methods of producing human cartilage from pluripotent stem cells are currently lacking, despite great need for such tissues for drug discovery and cartilage replacement strategies in patients with joint diseases such as osteoarthritis.

SUMMARY

An aspect of the application provides a method for generating chondrocyte lineage cells and/or cartilage like tissue, optionally articular like non-hypertrophic chondrocyte cells and/or cartilage like tissue and/or hypertrophic chondrocyte like cells and/or cartilage like tissue, the method comprising:
(a) culturing a primitive streak-like mesoderm cell population (e.g. stage 2), optionally a CD56+, PDGFRalpha+ primitive streak-like mesoderm cell population, with a paraxial mesoderm specifying cocktail comprising:
   (i) a FGF agonist;
   (ii) a BMP inhibitor, optionally Noggin, LDN-193189, and/or Dorsomorphin; and
   (iii) optionally one or more of a TGFbeta inhibitor, optionally SB431542; and a Wnt inhibitor, optionally IWP2 (N-(6-Methyl-2-benzothiazolyl)-2-[(3,4,6,7-tetrahydro-4-oxo-3-phenylthieno[3,2-d]pyrimidin-2-yl)thio]-acetamide; Sigma); Dickkopf-related protein 1 (DKK1; R & D Systems), and/or XAV939 (3,5,7,8-Tetrahydro-2-[4-(trifluoromethyl)phenyl]-4H-thiopyrano[4,3-d]pyrimidin-4-one; Sigma);
   to specify a paraxial mesoderm cell population expressing cell surface CD73, CD105 and/or PDGFR-beta;
(b) generating a chondrocyte precursor population from the paraxial mesoderm cell population expressing cell surface CD73, CD105 and/or PDGFR-beta, the generating the chondrocyte precursor population comprising:
   (i) culturing the paraxial mesoderm cell population expressing cell surface CD73, CD105 and/or PDGFR-beta at a high cell density in serum free or serum containing media;
   (ii) culturing the high cell density CD73+, CD105+ and/or PDGFRbeta+ paraxial mesoderm cell population with a TGFbeta agonist, optionally TGFB1, TGFB2 and/or TGFB3 in serum free media to produce a high cell density Sox9+, collagen 2+ chondrocyte precursor population (e.g. Stage 3); and
(c) either:
   (i) culturing the high cell density Sox9+, collagen 2+ chondrocyte precursor population with a TGFbeta agonist (optionally TGFBeta1, TGFbeta2 and/or TGFBeta3) for an extended period of time to produce articular like non-hypertrophic chondrocyte like cells and/or cartilage like tissue; or
   (ii) culturing the high cell density Sox9+ collagen2+ chondrocyte precursor population with a BMP4 agonist for an extended period of time to produce hypertrophic chondrocyte like cells and/or cartilage like tissue (e.g. stage 4).

Another aspect includes a method for generating chondrocyte like cells and/or cartilage like tissue, optionally articular like non-hypertrophic chondrocyte like cells and/or cartilage like tissue and/or hypertrophic chondrocyte like cells and/or cartilage like tissue, the method comprising:
(a) culturing a starting population of pluripotent stem cells with a primitive streak inducing cocktail to induce a primitive streak-like mesoderm cell population expressing CD56 and/or PDGFR-alpha (e.g. stage 1);
(b) culturing the primitive streak-like mesoderm cell population expressing CD56 and PDGFR-alpha with a paraxial mesoderm specifying cocktail comprising:
   (i) a FGF agonist;
   (ii) a BMP inhibitor, optionally Noggin, LDN-193189, and/or Dorsomorphin; and
   (iii) one or more of a TGFbeta inhibitor, optionally SB431524; and a Wnt inhibitor, optionally DKK1, IWP2 and/or XAV939;
   to specify a paraxial mesoderm cell population expressing cell surface CD73, CD105 and PDGFR-beta;
(c) generating a chondrocyte precursor population from the paraxial mesoderm cell population expressing cell surface CD73, CD105 and/or PDGFR-beta, the generating the chondrocyte precursor population comprising:
   (i) culturing the paraxial mesoderm cell population expressing CD73, CD105 and/or PDGFR-beta at a high cell density in serum free or serum containing media;
   (ii) culturing the high cell density CD73+, CD105+ and PDGFRbeta+ paraxial mesoderm cell population with a TGFbeta agonist in serum free media to produce a high cell density Sox9+, collagen 2+ chondrocyte precursor population; and
(d) either
   (i) culturing the high cell density Sox9+, collagen 2+ chondrocyte precursor population with a TGFbeta agonist for an extended period of time to produce articular like non-hypertrophic chondrocyte like cells and/or cartilage like tissue; or
   (ii) culturing the high cell density Sox9+ collagen2+ chondrocyte precursor population with a BMP4 agonist for an extended period of time to produce hypertrophic chondrocyte like cells and/or cartilage like tissue.

In an embodiment, the method is for generating articular like non-hypertrophic chondrocyte like cells and/or cartilage like tissue. In another embodiment, the method is for generating hypertrophic chondrocyte like cells and/or cartilage like tissue.

In an embodiment, the extended period of time the high cell density Sox9+ collagen2+ chondrocyte precursor population is cultured with the TGF beta agonist is at least 3 weeks, at least 4 weeks, at least 5 weeks, at least 6 weeks, at least 7 weeks, at least 8 weeks, at least 9 weeks, at least 10 weeks, at least 11 weeks, at least 12 weeks or more to generate a non-hypertrophic chondrocyte like and/or cartilage like tissue that expresses for example lubricin and CILP2.

In an embodiment, the extended period of time the high cell density Sox9+ collagen2+ chondrocyte precursor population is cultured with the BMP4 agonist is at least 3 weeks, at least 4 weeks, at least 5 weeks, at least 6 weeks, at least 7 weeks, at least 8 weeks, at least 9 weeks, at least 10 weeks, at least 11 weeks, at least 12 weeks or more to generate a cartilage like tissue that expresses collagen 2 or hypertrophic chondrocyte cells that express collagen 10.

A method of generating chondrocyte like cells comprising:
  (a) culturing chondrocyte precursor cells at a high cell density in serum free or serum containing media;
  (b) culturing the high cell density chondrocyte precursor cells with a TGFbeta agonist in serum free media; and
  (c) either
    (i) culturing the chondrocyte precursor cells with a TGFbeta agonist for an extended period of time to produce articular cartilage like chondrocyte cells; or
    (ii) culturing the chondrocyte precursor cells with a BMP4 agonist for an extended period of time to produce hypertrophic chondrocyte lineage cells and/or cartilage like tissue.

In an embodiment, the chondrocyte precursor cells are primary fetal chondrocytes or passaged fetal chondrocytes.

In an embodiment, the generated cells and/or tissues are administered to a subject.

Also provided in another embodiment is an isolated population of articular like non-hypertrophic chondrocyte like cells and/or cartilage like tissue and/or hypertrophic chondrocyte like cells and/or cartilage like tissue generated according to a method described herein.

A further aspect includes composition comprising the population of articular like non-hypertrophic chondrocyte like cells and/or cartilage like tissue and/or hypertrophic chondrocyte like cells and/or cartilage like tissue, and a carrier optionally PEG, hydrogel, bone scaffolding, bone substitute scaffolding and/or matrigel. In an embodiment, the carrier is pharmaceutical grade.

In an embodiment, the isolated population is comprised in a composition comprising a diluent or carrier, optionally a pharmaceutical diluent. In an embodiment, the diluent is culture media, optionally comprising a cryopreservation agent such as glycerol and/or DMSO, serum and albumin, such as human serum albumin.

A further aspect includes a cartilage and/or bone tissue product comprising the cells or composition described herein, and a scaffold.

Another aspect includes method for ameliorating symptoms and/or treating a subject in need thereof comprising administering cells and/or tissue generated using a method described herein and/or transplanting a cartilage and/or bone tissue product described herein.

Also provided in another aspect is use of cells and/or tissue generated using a method described herein and/or a cartilage and/or bone tissue product comprising said cells and/or tissue for ameliorating symptoms and/or treating a subject in need thereof.

A further aspect includes a method of generating a paraxial mesoderm cell population comprising:
  (a) culturing a starting population of pluripotent stem cells with a primitive streak inducing cocktail to induce a primitive streak-like mesoderm cell population expressing CD56 and PDGFR-alpha (e.g. stage 0);
  (b) culturing a primitive streak-like mesoderm cell population expressing CD56 and PDGFR-alpha with a paraxial mesoderm specifying cocktail comprising:
    (i) a FGF agonist; and
    (ii) a BMP inhibitor, optionally Noggin, LDN-193189, Dorsomorphin; and
    (iii) one or more of a TGFbeta inhibitor, optionally SB431524; and a Wnt inhibitor, optionally DKK1, IWP2, and/or XAV939;
to specify a paraxial mesoderm cell population expressing cell surface CD73, CD105 and PDGFR-beta.

Methods of isolating cells and screening assays are also provided.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

1. Definitions

The term "primitive streak-like mesoderm cell population" as used herein means a population of mesoderm cells expressing Brachyury and the cell surface markers CD56 and PDGFRalpha. For example, the primitive streak-like mesoderm cell population can comprise at least 50%, at least 60%, at least 70%, at least 80% or about 90% cells expressing CD56 and PDGFRalpha Cartilage differentiation has been obtained with the disclosed methods using for example 50% CD56/PDGFRalpha+ cells.

Figure 2:
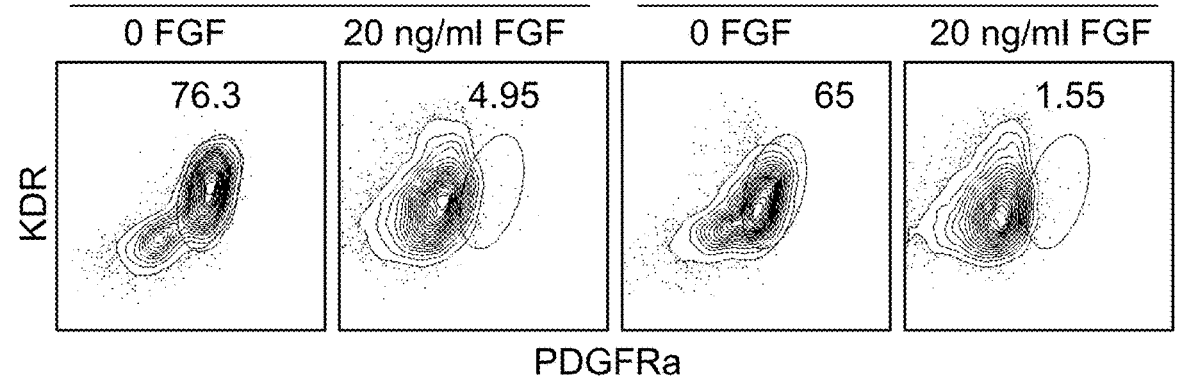
FIG. 2. Characterization of paraxial mesoderm derived from hPSCs. Flow cytometric analysis of day 5 mesoderm treated with no additional factors (0 DM, no FGF), FGF, 4 µM DM, or 4 µM DM+FGF. Day 5 profiles depict KDR and PDGFRa expression, a double-positive population (gated) indicates mesoderm that has cardiac potential (20). Treatment with FGF results in less PDGFRa expression on day 5. (B) Expression of cell surface markers CD73, CD105, and PDGFR-beta on mesoderm populations on day 15 of differentiation. (C) Wnt inhibition can also improve the efficiency of CD73 and CD105 expression. Experimental cell treatments during day 4 to day 6 include the combination of Dorsomorphin, bFGF, TGFbeta inhibitor (SB431542) in the presence or absence of the wnt pathway inhibitor IWP2. Flow cytometric analyses of CD73 and CD105, on day 15 mesoderm populations derived as indicated. (D) Gene expression analyses of day 15 mesoderm populations derived in indicated factors. Nkx2.5 is a cardiac transcription factor, Meox1 and Nkx3.2 are paraxial mesoderm and somite transcription factors. (E) Micrographs depicting 1 day old micromasses and 1 week old micromasses derived from day 15 mesoderm populations as indicated. (F) Flow cytometric analysis of cardiac troponin T (cTnT) expression in 1 week old micromasses derived from day 15 mesoderms as indicated. (G) 4 week old micromasses derived from DM+FGF-treated paraxial mesoderm generates cartilage tissues, but mesoderm specified with FGF alone do not generate cartilage-like tissues (see non-adherent aggregates).
Figure 2:
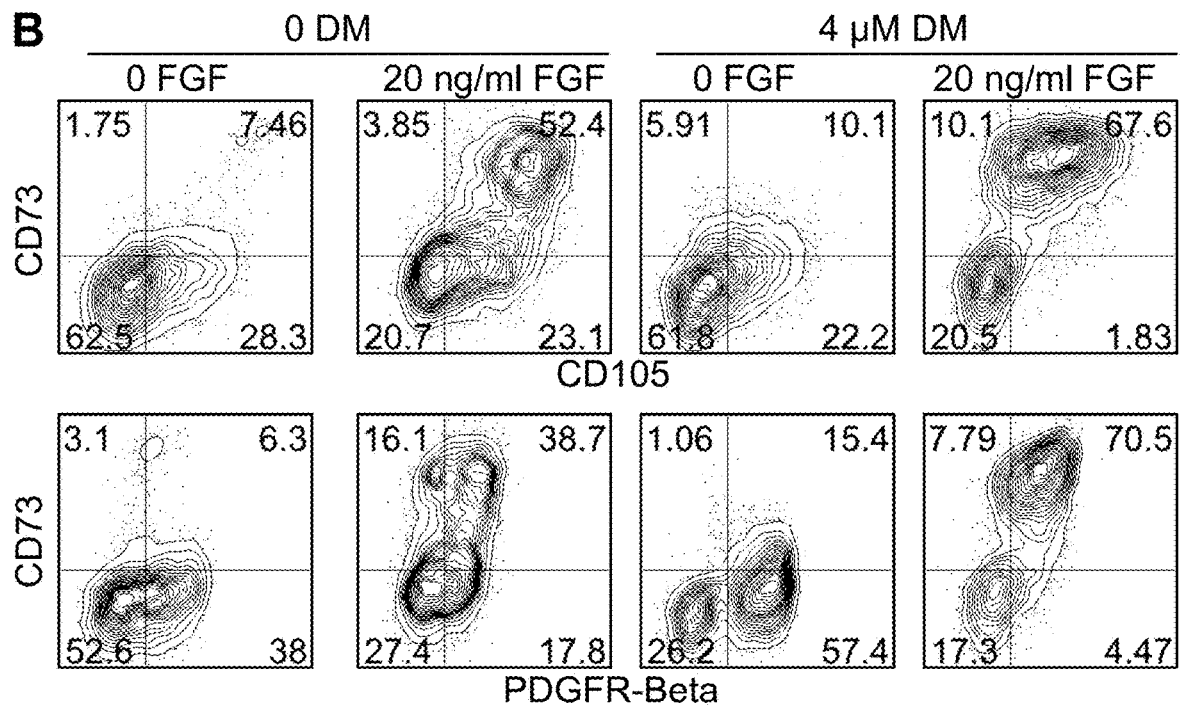
Figure 2:
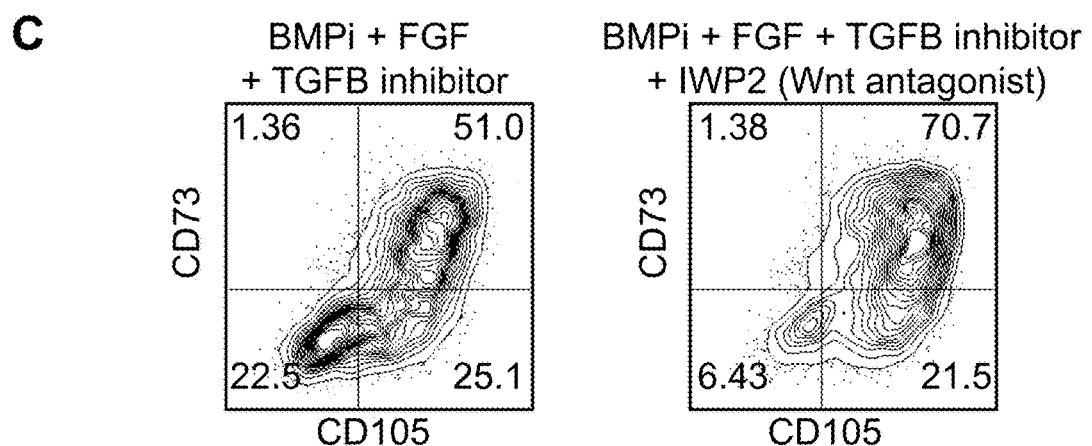
Figure 2:
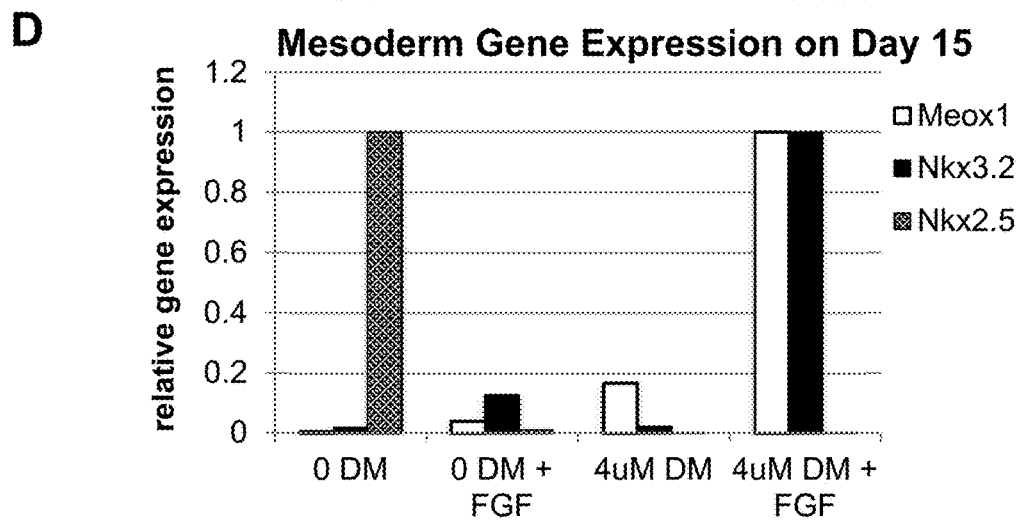
Figure 2:
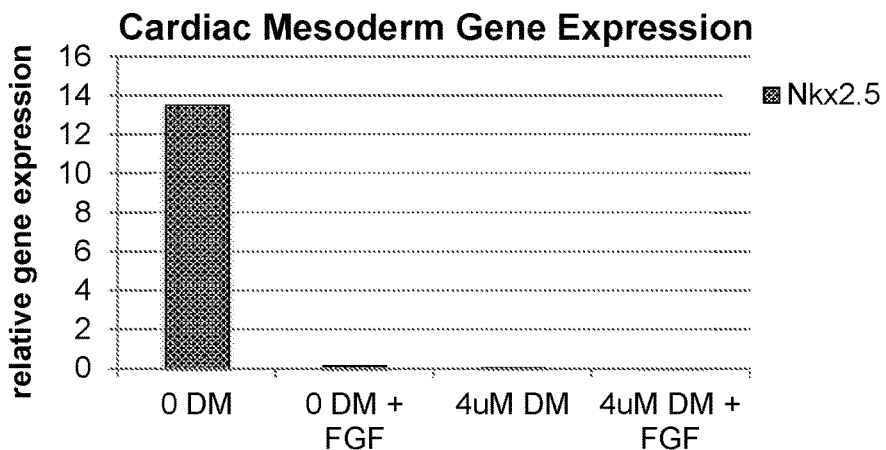
Figure 2:
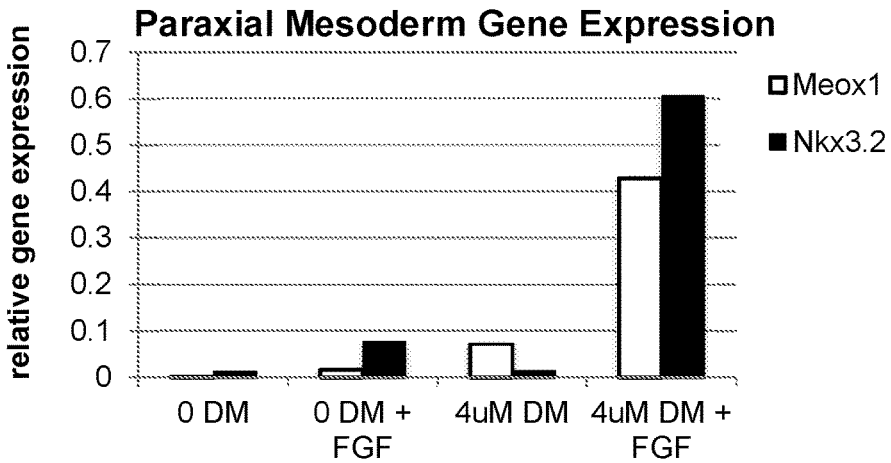
Figure 2:
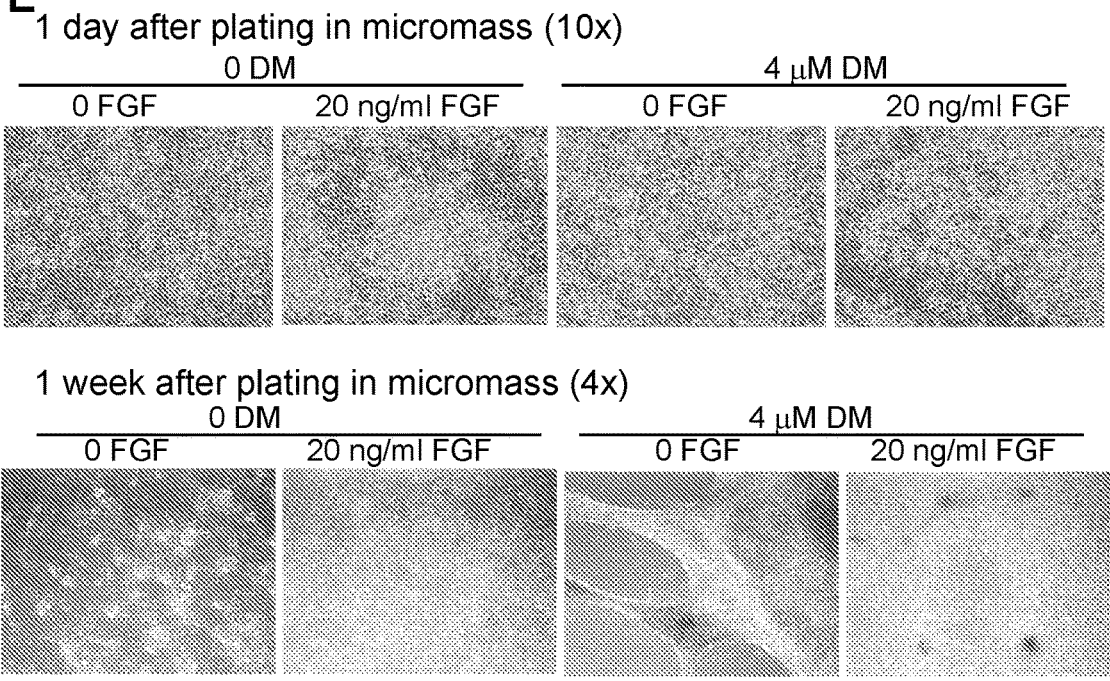
Figure 2:
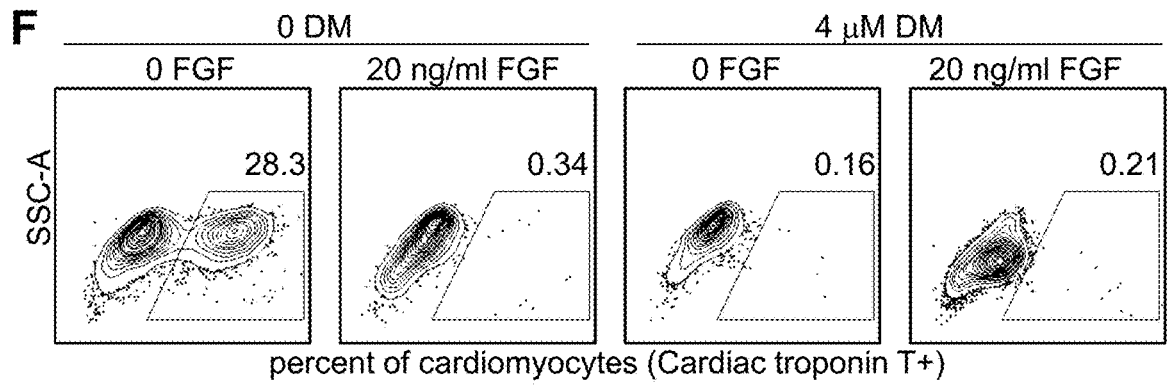

The term "paraxial mesoderm cell population expressing cell surface CD73, CD105 and/or PDGFR-beta" as used herein means mesoderm cells expressing CD73, CD105 and/or PDGFR-beta and the paraxial mesoderm transcription factor Meox1. For example, the paraxial mesoderm cell population comprises at least 70% cells expressing Meox1, CD73, CD105 and/or PDGFR-beta As shown in FIG. 2D. Meox1 expression is increased in FGF and Dorsomorphin treated cells compared to non FGF and Dorsomorphin treated cells.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining such as FACS.

The term "expressing" also represented as "+" as used herein means, with respect to a cell protein level, detectable protein expression compared to a cell that is not expressing the protein, for example as measured by FACS analysis. Using FACS analysis, a cell is considered positively expressing the protein on the cell surface if the mean fluorescence of the signal is brighter than a cell that was not stained with the antibody (unstained control) or cells that were stained with the antibody but do not express the protein on the cell surface. With respect to a cell population, "expressing" as used herein means at least 50% of the cells in the cell population express the marker. In an embodiment, the cells expressing for example cells expressing CD73 or the other markers are sorted such that for example 70%, 80, 90% or more of the cells are positive and express the marker.

The term "lacking expression" also represented as "−" as used herein means with respect to a cell protein level, undetectable protein expression compared to a cell that is expressing the protein, for example as measured by FACS analysis. With respect to a cell population, "lacking expression" as used herein means less than 25%, less than 20%, less than 15%, less than 10%, less than 5% or less than 1% of the cells in the cell population express the marker.

The term "culturing" as used herein incubating and/or passaging cells in an adherent, suspension or 3D culture. As used herein, the term "adherent culture" refers to a cell culture system whereby cells are cultured on a solid surface, which may in turn be coated with an insoluble substrate that may in turn be coated with another surface coat of a substrate, such as those listed below, or any other chemical or biological material that allows the cells to proliferate or be stabilized in culture. The cells may or may not tightly adhere to the solid surface or to the substrate. The substrate for the adherent culture may comprise any one or combination of tissue culture treated plastic, polyornithine, laminin, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). In one embodiment, the cells are plated on MATRIGEL®-coated plates. In another embodiment, the cells are plated on fibronectin-coated plates. Cells can be cultured in filter cultures and micromass cultures. In an embodiment, cells are plated onto membrane filters, optionally those that are placed into tissue cultures dishes as part of a transwell system (Millipore, alvatex are two brands). The substrate could also be a bone scaffold substitute such as CPP (calcium polyphosphate) or other pharmaceutically available scaffolds available. Micromass culture is comprised of a high density suspension of cells is permitted to adhere to a small area of the substrate (e.g. 200,000-500,000 cells adhere to a 0.2-1 cm diameter circular area of the substrate). Any shape or size of substrate can be used, prepared for example by 3D printing. The term "suspension" as used in the context of cell culturing is used as it is in the art. Namely, cell culture suspensions are cell culture environments where the cells do not adhere to a surface. One of skill in the art will be familiar with suspension culture techniques, including, but not limited to, the use of equipment such as flow hoods, incubators and/or equipment used to keep the cells in constant motion, e.g., rotator platforms, shakers, etc, if necessary.

The term "contacting" or "culturing . . . with" is intended to include incubating the component(s) and the cell/tissue together in vitro (e.g., adding the compound to cells in culture) and the step of "contacting" or "culturing . . . with" can be conducted in any suitable manner. For example the cells may be treated in adherent culture, or in suspension culture, or in 3D culture; the components can be added temporally substantially simultaneously (e.g. together in a cocktail) or sequentially (e.g. within 1 hour, 1 day or more from an addition of a first component). The cells can also be contacted with another agent such as a growth factor or other differentiation agent or environments to stabilize the cells, or to differentiate the cells further and include culturing the cells under conditions known in the art. Stage 1 for example is typically practiced in suspension culture. Stag 2 is in an embodiment carried out in suspension. Stage 3 and/or 4 can for example be carried out in suspension culture for example if the cells are aggregated in a pellet format instead of a micromass or filter format. Pellet cultures are a cluster of cells at high density that can float in suspension in a tube. In an embodiment, part of a stage is carried out in suspension or mixed suspension and adherent, optionally 3D culture. For example, some tissues become non-adherent over time and are thus in suspension for some of the culture period of stage 4.

The term "high cell density" as used herein means about 200,000 cells-about 1,000,000 cells per about 0.2 cm-about 2 cm diameter surface area (2D), or with respect to micromass is at least about 100,000 cells per about 20 microliters of media, or for example up to about 2,000,000 cells per about 20 microliters of media to allow for cells to adhere to the small surface area permitted for a micromass 'spot'. For membrane filters, the area is dependent on the commerically available membrane that is purchased, for example approximately 400,000 cells-about 2,000,000 cells can be plated in about 200 microliters-about 500 microliters of media in for example a about 1 cm-about 2 cm cylinder shaped membrane filter-containing insert to allow cells to adhere. In both mircomass and membrane filter culture, cells adhere in about a 1-5 cell layer and tissue is permitted to grow 'thicker' after adherence. A similar cell density could be used to seed onto a bone substitute scaffold such as the CPP.

As used herein, "serum free" refers to the absence of serum in the solutions e.g. medias used to culture the given cell population. For example, serum free medium or environment can contain less than 4, 3, 2, or 1% serum. In a preferred embodiment, the serum free composition does not contain serum, or only contains trace amounts of serum from the isolation of components that are added to the defined media (e.g. contains 0% added serum).

The term "BMP inhibitor" as used herein means any inhibitor of BMP signaling and includes for example a type 1 BMP receptor inhibitor, BMP ligands and/or soluble BMP receptors, optionally selected from dorsomorphin (DM), noggin, Chordin, LDN-193189, soluble BMPR1a, and/or soluble BMPR1b.

The term "FGF agonist" as used herein means a molecule such as a cytokine, including for example FGF, or a small molecule, that activates a FGF signalling pathway, e.g binds and activates a FGF receptor.

The term "FGF" as used herein refers to any fibroblast growth factor, and optionally bFGF, FGF2, FGF4, FGF9 and/or optionally FGF 19, 21, 3, 5, 6, 8a, 16-18, 20 and/or 23, for example human FGF1 (Gene ID: 2246), FGF2 (also known as bFGF; Gene ID: 2247), FGF3 (Gene ID: 2248), FGF4 (Gene ID: 2249), FGF5 (Gene ID: 2250), FGF6 (Gene ID: 2251), FGF7 (Gene ID: 2252), FGF8 (Gene ID: 2253), FGF9 (Gene ID: 2254) and FGF10 (Gene ID: 2255) optionally including active conjugates and fragments thereof, including naturally occuring active conjugates and fragments. In certain embodiments, FGF is bFGF, FGF2, FGF4, and/or FGF9. As used herein, "active conjugates and fragments of FGF" include conjugates and fragments of a fibroblast growth factor that bind and activate a FGF receptor and optionally activate FGF signalling.

The term "TGFbeta agonist" or TGFb agonist as used herein any molecule that promotes TGFbeta signaling and includes for example TGFb1, TGFb2 and/or TGFb3.

The term "TGFbeta inhibitor" as used herein means any molecule that inhibits receptors ALK4 and ALK7 and/or TGF-βRI, for example SB431542 (Sigma Aldrich) A83-01 (Tocris, 2929), D 4476, GW 788388, LY 364947, RepSox, SB 505124, SB 525334 (Sigma Aldrich), and SD 208.

The term "BMP4 agonist" as used herein means any molecule optionally any BMP or GDF that activates the receptor for BMP4, including for example GDF5, GDF6, GDF7, BMP4, BMP2, BMP6, BMP7 and/or, BMP10.

The term "BMP4" (for example Gene ID: 652) as used herein refers to Bone Morphogenetic Protein 4, for example human BMP4, as well as active conjugates and fragments thereof, optionally including naturally occuring active conjugates and fragments, that can for example activate BMP4 receptor signaling.

The term "nodal agonist" as used herein means any molecule that activates nodal signal transduction such as "nodal" (for example human nodal such as Gene ID: 4338) or "activin" in a hepatocyte lineage cell.

The term "activin" or "ActA" as used herein refers to "Activin A" (for example Gene ID: 3624), for example human activin, as well as active conjugates and fragments thereof, optionally including naturally occuring active conjugates and fragments, that can for example activate nodal signal transduction as well as active conjugates and fragments thereof, including naturally occuring active conjugates and fragments.

The term "a wnt agonist" as used herein means any molecule that activates wnt/beta-catenin receptor signaling in a chondrocyte lineage cell and includes for example Wnt3a and as well as GSK3 selective inhibitors such as CHIR99021 (Stemolecule™ CHIR99021 Stemgent), 6-Bromolndirubin-3'-Oxime (BIO) (Cayman Chemical (cat: 13123)), or Stemolecule™ BIO from Stemgent (cat:04003). CHIR99021 is a selective inhibitor of GSK3. The GSK3 selective inhibitors contemplated are for example selective inhibitors for GSK-3α/β in the Wnt signaling pathway.

The term "Wnt3a" as used herein refers to wingless-type MMTV integration site family, member 3A factor (e.g. Gene ID: 89780), for example human Wnt3a, as well as active conjugates and fragments thereof, including naturally occuring active conjugates and fragments.

The term "Wnt antagonist" or "wnt inhibitor" as used herein means any molecule that inhibits wnt/beta cantenin receptor signaling in a chondrocyte lineage cell, including for example IWP2 (N-(6-Methyl-2-benzothiazolyl)-2-[(3,4, 6,7-tetrahydro-4-oxo-3-phenylthieno[3,2-d]pyrimidin-2-yl) thio]-acetamide; Sigma); Dickkopf-related protein 1 (DKK1; R & D Systems), and/or XAV939 (3,5,7,8-Tetrahydro-2-[4-(trifluoromethyl)phenyl]-4H-thiopyrano[4,3-d] pyrimidin-4-one; Sigma).

The term "agonist" as used herein means an activator, for example, of a pathway or signaling molecule. An agonist of a molecule can retain substantially the same, or a subset, of the biological activities of the molecule (e.g. nodal). For example, a nodal agonist means a molecule that selectively activates nodal signaling.

The term "inhibitor" as used herein means a selective inhibitor, for example of a pathway or signaling molecule. An inhibitor or antagonist of a molecule (e.g. BMP4 inhibitor) can inhibit one or more of the activities of the naturally occurring form of the molecule. For example, a BMP4 inhibitor is a molecule that selectively inhibits BMP4 signaling.

The term "selective inhibitor" as used herein means the inhibitor inhibits the selective entity or pathway at least 1.5×, 2×, 3×, 4× or 10× more efficiently than a related molecule.

The term "specifying" as used herein means a process of committing a cell toward a specific cell fate, prior to which the cell type is not yet determined and any bias the cell has toward a certain fate can be reversed or transformed to another fate. Specification induces a state where the cell's fate cannot be changed under typical conditions. Specification is a first step of differentiation.

The term "stem cell" as used herein, refers to an undifferentiated cell which is capable of proliferation, self-renewal and giving rise to more progenitor or precursor cells having the ability to generate a large number of mother cells that can in turn give rise to differentiated, or differentiable, daughter cells. The daughter cells can for example be induced to proliferate and produce progeny cells that subsequently differentiate into one or more mature cell types, while also retaining one or more cells with parental developmental potential. The term "stem cell" includes embryonic stem cell and pluripotent stem cell.

The term "embryonic stem cell" is used to refer to the pluripotent stem cells of the inner cell mass of the embryonic blastocyst (see, for example, U.S. Pat. Nos. 5,843,780, 6,200,806). Such cells can also be obtained from the inner cell mass of blastocysts derived from somatic cell nuclear transfer (see, for example, U.S. Pat. Nos. 5,945,577, 5,994, 619, 6,235,970).

The term "pluripotent stem cell" as used herein refers to a cell with the capacity, under different conditions, to differentiate to more than one differentiated cell type, and for example the capacity to differentiate to cell types characteristic of the three germ cell layers. Pluripotent cells are characterized by their ability to differentiate to more than one cell type using, for example, a nude mouse teratoma formation assay. Pluripotency is also evidenced by the expression of embryonic stem (ES) cell markers. Pluripotent stem cells include induced pluripotent stem cells (iPSC) and embryonic stem cells. In an embodiment, the pluripotent stem cell is derived from a somatic cell. In an embodiment, the pluripotent stem cell is derived from a human somatic cell.

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing expression of one or more genes including POU4F1/OCT4 (Gene ID; 5460) in combination with, but not restricted to, SOX2 (Gene ID; 6657), KLF4 (Gene ID; 9314), cMYC (Gene ID; 4609), NANOG (Gene ID; 79923), LIN28/LIN28A (Gene ID; 79727)). The expression can be induced for example by forced gene expression or using small molecules, small RNAs, non-integrating gene expression vectors, or proteins.

The term "chondrocyte like cells" as used herein means chondrocyte cells and cells that are cytochemically similar and express chondrocyte markers, including for example Sox9 and Collagen 2, and behave as chondrocyte cells. The chondrocyte cells can be articular cartilage like chondrocytes or precursors or chondrocytes that are capable of hypertrophy (optionally referred to as GPC like cells) or precursors thereof.

The term "cartilage like tissue" as used herein means cartilage tissue and tissue that is histologically similar and expresses cartilage markers, for example collagen 2 and aggrecan, and behaves as cartilage, including articular cartilage tissue and/or growth plate cartilage like tissue.

The term "articular chondrocyte like cells and/or cartilage tissue" as used herein means a population, optionally enriched or mixed, comprising articular chondrocyte cells and/or articular chondrocyte like cells including for example, cartilage like tissue comprising articular chondrocyte like cells.

The term "hypertrophic chondrocyte like cells and/or cartilage tissue" or "GPC like cells and/or cartilage tissue" as used herein means a population, optionally enriched or mixed, comprising hypertrophic chondrocyte cells and/or hypertrophic chondrocyte like cells (e.g. iliac crest chondrocytes) including for example, cartilage like tissue comprising hypertrophic chondrocyte like cells.

The term "articular cartilage like tissue" or "cartilage containing non hypertrophic chondrocyte-like cells" is histologically similar and expresses articular cartilage markers such as lubricin and/or CILP2 and behaves as articular cartilage. For example, articular cartilage is maintained as stable cartilage in vivo.

The term "growth plate cartilage like tissue" as used herein means cartilage tissue that is histologically similar and expresses cartilage markers that are found in growth plate cartilage tissue including collagen X, RUNX2, SP7 and/or alkaline phosphates and behaves like growth plate cartilage For example, growth plate cartilage functions in vivo to provide a scaffold onto which new bone will form.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 65%, preferably at least about 75%, at least about 85%, more preferably at least about 90%, and most preferably at least about 95% pure, with respect to the cells making up a total cell population.

The terms "enriching" or "enriched" are used interchangeably herein and mean that the yield (fraction) of cells of one type is increased by at least about 10%, at least about 20%, at least about 30%, at least about 40%, at least about 50% or at least about 60% over the fraction of cells of that type in the starting culture or preparation. Enriching and partially purifying can be used interchangeably.

The population of cells can be enriched using different methods such as methods based on markers such as cell surface markers (e.g. FACS sorting etc).

The term "subject" as used herein includes all members of the animal kingdom including mammals such as and including a primate such as human, monkey or ape, a dog, cat, cow, horse, goat, pig, rabbit, sheep or a rodent such as a rat, or mouse, and suitably refers to a human.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to a subject.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating joint/bone disorders. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

As used herein, the terms "administering", "implanting" and "transplanting" are used interchangeably in the context of delivering cells tissues and/or products described herein into a subject, by a method or route which results in at least partial localization of the introduced cells at a desired site. The cells can be implanted directly to a joint, or alternatively be administered by any appropriate route which results in delivery to a desired location in the subject where at least a portion of the implanted cells or components of the cells remain viable.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

2. Methods and Products

Described here are methods of producing paraxial/chondrogenic mesoderm cells from human pluripotent stem cells (PSCs); of generating articular cartilage-like tissue in-vitro that expresses the articular cartilage marker lubricin and histologically cannot be distinguished for example from human cartilage tissue of the knee joint; as well as methods of making a cartilage-like tissue with growth plate-like properties, which is the second type of cartilage found in humans, and is the cartilage that is responsible for the growth of long bones due to its propensity to undergo hypertrophy and express collagen 10. Chondrocyte cells prepared using methods described herein are further demonstrated to be stable and maintain their articular cartilage like or growth plate cartilage like properties after transplant. In addition, CD73 cell surface marker was found to be expressed by articular chondrocytes.

It is demonstrated herein that CD73 is expressed by primary adult and fetal healthy chondrocytes as well as hESC-derived articular-like chondrocytes but is not expressed on growth plate-like chondrocytes derived from hESCs.

The methods described use, in an embodiment, serum free methods to generate paraxial/chondrogenic mesoderm (CD73+CD105+PDGFRbeta+), as well as organized cartilage-like tissue that resembles human cartilage for example of the knee. Serum free methods disclosed herein are useful for cell and tissue based engineering strategies and may be used for example for articular cartilage replacement. These cells are also useful for identifying molecules that may be involved in degradation of cartilage in patients with osteoarthritis, drug discovery applications which identify molecules that can permit expansion of these chondrocytes in-vitro for potential application to autologous chondrocyte transplantation surgeries, or drugs that may attenuate osteoarthritis. Further, access to both pluripotent stem cell-derived articular and growth plate-like cartilage tissues will allow for the development of cell and tissue based therapies for treatment of osteoarthritis as well as other joint and bone disorders.

It is demonstrated herein for example that, chondrocyte specification can be accomplished in a high-density culture of the paraxial mesoderm population in serum free media containing TGFb3, TGFb2 or TGFb1 for a brief period (e.g. 10 days). Continued or extended TGFb agonist stimulation generates cartilage tissue with articular cartilage characteristics (histology and gene expression), while stimulation with BMP4 induces a growth plate-like cartilage tissue containing hypertrophic chondrocytes.

Extended culture has been performed, for example for over a 12 week, or longer optionally 14 week period, during which maturation of tissue to lubricin+ or collagen 10+ cartilage tissue was demonstrated.

Using the methods described herein co-culture-with other cells is not required, nor is conditioned media or a scaffold, although these can be used in some embodiments.

CD73 expression, a cell surface marker, is demonstrated to mark healthy primary adult and fetal articular chondrocytes but is not expressed in adult growth plate chondrocytes of the iliac crest. Similar to primary healthy articular chondrocytes, hESC-derived articular-like chondrocytes (TGFB3-treated) express CD73. Conversely, hESC-derived growth plate-like chondrocytes (BMP4-treated) express significantly less CD73. This marker can be used to distinguish these two chondrocyte sub-populations, where CD73 is expressed by both primary and hESC-derived articular chondrocytes but is not expressed (substantially) on growth plate like chondrocytes.

Accordingly, an aspect disclosed includes a method for generating chondrocytes and/or cartilage, optionally articular like non-hypertrophic chondrocyte cells and/or cartilage like tissue and/or hypertrophic chondrocyte like cells and/or cartilage like tissue, the method comprising:
(a) culturing a primitive streak-like mesoderm cell population, optionally a CD56+ and/or PDGFRalpha+ primitive streak-like mesoderm population, with a paraxial mesoderm specifying cocktail comprising:
  (i) a FGF agonist;
  (ii) a BMP inhibitor, optionally Noggin, LDN-193189, Dorsomorphin; and
  (iii) optionally one or more of a TGFbeta inhibitor, optionally SB431542; and a wnt inhibitor;
  to specify a paraxial mesoderm population expressing cell surface CD73, CD105 and/or PDGFR-beta;
(b) generating a chondrocyte precursor population comprising:
  (i) culturing the paraxial mesoderm population expressing CD73, CD105 and/or PDGFR-beta at a high cell density in a serum free or serum containing media;
  (ii) culturing the high cell density CD73+, CD105+ and/or PDGFRbeta+ paraxial mesoderm population with a TGFbeta agonist in serum free media to produce a high cell density Sox9+, collagen 2+ chondrocyte precursor population; and (c) either:
(i) culturing the high cell density Sox9+, collagen 2+ chondrocyte precursor population with the TGFbeta agonist for an extended period of time to produce articular like non-hypertrophic chondrocyte cells and/or cartilage like tissue; or
(ii) culturing the high cell density Sox9+ collagen2+ chondrocyte precursor population with a BMP4 agonist for an extended period of time to produce hypertrophic chondrocyte like cells and/or cartilage like tissue.

In an embodiment, the TGFbeta agonist is selected from TGFb1, TGFb2, TGFb3 and/or combinations thereof. In an embodiment, the TGFbeta agonist is TGFb1.

In methods described herein, the agonist, inhibitor or component can be added on day 1 of a time period for a specific time period or added repeatedly during a time period for example with media changes. For example, FGF is required for example at day 4 and is added with culture media replacement until day 15.

In an embodiment, the media used in one or more or all steps is serum free. It is demonstrated that a wnt antagonist (e.g. a wnt pathway inhibitor) can increase CD73 and CD105 expression when inducing a primitive streak mesoderm population derived from induced PSCs.

In an embodiment the method is for generating articular like non-hypertrophic chondrocyte like cells and/or cartilage like tissue, and step c) comprises culturing the high cell density Sox9+, collagen 2+ chondrocyte precursor population with the TGFbeta agonist for an extended period of time to produce an articular like non-hypertrophic chondrocyte cells and/or cartilage like tissue.

In another embodiment, the BMP4 agonist is BMP4.

In another embodiment the method is for generating hypertrophic chondrocyte like cells and/or cartilage like tissue, and step c) comprises culturing the high cell density Sox9+ collagen2+ chondrocyte precursor population with a BMP4 agonist for an extended period of time to produce a hypertrophic chondrocyte like cells and/or cartilage like tissue.

In an embodiment, the TGFbeta inhibitor is selected from SB431542 A 83-01, D 4476, GW 788388, LY 364947, RepSox, SB 431542, SB 505124, SB 525334, SD 208 (e.g. any inhibitor of receptors ALK4 and ALK7 and/or TGF-βRI).

The primitive streak like mesoderm that is contacted with mesoderm specifying cocktail is for example CD56+ and PDGFRalpha+ but does not express cardiomyocyte specific precursor differentiation markers.

In an embodiment, of the mesoderm specifying cocktail comprises a TGFbeta inhibitor, optionally SB431524.

In an embodiment, the primitive streak-like mesoderm cell population is cultured with the TGFbeta inhibitor for at least 2 days (optionally T3-5), 3 days or 4 days.

In an embodiment, the mesoderm specifying cocktail further comprises a Wnt inhibitor, optionally DKK1, IWP2, or XAV939. In an embodiment, a Wnt inhibitor is added if for example the percentage of cells expressing CD73 and CD105 or PDGFRbeta is less than 70%, less than 60%, 50%, less than 40%, less than 30% or less than 20%.

The percentage of cells expressing CD73 and CD105 or PDGFRbeta can increase if a Wnt antagonist is used for example for about two days during stage 2 of differentiation. In an embodiment, the mesoderm specifying cocktail comprises a wnt inhibitor, optionally for 2 days, 3 days or 4 days.

In an embodiment, the starting primitive streak like mesoderm population is induced by about day 4 (e.g. KDR+/PDGFRalpha+ cells appear for example at day 5), which for example induces the CD73, CD105 and PDGFR-beta markers to be upregulated in response to BMP inhibition and FGF during the paraxial mesoderm specification phase.

In an embodiment, the paraxial mesoderm population is comprised in embryoid bodies, monolayer culture and/or a combination thereof.

The paraxial mesoderm population can be isolated from any culture, including from an inefficient differentiation, using cell sorting methods based on the expression of the cell surface markers, including for example CD73 and CD105 and/or PDGFR-beta. For example, by enriching for CD73, CD105 and PDGFRbeta cells. The paraxial mesoderm population can also be produced from induced pluripotent stem cells (iPSCs) obtained from a subject.

Accordingly, a further aspect includes a method for generating chondrocytes and/or cartilage, optionally articular like non-hypertrophic chondrocyte cells and/or cartilage like tissue and/or hypertrophic chondrocyte like cells and/or cartilage like tissue, the method comprising:
(a) culturing a starting population of pluripotent stem cells with a primitive streak inducing cocktail to induce a primitive streak-like mesoderm population expressing CD56 and PDGFR-alpha;
(b) culturing a primitive streak-like mesoderm population with a paraxial mesoderm specifying cocktail comprising:
(i) a FGF agonist;
(ii) a BMP inhibitor; optionally Noggin, LDN-193189, Dorsomorphin; and
(iii) optionally one or more of a TGFbeta inhibitor, optionally SB431524; and a wnt inhibitor;
to specify a paraxial mesoderm population expressing cell surface CD73, CD105 and/or PDGFR-beta;
(c) generating a chondrocyte precursor population comprising:
(i) culturing the paraxial mesoderm population expressing cell surface CD73, CD105 and/or PDGFR-beta at a high cell density, optionally in serum free or serum containing media;
(ii) culturing the high cell density CD73+, CD105+ and/or PDGFRbeta+ paraxial mesoderm population with a TGFbeta agonist in serum free media to produce a high cell density Sox9+, collagen 2+ chondrocyte precursor population; and
(d) either
(i) culturing the high cell density Sox9+, collagen 2+ chondrocyte precursor population with a TGFbeta agonist for an extended period of time to produce an articular like non-hypertrophic chondrocyte cell and/or cartilage like tissue; or
(ii) culturing the high cell density Sox9+ collagen2+ chondrocyte precursor population with a BMP4 agonist for an extended period of time to produce a hypertrophic chondrocyte like cell and/or cartilage like tissue.

In an embodiment, the method is for generating articular like non-hypertrophic chondrocyte like cells and/or cartilage like tissue and step d) comprises culturing the high cell density Sox9+, collagen 2+ chondrocyte precursor population with a TGFbeta agonist, optionally TGFbeta1, 2 and/or 3, for an extended period of time to produce an articular like non-hypertrophic chondrocyte like cell and/or cartilage like tissue. TGFbeta agonist used in different steps can be the same or different. In an embodiment, the TGFbeta agonist used to generate a chondrocyte precursor population is the same TGFbeta agonist used for an extended period of time to produce an articular like non-hypertrophic chondrocyte cell and/or cartilage like tissue. In another embodiment, the TGFbeta agonist used to generate a chondrocyte precursor population is a different TGFbeta agonist than that used for an extended period of time to produce an articular like non-hypertrophic chondrocyte cell and/or cartilage like tissue.

In another embodiment, the method is for generating hypertrophic chondrocyte like cells and/or cartilage like tissue, and comprises culturing the high cell density Sox9+ collagen2+ chondrocyte precursor population with a BMP4 agonist for an extended period of time to produce hypertrophic chondrocyte like cells and/or cartilage like tissue.

In an embodiment, the primitive streak inducing cocktail comprises a nodal agonist, such as activin A, a BMP4 agonist, a FGF agonist and a wnt agonist.

According to the methods disclosed herein there are typically up to 4 "stages" for generating chondrocytes and/or articular like cartilage and hypertrophic cartilage, depending on the stage of the starting population, and include 1. Primitive streak induction; 2. Paraxial mesoderm specification; 3. Generation of chondrocyte like cells and 4. Generation of cartilage like tissue. Depending on the starting population, the method can also include a stage 0 which comprises generation of induced pluripotent stem cells from a somatic cell, generating aggregations of PSCs either by making embryoid bodies from hPSCs in culture or by generating a single cell suspension from hPSCs in culture in the presence or absence of self-renewing culture media, The methods described herein are in an embodiment for generating chondrocytes and cartilage tissues from human ESC and tissues. An embodiment comprising these stages is described in further detail below.

Stage 1—Primitive Streak Induction

Human primitive streak mesoderm is induced by contacting the pluripotent cells with primitive streak inducing cocktail for example with activin, BMP4 and basic FGF, for example on and/or between days 1 and 4 of differentiation In some embodiments, the contacting is during days 1-3 for example if the CD56+/PDGFRa+ population is generated sooner. In cell lines and starting populations where endogenous Wnt signaling is absent or low Adding a Wnt agonist can improve the efficiency of primitive streak formation from PSCs, and blocking Wnt signaling with an antagonist inhibit primitive streak formation. Endogenous Wnt signaling, is for example sufficient in cell lines described in the Examples (e.g. HES2). It was found using an iPSC line that a Wnt agonist improved development of a CD56+PDGFRa+ primitive streak-like population when added from day 1 to day 3.

In an embodiment, the wnt agonist is Wnt3a or a GSK-3 selective inhibitor such as CHIR-99021 (Stemolecule™ CHIR99021 Stemgent), 6-Bromolndirubin-3'-Oxime (BIO) (Cayman Chemical (cat:13123)), or Stemolecule™ BIO from Stemgent (cat:04003).

Brachyury expression is also induced during this time, as monitored by gene expression on approximately day 2-3, and the expression of cell surface markers PDGFRa and CD56 by day 4. In human PSCs, PS-like mesoderm induction relies on activin and wnt signaling (see for example, 19 20), and is monitored by Brachyury and PDGFRa expression. CD56 can for example be used to monitor for example human primitive streak cell formation.

Stage 2—Paraxial Mesoderm

The next stage is the generation of paraxial mesoderm, characterized by the expression of transcription factors Meox1 and Nkx3.2. The primitive streak (PS)-like cells can for example be specified to a paraxial fate in monolayer culture, and during this stage (e.g. day 4-6), BMP signaling can be inhibited using a small molecule such as Dorsomorphin, and TGFb signaling can be inhibited using a small molecule such as SB431542. Human paraxial mesoderm requires the addition of FGF (such as bFGF) and it is added to culture media for example, between days 4 and 15 of monolayer culture. A wnt antagonist is also added in some embodiments. The emergence of human paraxial mesoderm is marked by the expression of cell surface markers including CD73, CD105, and PDGFRbeta.

Human paraxial mesoderm can be specified with the BMP inhibitor Dorsomorphin (e.g. days 4-6) and bFGF during for example a monolayer culture between days 4 and 15 of differentiation. Day 15 human paraxial mesoderm is characterized by the expression of cell surface markers CD73, CD105, PDGFRbeta and Meox1 and Nkx3.2 gene expression on day 15. Expression of these markers begins for example at day 12 and is maximal for example around day 15.

Stage 3—Generation of Chondrocytes and Stage 4—Generation of Tissues

Paraxial mesoderm for example from day 15, can be plated directly into a high cell density cartilage tissue formation assay such as A micromass or filter culture. Chondrogenesis is induced in one embodiment with TGFb agonist, for example by culturing with TGFb3 for about 10 days to about 2 weeks, and is characterized by the expression of Sox9 and Collagen 2. A switch to BMP4 agonist such as BMP4 or GDF containing media induces a hypertrophic chondrocyte phenotype. Extended TGFb agonist, optionally with TGFb1 or TGFb3, treatment induces an articular chondrocyte like phenotype in hESC-derived chondrocytes and cartilage tissues, and, GDF5 also induces a hypertrophic phenotype.

Chondrocytes from human paraxial mesoderm are generated by the plating of day 15 CD73+/CD105+ or CD73+/PDGFRbeta+ cells at a high cell density directly in micromass or filter cultures in serum free media containing a TGF agonist such as TGFb1 or TGFb3. Cartilage tissues are generated during this high cell density culture phase by the extended treatment with TGFb agonist or BMP4 agonist.

Any human embryonic stem cell population can be used as the starting population including induced pluripotent stem cell populations. In an embodiment, the starting population is a human embryonic stem cell population (hESC) or an induced pluripotent stem cell population (iPSCs), optionally primary hESC and/or primary iPSC. Many human ESC lines are commercially available and listed for example on the NIH HESC registry. In an embodiment, the human ESC population is a cell line optionally selected from a HES2, H1, H9, or any NIH ESC Registry available hESC cell line; or any human iPS cell line, such as any commercially available iPS cell lines for example as available from System Biosciences.

In an embodiment, the starting population is aggregated into embryoid bodies. In another embodiment, the starting population is cultured in a monolayer.

In an embodiment, the starting population is contacted with the primitive streak inducing cocktail for about 1 to about 5 days and prior to cardiomyocyte specification. In an embodiment, the primitive streak inducing cocktail comprises an activin agonist, optionally activin A or nodal, a BMP4 agonist, optionally BMP4, BMP2, BMP6, BMP7 and/or, BMP10, and a FGF agonist, optionally bFGF, FGF2, FGF4, FGF9 and/or optionally FGF 19, 21, 3, 5, 6, 8a, 16-18, 20 and/or 23. In an embodiment, the primitive streak inducing cocktail further comprises a wnt agonist, optionally selected from Wnt3a and a GSK3b inhibitor such as such as CHIR-99021 (Stemolecule™ CHIR99021 Stemgent), 6-Bromolndirubin-3'-Oxime (BIO) (Cayman Chemical (cat: 13123)), and/or Stemolecule™ BIO from Stemgent (cat: 04003).

The primitive streak-like mesoderm population expresses both CD56 and PDGFRalpha, as measured for example by flow cytometry (FIG. 1B). In some cell lines, the induction takes from T1 (day 1) to T4 (as in the case of the HES2 hESC line used in the Examples). In other cell lines, such as iPSCs for example, this induction may only require two days (from T1-T3). The appearance of cell surface markers such as CD56 and PDGFRalpha indicates that stage 1 is complete and stage 2 can begin.

hiPSCs were differentiated with the following modifications of the protocol shown in FIG. 1A; the Wnt pathway agonist CHIR99061 (1 micromolar) was added to the stage 1 cultures and stage 1 was shortened from 3 to 2 days. The paraxial mesoderm fate was specified in the monolayer cultures by treatment with Dorsomorphin (DM) and SB431542 from day 3 to day 5, and FGF from day 3 to day 14 (Stage 2).

In an embodiment, the iPSCs receive a 3 day induction, and in another embodiment, an iPSC population receives a two day induction. In an embodiment an hESC population receives a 2 day induction and in another embodiment, the hESC population receives a 3 day induction.

Stage 2 can be considered two steps, which results in the generation of a population marked by the expression of CD73, CD105, and/or PDGFR-beta. The cells can be plated in a monolayer culture in the presence of a BMP inhibitor (e.g. such as Dorsomorphin) and a FGF agonist such as basic FGF. Dorsomorphin is effective in inhibiting cardiomyocyte specification, for example, between the window of day 4 to day 6 (T4-T6), and treatment with Dorsomorphin can be limited to this two day period. FGF agonist, optionally basic FGF, is required for example, for the duration of the monolayer culture to specify the mesoderm population to a paraxial mesoderm fate.

Accordingly, in an embodiment, the paraxial mesoderm is specified in a monolayer culture.

In another embodiment, the BMP inhibitor is a type 1 BMP receptor inhibitor and/or soluble BMP receptors, optionally selected from dorsomorphin (DM), noggin, Chordin, LDN-193189, soluble BMPR1a, and/or soluble BMPR1b.

In another embodiment, the primitive streak-like mesoderm population is contacted with the BMP inhibitor for about 1, 2, 3 or 4 days to inhibit cardiomyocyte specification.

In an embodiment, the FGF agonist for specifying the primitive streak-like mesoderm population and/or the paraxial mesoderm population is selected from FGF2, bFGF, FGF4 and/or FGF9.

Figure 3:
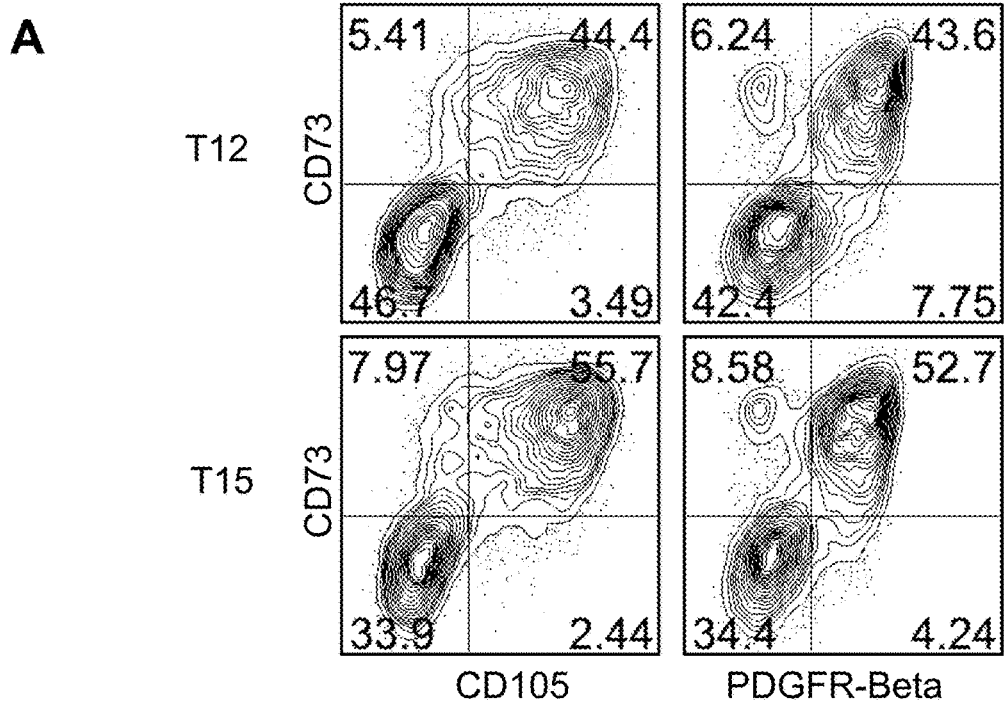
FIG. 3. CD73+CD105+PBeta+ cells contain chondrocyte potential and the potential to generate cartilage-like tissues in-vitro. (A) Flow cytometric analysis of DM+FGF-treated paraxial mesoderm on day 12 and day 15. Double-positive (CD73+CD105+ and CD73+PBeta+) populations were isolated from the double-negative populations by cell sorting and plated in micromass culture. (B) Micromass cultures after 10 days of culture. (C) Micromass cultures after 2 weeks of culture. (D) Photographs of cartilage tissues derived from sorted populations after 5 weeks of culture.
Figure 3:
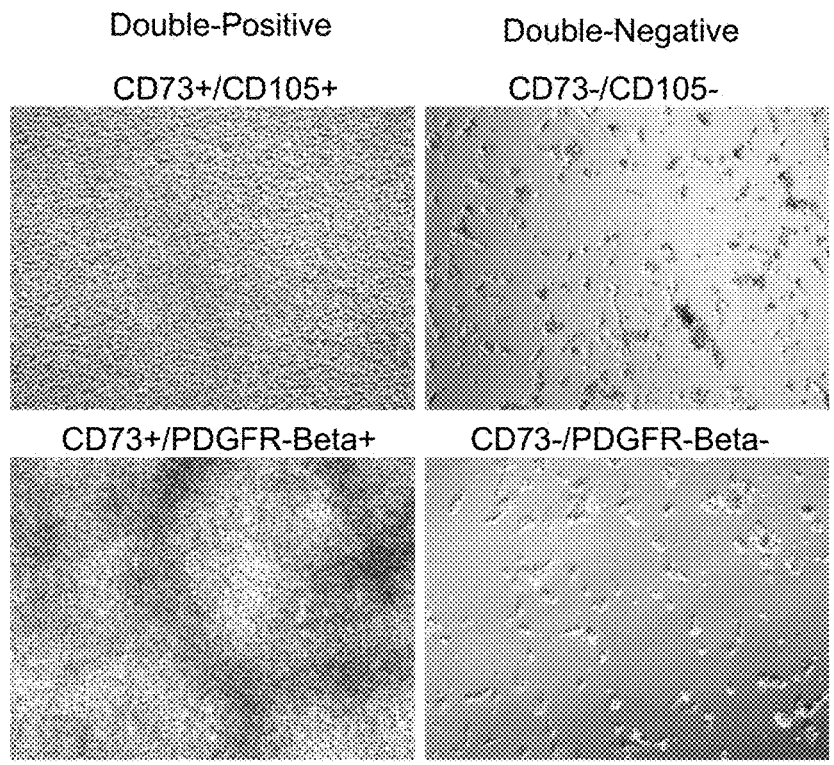
Figure 3:
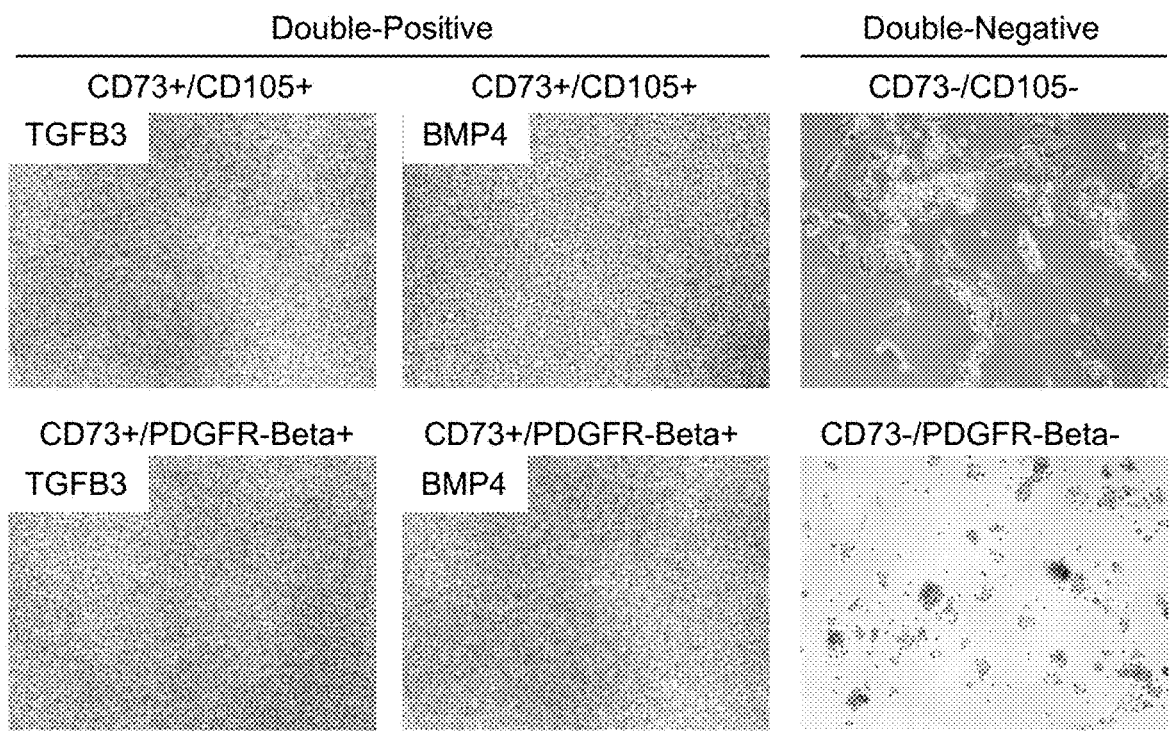
Figure 3:
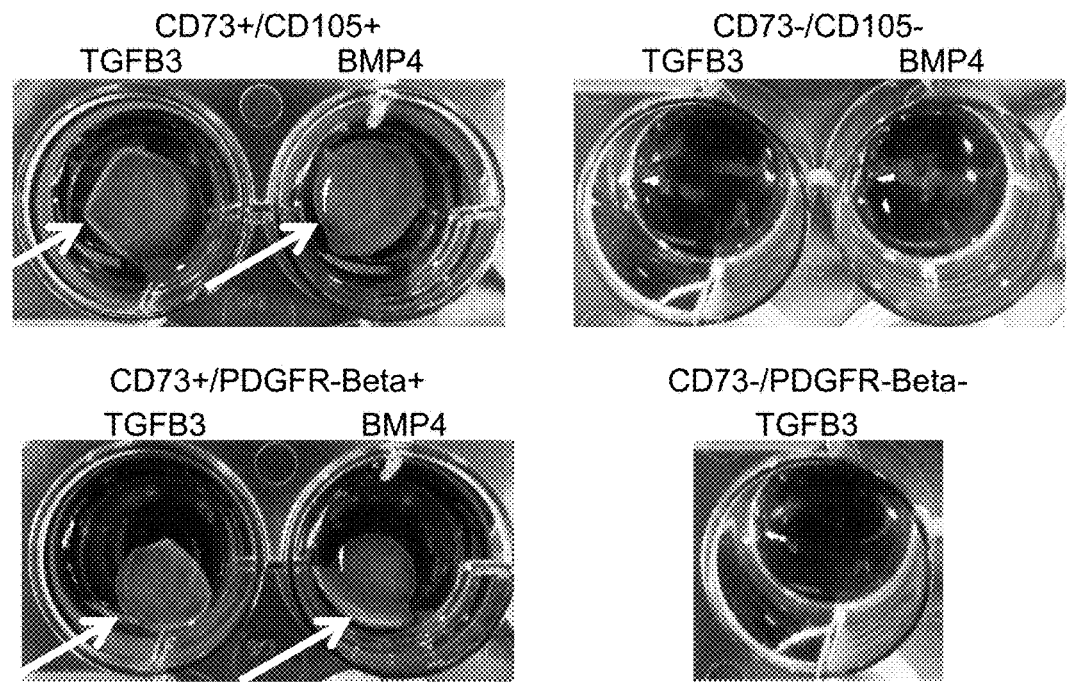

As mentioned, the emergence of this paraxial mesoderm can be monitored by detecting the expression of CD73, CD105 and/or PDGFR-beta on the cell surface (observed by flow cytometry for example as shown in FIG. 2B, 3A). When a population of mesoderm that expresses these 3 markers emerges (by day 15/T15), this stage ends. FIG. 3A shows the upregulation of these markers between T12 and T15. These markers are not expressed on a significant portion of cells between T4 and T10. Over the course of monolayer differentiation (e.g. T4-T15) an upregulation of Meox1 and Nkx3.2, two transcription factors expressed in paraxial mesoderm and somites are detected. Expression of these markers in cultures for example by day 15 indicates that paraxial mesoderm has been generated.

In an embodiment, the primitive streak-like mesoderm population is contacted with the FGF agonist for at least 5 days, 6 days, 7 days, 8 days, 9 days, 10, days, 11 days, 12 days or more (for example from T3-T14) to increase the proportion of cells expressing CD73 and/or CD105 for example, by at least 20%, 25%, 30%, 35%, 40%, 45%, 50%, 55%, 60% or 65% compared to FGF agonist untreated cells.

In an embodiment, the paraxial mesoderm population also expresses transcription factors Meox1 and Nkx3.2 and is negative for Nkx2.5.

The paraxial mesoderm population can be plated in any high cell density format, including for example in a micromass culture, pellet culture or filter culture. For example to generate micromass tissues typically between about 200,000 to about 500,000 cells are plated in one 20 microliter 'spot' to start the tissue formation. Any more cells and they will not adhere due to lack of area available in the spot/tissue culture plastic area, less cells and the 'spot' will not be confluent with cells. As another example, in membrane filter cultures the minimum plating is about 500,000 cells, and the maximum is about 2 million cells per 12 mm diameter filter.

In an embodiment, the paraxial mesoderm population is plated at a cell density between 10 million cells/ml and 50 million cells/ml, optionally at least 10 million cells per 1 ml, 20 million cells/ml, 30 million cells/ml, 40 million cells/ml or 50 million cells/ml for example in a micromass culture. In an embodiment, between about 500,000 and 2 million cells, optionally about 500,000, about 750,000, about 1 million, about 1.25 million, about 1.5 million, about 1.75 million, about 2 million cells are plated in a 12 mm diameter membrane filter culture.

In certain embodiments, serum free methods are used for example to generate CD73+CD105+PDGFRBeta+ paraxial mesoderm from a primitive streak-like mesoderm population using for example bFGF and BMP inhibition.

In an embodiment, optionally during stages 3 and/or 4 the media is serum free and comprises a base media optionally high glucose DMEM+dexamethasone, ascorbic acid, insulin, transferrin, selenium, and proline. An example of a base media is provided for example in reference 18.

As used herein, a base media refers to a mixture of salts that provide cells with water and certain bulk inorganic ions essential for normal cell metabolism, maintain intra- and extra-cellular osmotic balance, provide a carbohydrate as an energy source, and provide a buffering system to maintain the medium within the physiological pH range. Examples of base medias include, but are not limited to, Dulbecco's Modified Eagle's Medium (DMEM), Minimal Essential Medium (MEM), Basal Medium Eagle (BME), RPM1 1640, Ham's F-10, Ham's F-12, alpha-Minimal Essential Medium (aMEM), Glasgow's Minimal Essential Medium (O-MEM), and Iscove's Modified Dulbecco's Medium (IMDM), Stem Pro and mixtures thereof. In one particular embodiment, the basal salt nutrient solution is an approximately 50:50 mixture of DMEM and Ham's F12. In an embodiment, the base media is high glucose DMEM.

In another embodiment, the media comprises a base media comprising insulin, transferrin and optionally selenium in combination with DMEM, Stem Pro®, Mesofate (Stemgent), RMPI 1640 or IDMM.

It is contemplated that the media and/or compositions can further comprise trace elements. Trace elements can be purchased commercially, for example, from Mediatech. Non-limiting examples of trace elements include but are not limited to compounds comprising, aluminum, chlorine, sulfate, iron, cadmium, cobalt, chromium, germanium, sodium, potassium, calcium, phosphate and magnesium. Specific example of compounds containing trace elements include but are not limited to, $AlCl_3$, $AgNO_3$, $Ba(C_2H_3O_2)_2$, $CdCl_2$, $CdSO_4$, $CoCl_2$, $CrCl_3$, $Cr_2(SO_4)_3$, $CuSO_4$, ferric citrate, $GeO_2$, KI, KBr, LI, molybdic acid, $MnSO_4$, $MnCl_2$, NaF, $Na_2SiO_3$, $NaVO_3$, $NH_4VO_3$, $(NH_4)_6Mo_7O_{24}$, $NiSO_4$, RbCl, selenium, $Na_2SeO_3$, $H_2SeO_3$, seleniteNa, selenomethionone, $SnCl_2$, $ZnSO_4$, $ZrOCl_2$, and mixtures and salts thereof.

It is contemplated that amino acids can be added to the defined media. Non-limiting examples of such amino acids are Glycine, L-Alanine, L-Alanyl-L-Glutamine, L-Glutamine/Glutamax, L-Arginine hydrochloride, L-Asparagine, L-Aspartic acid, L-Cysteine, L-Glutamic Acid, L-Histidine, L-Isoleucine, L-Leucine, L-Lysine hydrochloride, L-Methionine, L-Phenylalanine, L-Proline, L-Hydroxyproline, L-Serine, L-Threonine, L-Tryptophan, L-Tyrosine and L-Valine. In certain embodiments, the amino acid is L-Isoleucine, L-Phenylalanine, L-Proline, L-Hydroxyproline, L-Valine, and mixtures thereof.

It is also contemplated that the base media can comprise ascorbic acid.

In addition, the compositions and methods may also comprise other components such as albumin, transferrin, L-glutamine, lipids, antibiotics, betaMercaptoethanol, vitamins, minerals, ATP and similar components may be present. In another specific embodiment, the compositions and methods comprise vitamin $D_3$ and ATP.

In an embodiment, the high cell density spot is maintained for about 0 to 4 days, for example the paraxial mesoderm population is cultured at high cell density for about 0 to about 4 days, optionally 0, 1, 2, 3, or 4 days before addition of TGFbeta3 agonist.

In an embodiment, the CD73+, CD105+ and/or PDGFRbeta+ paraxial mesoderm population is cultured with the TGFbeta agonist in serum free media for at least 3 days, or for about 3 days to about 14 days, optionally at least a week, to produce a Sox9+, collagen 2+ chondrocyte precursor population.

As demonstrated herein, extended TGFbeta signaling can result in generation of an articular like cartilage tissue. In an embodiment, the extended period of time the Sox9+, collagen 2+ chondrocyte precursor population is cultured with a TGFbeta agonist is at least 4 weeks, 5 weeks, 6 weeks, 7 weeks, 8 weeks, 9 weeks, 10 weeks, 11 weeks, 12 weeks, 13 weeks, 14 weeks or more to produce an articular cartilage like tissue. In an embodiment, the chondrocyte precursor population is cultured with the TGFb agonist until lubricin and/or cartilage intermediate layer protein 2 (CILP2) is expressed. In an embodiment, the paraxial mesoderm population and/or the Sox9+, collagen 2+ chondrocyte precursor population is cultured with a TGFb agonist selected from TGFb3, TGFb2 and/or TGFb1.

Switching the culture from comprising TGFb agonist to BMP agonist, induces a hypertrophic chondrocyte population that is growth plate like. In an embodiment, the hypertrophic chondrocyte like cells and/or cartilage like tissue, is cultured with the BMP4 agonist to produce a collagen 10+ and/or Runx2+ hypertrophic chondrocyte like cells and/or cartilage like tissue. In an embodiment, the extended period of time the high cell density Sox9+ collagen2+ chondrocyte precursor population is cultured with the BMP4 agonist, optionally BMP4 or GDF5, is at least 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks or more to generate a cartilage tissue that expresses collagen 2 and/or a hypertrophic chondrocyte population that expresses collagen 10.

For example, stage 3 can comprise a 2-3 day 'spotting' phase which can be done in 2% serum containing media, or serum free. This allows a high cell density of cells to adhere to a small area for example of a tissue culture dish or membrane filter. At the end of this stage of optionally 3 days (+3 days), the majority and/or substantially all cells in the micromass express CD73, CD105, and PDGFRbeta. In an embodiment, this step is followed by TGFB agonist treatment in serum free media for a period of time that is optionally at minimum about 1 week (e.g. at +10 days, the culture is at day 25). By about two weeks (from about 10 to about 14 days), early chondrocyte genes are expressed such as Sox9 and Collagen 2. The cultures can either be maintained in TGFb agonist such as TGFb3 for example over a period of several weeks to several months to generate an articular cartilage (AC) like tissue (e.g. stage 4). Upregulation of the AC gene lubricin is detected for example after about 5-10 weeks of micromass culture.

Histological analyses over this extended period of time shows the generation of higher quality tissue with longer culture, for example after 12 weeks compared to 6 weeks.

The generation of hypertrophic growth plate-like cartilage tissue is achieved by the switching of TGFb agonist containing media to a media containing BMP4 agonist instead. The BMP4 agonist switch typically takes place at about day 25 after the cells have been stimulated with TGFb agonist such as TGFb3 for at least 1 week. This switch causes the micromass cells to convert to a hypertrophic chondrocyte phenotype, which is an enlarged cell (e.g. see FIG. 4C) that expresses genes associated with growth plate differentiation (e.g. collagen 10 and Runx2).

It has been found that immediate stimulation with BMP4 at about 3 days of micromass (when TGFb3 agonist is usually added) results in the micromasses balling up, becoming non-adherent, and/or not surviving and/or making tissue. A switch to BMP4 anytime for example between about 10 days and 6 weeks of stage 3 culture is able to induce this hypertrophic response in TGFb agonist treated micromasses. In an embodiment, the switch to BMP4 agonist, optionally BMP4 is on about day 25 to generate growth plate like cartilage.

Collagen 10 expression, indicative of growth plate hypertrophic chondrocytes is expressed for example after several weeks (e.g. 9-12 weeks in the cell line in Example 1); similar timing wise to lubricin in TGFb agonist treated micromasses. Thus, extended BMP4 agonist treatment results in the generation of collagen 10 expressing growth plate-like cartilage tissue from hPSCs.

Accordingly, in an embodiment, the chondrocyte precursors are cultured in TGFbeta agonist or BMP4 agonist for cartilage tissue formation.

The desired populations at one or more stages can be enriched. For example, the CD73+CD105+ cells and/or CD73+ PDGFR-beta+ can be isolated, optionally by flow cytometry, from the paraxial mesoderm population expressing cell surface CD73, CD105 and/or PDGFR-beta prior to high cell density culture.

The methods described can also be used for example on chondrocyte precursor cells that have been generated using other methods and/or that are isolated from a subject.

Accordingly, in another aspect, the disclosure includes a method of generating chondrocyte like cells comprising:
(a) culturing chondrocyte precursor cells at a high cell density, in serum free or serum containing media;

(b) culturing the high cell density the chondrocyte precursor cells with a TGFbeta agonist in serum free media; and
(c) either
  (i) culturing the chondrocyte precursor cell with a TGFbeta agonist for an extended period of time to produce an articular cartilage like chondrocyte population; or
  (ii) culturing the chondrocyte precursor cell with a BMP4 agonist for an extended period of time to produce a hypertrophic chondrocyte population of cells and/or cartilage like tissue.

In an embodiment, the chondrocyte precursor cells are primary fetal chondrocytes or passaged fetal chondrocytes. In another embodiment, the chondrocyte precursor cells are primary cells obtained from a subject with a cartilage or bone condition or disease. Cells obtained from a subject can be subjected to methods to induce pluripotency prior to high cell density culture. For example, primary chondrocytes can be isolated from patients and tested directly using the micromass methods, or any somatic cell from a patient can be used to make patient specific IPS cells which would then be differentiated using the 4 stages of the method described herein to generate cartilage tissues. Cells obtained from a subject for example from a disease site can be used to test for ameliorating drugs and/or cultured for example where the subject has osteoarthritis, with synovial fluid components or other test substances to try to identify components that propagate and/or ameliorate one or more symptoms. Cells or fluid components can also be obtained from a subject, for example from a non-disease site and used to generate cells and/or tissue for autologous chondrocyte implantation for example wherein the generated cells and/or tissues are administered to a subject. In an embodiment, the cells are used for allograft transplantation.

The steps can be performed in vitro. Alternatively, cells and/or compositions comprising the cells or tissue can be administered for example prior to full cartilage like tissue formation to a subject and monitoring for cartilage formation in vivo. For example, cells prepared using a method described herein and optionally dissociated prior to administration.

The methods can also be employed to generate a paraxial mesoderm population of cells. In an embodiment, the method comprises:
(a) culturing a starting population of pluripotent stem cells with a primitive streak inducing cocktail to induce a primitive streak-like mesoderm population expressing CD56 and PDGFR-alpha;
(b) culturing a primitive streak-like mesoderm population with a paraxial mesoderm specifying cocktail comprising:
  (i) a FGF agonist;
  (ii) a BMP inhibitor; optionally Noggin, LDN-193189, or Dorsomorphin; and
  (iii) optionally one or more of a TGFbeta inhibitor, optionally SB431524; and/or a Wnt inhibitor, optionally DKK1, IWP2, or XAV939;
  to specify a paraxial mesoderm population expressing cell surface CD73, CD105 and PDGFR-beta.

In an embodiment the method further comprises enriching CD73, CD105 and/or PDGFRbeta expressing cells.

In an embodiment, the concentration of a component (e.g. agonist, inhibitor, etc.) used is an effective amount, for example effective to induce the expression of a marker indicative of the desired cell type.

In an embodiment, the FGF agonist is a FGF.

In an embodiment, the concentration of FGF is any concentration between about 2 ng/ml to about 100 ng/ml, optionally about 20 ng/ml.

In an embodiment, the BMP inhibitor is Dorsomorphin (DM).

In an embodiment, the concentration of DM is any concentration between about 0.5 uM and about 5 uM, optionally about 4 uM (e.g. micromolar).

In an embodiment, the TGFb agonist is TGFb1, 2 and/or 3.

In an embodiment, the concentration of TGFb1, 2 and/or 3 is any concentration between about 1 ng/ml and about 50 ng/ml, optionally about 10 ng/ml.

Any number between a specified range includes for example every 0.1 or every 0.5 unit increment.

In an embodiment, the concentration of TGFbeta3 is any concentration between about 1 ng/ml and about 50 ng/ml, optionally about 10 ng/ml.

In an embodiment, the BMP4 agonist is BMP4.

In an embodiment, the concentration of the BMP4 is any concentration between about 10 ng/ml and about 100 ng/ml, optionally about 50 ng/ml.

Methods can also include a step of monitoring, optionally in vitro or in vivo, for proteoglycan production, and/or calcification and/or mineralization, for example by Von Kossa staining. For example von Kossa staining can be used to confirm mineralization and indicates the development of growth plate like cartilage.

A further aspect of the disclosure includes a population of cells or tissue generated using a method described herein, optionally for use for a utility described herein.

Accordingly provided is an isolated population of chondrocyte like cells, optionally articular like non-hypertrophic chondrocyte like cells and/or cartilage like tissue and/or hypertrophic chondrocyte like cells and/or cartilage like tissue, or precursor population generated according to a method described herein.

In an embodiment, the isolated population is a paraxial mesoderm population expressing cell surface CD73, CD105 and PDGFR-beta.

In an embodiment, the isolated population of chondrocyte like cells comprise cells expressing one or more chondrocyte markers and/or genes, for example GDF5, WNT9A, and/or ERG similar to joint interzone cells, lubricin Meox1 and/or CIP2 similar to articular chondrocytes, or RUNX2, SP7, alkaline phosphatase (ALP/ALPL), and/or COL10A1 similar to hypertrophic chondrocyte cells.

A further aspect is a composition comprising the population of articular like non-hypertrophic chondrocyte like cells and/or cartilage like tissue and/or hypertrophic chondrocyte like cells and/or cartilage like tissue, and/or precursor cells generated according to a method described herein; and a carrier. Depending on the use, the carrier can be optionally Polyethylene glycol (PEG), hydrogel, bone scaffolding, bone substitute scaffolding and/or matrigel. Other carriers include for example carrier comprises one or more of a group consisting of sodium hyaluronate, hyaluronic acid and its derivatives, gelatin, collagen, chitosan, alginate, buffered PBS, Dextran and polymers. For example, the carrier can be a carrier that is suitable for use in transplantation applications e.g. pharmaceutical grade carriers. The carrier can also be suitable for stabilizing the cells for transport and/or storage. Cells can for example be cryofrozen and/or tissues can be shipped at room temperature and/or any between room temperature and about 4° C.

The composition can for example be in a slurry comprising dissociated cells for example for administration to a subject. In an embodiment, the composition can comprise other cells for example endothelial cells and/or fibroblasts for example for growth plate cell/cartilage transplantation.

A further aspect includes a cartilage or bone tissue product comprising cells and/or tissue described herein and a scaffold or membrane. For example, during transplantation applications, chondrocytes can be administered to a damaged area in combination with a membrane (e.g. tibial periosteum or biomembrane) or pre-seeded in a scaffold matrix. In an embodiment, the scaffold is a bone substitute.

Cells and tissues generated according to the methods disclosed herein can for example be used for ameliorating symptoms in a subject afflicted with a joint or bone disorder.

Another aspect accordingly includes a method for ameliorating symptoms and/or treating a subject in need thereof comprising administering the population of cells and/or tissues described herein and/or inserting/implanting a product comprising said cells.

Uses of the cells, tissues and products are also provided in another aspect. In an embodiment, the disclosure provides use of the population of cells and/or tissues or composition or product described herein for ameliorating symptoms and/or treating a subject in need thereof.

In an embodiment, the population of cells for a use or method described herein for example that are to be administered to the subject are induced from autologous cells.

In an embodiment, the population of cells is enriched for articular like non-hypertrophic chondrocyte like cells and/or cartilage like tissue.

In an embodiment, the subject has a joint condition such as osteoarthritis, osteochondritis dissecans, polychondritis, and other chondropathies, or joint injuries affecting the cartilage.

In a further embodiment, the population of cells is enriched for hypertrophic chondrocyte like cells and/or cartilage like tissue.

In yet another embodiment, the enriched hypertrophic chondrocyte like cells and/or cartilage like tissue, is adhered to a scaffold or membrane.

In another embodiment, the subject has a bone condition such as a bone fracture, bone break or is in need of a bone replacement for example due to a malignancy or trauma, achondroplasia, osteogenesis imperfect, osteoporosis or other osteopathies.

The generated cells can be optionally immortalized and/or modified for example to stably express a reporter gene operably linked to a promoter of a gene typically expressed in articular chondrocyte like cells such as lubricin promoter and/or typically expressed in hypertrophic chondrocytes such as collagen 10 promoter (e.g. reporter system) to provide a model cell, that can for example be used for testing for candidate substances for their ability to promote, inhibit, maintain or are active in articular chondrocytes or hypertrophic chondrocytes. A large number of reporter genes are known in the art including for example fluorescent proteins such as GFP, RFP, dsRed etc, luciferase. Reporter gene assays are versatile and sensitive methods and can be used to assay numerous candidate substances in high-throughput drug-screening programs.

Also provided herein are kits comprising one or more of a cell or tissue generated according to a method described herein, a product or composition comprising a cell or tissue generated, optionally comprising a reporter system or other modification, according to a method described herein, a combination of at least two selected from an agonist, inhibitor, media, apparatus or other component that can be used in a method described herein and instructions for use for example instructions on how to generate the cells, perform an assay or administer the cell, tissue, composition, or product, and a vial or other container for housing one of these aforementioned cells, tissues, compositions, products, agonists, inhibitors, medias etc.

The cells and tissues generated according to a method described herein can be used for various applications. For example the cells and tissues can be used for predictive drug toxicology and drug discovery. For example, a population of enriched hPSC-derived chondrocytes, articular or growth-plate like, can be used in predictive drug toxicology screens as well as for screens aimed at identifying novel compounds that impact chondrocyte biology and physiology. Drugs which promote the proliferation, but also maintenance, of articular chondrocytes, optionally in the presence of one or more disease mediators, will be of interest as expansion of primary articular chondrocytes from patients in the past has led to the dedifferentiation of the chondrocytes to a mesenchymal like phenotype, and results in less than ideal cartilage replacement.

Accordingly, an embodiment includes a method of testing a candidate chondrogenic modulating substance, the method comprising:
a) contacting a test substance with a chondrocyte precursor lineage cell population, the test substance contacted with the chondrocyte precursor lineage cell population at any step in the method described herein;
b) assessing the effect of the test substance on chondrocyte proliferation, maintenance and/or differentiation compared to a control population generated in the absence of test substance; and
c) identifying the test substance as a candidate chondrogenic modulating substance if the test substance increases or decreases proliferation, and/or affects chondrocyte maintenance or differentiation compared to the control.

The modulating substance can for example be a disease mediator or a component with protective activity. Disease mediators can also be used in the presence or absence of test substances to screen for agents that inhibit and/or reduce the disease inducing effect of the disease mediators.

The cells and tissues are optionally used for assessing cell transplantation protocols ad may be used for cell transplantation. For example, these methods will allow for example comparison of: a) the effects and efficiency of transplanting articular or growth plate like hPSC-derived chondrocytes or cartilage tissues versus autologous chondrocyte transplantation or adult mesenchymal stem cell-derived chondrocytes or cartilage tissues, b) the effects of transplanting articular like cartilage tissues and/or a chondrocyte-cell-slurry to treat various articular cartilage defects in animal models or patients with varying levels of joint disease including osteoarthritis, c) the ability of hESC-derived growth plate-like chondrocytes or cartilage like tissues to be used for bone regeneration (via a cartilage template intermediate).

The cells and tissues can for example be used in tissue engineering applications. For example enriched populations of chondrocytes from hPSC cultures can be generated and used in engineered constructs for example with defined proportions of chondrocytes and other cell types or scaffolding. The hPSC-derived chondrocytes can be seeded for example onto a bone substitute, for example, may allow for cartilage/bone interfaces in vitro, or in vivo. Such products can be transplanted into patients or animals with damage to an osteo-chondral junction.

The methods can be used to establish patient-specific disease models (by generating iPS cell lines from patients for example for diseases comprising a genetic component). Chondrocyte like cell and tissue populations can be established from human patients using methods described herein. In order to analyze the differentiation as well as the phenotypes of these diseased cells, a paraxial mesoderm population can be generated and those cells can be specified to a chondrocyte fate, and finally articular or growth plate like cartilage tissues using protocols described in this disclosure.

The methods described herein can also be used to establish general models of cartilage disease (e.g. hypertrophy) including those associated with osteoarthritis. Without wishing to be bound by theory, BMP4 may be inducing a hypertrophic fate in articular-like chondrocytes and cartilage tissues, which is a pathway which is often upregulated in articular cartilage at the onset of osteoarthritis. As another example, the addition of factors isolated from osteoarthritis patients to cultures described herein can be used to determine whether metabolically active compounds (such as those found in the fat pad in the knee of OA patients) can affect the quality of the tissue in vitro.

Also, as CD73 has been found to identify articular chondrocyte like cells, the use of CD73 by flow cytometry, and the quantitative measure of cell size indicating hypertrophy by flow cytometry, can facilitate high throughput screening of factors which promote articular or growth plate like fates, as well as histology of the tissue itself through marker based assessment methods. Hypertrophy is associated with osteoarthritis for example in mouse models, and is thought to be similarly causative in patients. These applications could for example be used to identify modulators of hypertrophy.

In an embodiment, the candidate chondrogenic modulating substance is a factor isolated from a subject with diseased cartilage or bone. In an embodiment the factor is isolated from a fat pad in a joint, optionally a knee joint, of a subject with arthritis and/or obese or from healthy subjects as controls. In another embodiment, the test substance is added with the BMP4 agonist and the test substance is assessed for its ability to inhibit hypertrophy compared to controls treated in the absence of the test substance. In yet another embodiment, hypertrophy is assessed using flow cytometry, optionally by assessing forward and side scatter.

In another embodiment, the method comprises a method of assessing a candidate articular chondrocyte proliferation inducer comprising:
(a) obtaining articular like non-hypertrophic chondrocyte cells and/or cartilage like tissue generated according to the method of described herein,
(b) culturing the articular like non-hypertrophic chondrocyte cells and/or cartilage like tissue with a test substance;
(c) measuring the articular like non-hypertrophic chondrocyte like cell proliferation;
(d) detecting an increase in proliferation compared to articular like non-hypertrophic chondrocyte cells and/or cartilage like tissue cultured in the absence of the test substance indicating that the test substance is a candidate articular chondrocyte proliferation inducer.

A further embodiment includes a method of assessing a candidate hypertrophic chondrocyte proliferation inducer comprising:
(a) obtaining hypertrophic chondrocyte like cells and/or cartilage like tissue, generated according to the method described herein,
(b) culturing the hypertrophic chondrocyte like cells and/or cartilage like tissue, with a test substance;
(c) measuring hypertrophic chondrocyte, cell proliferation;
(d) detecting an increase in proliferation compared to hypertrophic chondrocyte like cells and/or cartilage like tissue cultured in the absence of the test substance indicating that the test substance is a candidate hypertrophic chondrocyte proliferation inducer.

In an embodiment, CD73 articular like non-hypertrophic chondrocyte cells and/or cartilage like tissue are isolated prior to culture with the test substance, optionally isolated by flow cytometry.

In another embodiment, the articular like non-hypertrophic chondrocyte cell and/or hypertrophic chondrocyte like cell comprise a reporter gene functionally coupled to an articular chondrocyte specific promoter (i.e. articular chondrocyte reporter system), optionally a lubricin promoter element and/or a reporter gene functionally coupled to a hypertrophic chondrocyte specific promoter, optionally a collagen 10 promoter element (i.e. hypertrophic chondrocyte reporter system); and a compound that induces articular chondrocyte differentiation (identified by measuring the articular chondrocyte reporter system activity) and/or a compound that induces hypertrophic chondrocyte differentiation (identified for example by measuring hypertrophic chondrocyte reporter system activity).

In an embodiment, an increase in proliferation is measured using one or more of the following methods: a 3H Thymidine incorporation assay; a 5-bromo-2'-deoxyuridine (BrdU) incorporation assay; and a propidium iodine assay.

A further embodiment includes a method of assessing AC cell and/or GPC cell toxicity or protective activity of a test compound, comprising:
(a) generating articular like non-hypertrophic chondrocyte cells and/or cartilage like tissue and/or GPC like cells and/or growth plate cartilage according to the method described herein;
(b) culturing the articular like non-hypertrophic chondrocyte cells and/or cartilage like tissue and/or GPC cells with the test substance;
(c) measuring cell toxicity and/or cell protective activity of the test substance;
(d) detecting an increase in cell toxicity compared to articular like non-hypertrophic chondrocyte cells and/or or GPC cells and/or tissue cultured in the absence of the test substance indicating that the test substance is toxic to articular chondrocyte and/or GPC cells or detecting an increase in protective activity (e.g. a decrease in cell toxicity) compared to articular like non-hypertrophic chondrocyte cells and/or GPC cells and/or tissue cultured in the absence of the test substance indicating the test substance is protective.

In an embodiment, cell toxicity is measured using one of the following assays: a Trypan blue dye assay; a luciferase assay; a tetrazolim salt conversion assay such as a MTT assay and a WST-1 assay.

As demonstrated herein, IL-1beta can induce osteoarthritis like changes in a cartilage cell population. Il-1b and other mediators, for example other cytokines and knee fat pad components (e.g. disease mediators) as well as mechanical disruption can be used in screening methods described herein. For example, cells produced using a method described herein can be contacted with such disease mediators or mechanical disruption in the presence or absence of a test substance (e.g. either added prior to the addition of the disease mediators or mechanical disruption or after the cells have been contacted and/or mechanically disrupted to assess the test substances ability to inhibit or reverse the disease mediator function.

In an embodiment, the AC like chondrocytes and/or cartilage like tissue or the hypertrophic like chondrocytes and/or cartilage like tissue is/are contacted with a disease mediator optionally prior to culture with the test substance.

In an embodiment, the disease mediator is a cytokine, optionally IL-1 beta. In another embodiment, the disease mediator is a joint fat pad component, optionally a knee fat pad component.

In an embodiment, the screening assay comprises one or more of the following analyses or assays: histological analysis, biochemical assays such as those that quantify the production of glycosaminoglycans and proteoglycans, gene expression analyses, gain/loss of a fluorescent reporter such as lubricin or collagen 10 by microscopy or flow cytometry, gain or loss of CD73 cell surface receptor expression, assays for cell death, and flow cytometry for cell size which can indicate chondrocyte hypertrophy.

CD73 can be used as a positive selection marker for cell sorting experiments to enrich for articular-like chondrocytes. These markers could facilitate the isolation of articular chondrocytes from primary sources of tissue, to be used in conjunction with allogenic or autologous cartilage repair strategies currently in use.

Accordingly a further aspect includes a method of isolating articular chondrocytes comprising: contacting a mixed population of cells comprising chondrocytes with an antibody (or other binding molecule) that binds CD73 under conditions that allow for the formation of an antibody (or other binding molecule):CD73 cell complexes; and isolating the antibody CD73 cell complexes. This can be done by a number of known immunological methods known in the art including cell sorting based methods.

In an embodiment the mixed population of cells comprises non chondrocyte cells, non-articular chondrocyte like cells, and/or hypertrophic chondrocyte like cells.

In an embodiment, the antibody is coupled to a tag such as a bead such as a sepharose bead or magnetic bead that for example facilitates isolation.

The combination of CD73, CD105, and PDGFR-beta can be used as positive selection markers for isolating paraxial/chondrogenic mesoderm from other lineages or progenitors of other lineages. As other lineages such as the cardiac lineage are often induced using similar protocols to those used to generate paraxial mesoderm, isolation of paraxial mesoderm by cell sorting using these cell surface markers provides a means to enrich for this population. For example, the cells are enriched using flow cytometry.

Accordingly an embodiment includes a method of isolating paraxial chondrogenic mesoderm population of cells comprising: contacting a population of cells comprising paraxial chondrogenic mesoderm cells with a cocktail comprising a CD73 specific binding agent, CD105 specific binding agent, and a PDGFRbeta specific binding agent; and enriching for CD73+, CD105+ and PDGFRbeta+ cells. In an embodiment, the binding agent is an antibody. In another embodiment, the cells are enriched using flow cytometry. Also provided is an isolated paraxial chondrogenic mesoderm population of cells prepared according to the method described herein and which can be comprised in a composition or in a product as described herein. These cells can also be used in screening assays described herein. The paraxial mesoderm population can be used for example for generating other cell types for example for generating skeletal muscle progenitors, adipocyte progenitors (fat cells) and potentially bone progenitors (osteoblasts).

Further, the definitions and embodiments described in particular sections are intended to be applicable to other embodiments herein described for which they are suitable as would be understood by a person skilled in the art. Selections and combinations of different agonists, inhibitors and/or other components including for example agonists, inhibitors, etc. recited in definitions are also contemplated. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Results

Chondrocyte formation in vitro includes the induction of a primitive-streak-like (PS) population as embryoid bodies (stage 1), the specification of paraxial mesoderm in a monolayer culture (stage 2), the generation of chondrocyte progenitors in high cell density micromass culture or on collagen-coated membrane filters (stage 3), and the specification of articular and growth plate chondrocytes and cartilage tissues in micromass or filter cultures (stage 4) (FIG. 1A).

A first step in differentiation from a pluripotent stem cell (PSC) state is the formation of a PS population which, in the embryo, occurs during gastrulation when the three germ layers (endoderm, mesoderm, and ectoderm) are formed. The PS population and endoderm and mesoderm subsets can be induced from PSCs using a combination of Activin A (activin, a surrogate for Nodal), Wnt, and BMP signaling molecules (Nostro, Cheng et al. 2008, Kattman, Witty et al. 2011, Craft, Ahmed et al. 2013). A PS population induced with activin, BMP4 and bFGF can be observed by the expression of cell surface markers CD56 and PDGF receptor alpha (PDGFRa) (FIG. 1B).

hESC derived primitive streak (PS) mesoderm expresses CD56, PDGFRalpha and KDR, as shown in FIG. 1C. hIPSCs were induced to a PS mesoderm population using Activin A (3 ng/ml), BMP4 (1 ng/ml), basic FGF (5 ng/ml) and CHIR99061 (1 micromolar), a small molecule Wnt agonist during days 1 and 3 of induction. hIPSCs were induced for a two day period (day 1 to day 3) instead of a three day period (day 1 to day 4) as in the case for the HES2 hES cell line (FIG. 1C). hIPSC-derived PS mesoderm also expresses CD56, PDGFRalpha and KDR (FIG. 1D), however these cell surface markers are not expressed if hiPSCs are induced in the absence of CHIR99061 (FIG. 1E).

With no additional factors beyond day 4 of culture, progenitors contained within this population, can be specified to a cardiogenic fate as observed by co-expression of the cell surface markers KDR and PDGFRa at T5 (FIG. 2A, 0 DM, 0 FGF), and the subsequent expression of the cardiac transcription factor Nkx2.5 on day 15 (T15) (Kattman, Witty et al. 2011), FIG. 2C).

To generate chondrocytes, it is essential to first specify this PS population to a paraxial mesoderm fate. Previous studies have shown that mesoderm populations that express cell surface markers often found on mesenchymal stem cells, CD73 and CD105, have chondrogenic potential (Hwang, Kim et al. 2006). The expression of these two cell surface markers, as well as the expression of transcription factors Meox1 and Nkx3.2 combined with the lack of expression of Nkx2.5 to monitor the emergence of a paraxial mesoderm population was used. Previous experiments in the mouse ESC model system have shown the importance of inhibiting the BMP signaling pathway in the context of FGF signaling to prevent the emergence of cardiac mesoderm and promote the development of paraxial mesoderm (Craft, Ahmed et al. 2013). The addition of the inhibitor of type I BMP receptors Dorsomorphin (DM) for a period of two days from T4 to T6 (days 4 to 6 of differentiation) changed the expression patterns of PDGFRa and KDR by as early as T5, as the cells expressed less PDGFRa than untreated mesoderm (FIG. 2A). The addition of bFGF did not change the PDGFRa/KDR population drastically. Very few cells in untreated mesoderm conditions expressed CD73 and CD105 (7.46%, FIG. 2B). Treatment with DM increased this population only slightly, however, treatment with FGF from day 4 until day 15 increased the proportion of cells expressing CD73 and CD105 dramatically (52%, FIG. 2B). The changes in expression of these surface markers were accompanied by the upregulation of paraxial genes Meox1 and Nkx3.2 (FIG. 2C). Treatment with both DM from T4-T6 and bFGF from T4-T15 resulted in a more robust CD73/CD105 population (67%) and even higher expression of Meox1 and Nkx3.2 (FIG. 2C), suggesting that both BMP inhibition and FGF treatment are required for paraxial mesoderm specification from the PS population. In addition to CD73/CD105 expression, CD73-positive cells derived from FGF- or DM+FGF-treated monolayers also expressed the PDGF receptor beta (PDGFR-beta, PBeta), suggesting that paraxial mesoderm also expresses this cell surface marker (FIG. 2B).

During paraxial mesoderm specification in the monolayer culture, it was observed that Wnt pathway inhibition (during the two day period after PS mesoderm induction (days 4 to 6 for hESC, days 5 to 7 for hIPSCs)) resulted in an increase in the percentage of cells expressing the cell surface markers CD73 and CD105 on day 15 of differentiation (FIG. 2C). Thus, in some cell lines, the efficiency of paraxial mesoderm specification may be improved in the presence of a Wnt pathway antagonist immediately following the PS mesoderm induction phase.

Previous studies have shown that TGFBeta/BMP signaling is required to generate chondrocyte progenitors from paraxial mesoderm. It has been found that TGFB3 (as well as TGFbeta1 or TGFbeta2) stimulation is required for stage 3 (e.g. starting at day 15), as direct plating of this mesoderm into BMP4 containing media resulted in the development of non-adherent cell aggregates that did not form cartilage tissue. Following 10 days of TGFb3 treatment (day 25 total), cultures could be switched to media containing BMP4 or maintained in TGFb3 (stage 4) in order to specify subsets of chondrocytes (articular/non-hypertrophic or growth plate/hypertrophic). To determine the chondrocyte potential of the day 15 mesoderm populations, the cells were plated at high cell density in a 20 microliter volume on tissue culture treated Petri dishes for an hour (micromass) and then the 'spot' was submerged/covered with media. In our initial studies, the cells were 'spotted' in a media containing 2% fetal bovine serum. However, this short serum exposure can be omitted with no effects on cartilage formation at later stages, making this protocol optionally serum-free. After 2 to 3 days, serum-free media containing TGFb3 is added to the culture to generate chondrocyte progenitors. Populations derived from the 4 different mesoderm (0 DM+/-FGF; 4 µM DM+/-FGF) were tested in this micromass assay. While all four mesoderm populations adhered to the dish (FIG. 2D) within 1 day of culture, different phenotypes were observed after 1 week. Contracting (beating) cardiomyocytes, quantified by the expression of cardiac troponin T (cTnT) by flow cytometry (FIG. 2E) were observed in micromasses derived from untreated mesoderm (0 DM, 0 FGF). Mesoderm treated with DM alone did not remain adherent to form chondrocytes, but instead aggregated in long strands that were washed away with media changes. FGF-treated, as well as DM+FGF-treated cells survived the first week of micromass culture as an adherent layer of cells, and did not generate any cardiomyocytes. After 4 weeks of micromass culture, cells treated in the monolayer phase with DM+FGF generated cartilage-like tissues that could be observed by eye (approximately 1 cm in diameter). Cells that were treated in monolayer phase with FGF alone did not maintain a cartilage tissue phenotype, and detached from the culture dish (FIG. 2F). While both FGF-treated and DM+FGF-treated monolayer cultures expressed similar levels of CD73/CD105/PDGFR-Beta, the paraxial gene expression at day 15, as well as the overall survival of the cartilage tissue, suggests that both BMP inhibition (here in the form of DM treatment) and FGF stimulation is required to specify a paraxial mesoderm fate that has the potential to form cartilage-like tissues in-vitro.

To determine if CD73, CD105 and PBeta are expressed on the populations with chondrocytes potential in the hESC differentiation cultures, CD73+CD105+ and CD73−CD105− and CD73+PBeta+ and CD73−PBeta− fractions were isolated from DM+FGF-treated monolayers on day 15 and assayed in the micromass cultures (FIG. 3A). After 10 days in micromass the CD73+CD105+ cells and the CD73+PBeta+ cells adhered and survived. The double-negative cells in both experiments failed to survive under these conditions (FIG. 3B). After two weeks, cartilage tissues developed in the cultures derived from the CD73+CD105+ and CD73+PBeta+ sorted cells (either maintained in TGFB3 or switched to BMP4-containing media). In contrast, the double-negative cells in both cases failed to form any cartilage tissues (FIG. 3C). The differences in the potential to generate cartilage tissue are shown in FIG. 3D. These data demonstrate that the CD73+CD105+PBeta+ cells have the potential to generate chondrocytes and cartilage-like tissues, while cells lacking the expression of these markers do not.

Access to the appropriate paraxial mesoderm population derived at the end of stage 2, and the generation of chondrocyte progenitors at the end of stage 3, provided an opportunity to study the development of two subtypes of chondrocytes, articular chondrocytes (ACs) and growth plate chondrocytes (GPCs). After the paraxial mesoderm cells are stimulated with TGFb3 for about 10 days, these chondrocyte/cartilage cultures can either be maintained in TGFb3 containing media or switched to BMP4-containing media for several months (stage 4). TGFb3 or BMP4-treated cultures form cartilage-like tissues over the course 12 weeks that can be analyzed histologically using stains that indicate the presence of a cartilage-specific extracellular matrix (toluidine blue) and by the expression of genes associated with either articular cartilage or growth plate cartilage. Morphologically, chondrocytes found in TGFb3-treated cartilage tissues have a small fibroblastic-like phenotype, while BMP4-treated chondrocytes are round with cobblestone-like appearance (FIG. 4A). TGFb3-treated cartilage stain uniformly with toluidine blue contains small cells (chondrocytes) dispersed evenly throughout the tissue (13 week old tissues, FIG. 4B). In contrast, the BMP4-treated tissue contains enlarged hypertrophic chondrocytes. The remarkable increase in chondrocyte size in BMP4-treated cartilage tissues may be indicative of chondrocyte hypertrophy, a normal process involved with GPC differentiation. Hypertrophic chondrocytes in the growth plate in-vivo are marked by collagen 10 expression. The growth plate differentiation program ultimately leads to cell death, leaving a calcified matrix on which new bone can be formed. Hypertrophy was also observed in BMP4-treated cartilage tissues by flow cytometric analysis using forward and side scatter plots of live cells (FIG. 4C). TGFb3-treated chondrocytes form a tight population of smaller, less granular cells, while BMP4-treated cells display a larger forward scatter (FSC), signifying larger cell size, as well as a larger side scatter (SSC), signifying higher cell granularity at all time points assessed (3 week and 5 week micromasses are shown).

Histologically, TGFb3-treated cartilage tissue appears to have many of the same characteristics of the future site of articular cartilage of fetal femurs aged 19 weeks (upper panel, FIG. 4D), while hypertrophic chondrocytes found in BMP4-treated cartilages resemble the appearance of the growth plate chondrocytes found near the subchondral bone area of the fetal femur (lower panel). These phenotypes suggest that cartilage tissues with characteristics of the two unique subtypes of cartilage have been generated in-vitro from human PSCs. Primary fetal chondrocytes isolated from the knee joint were also cultured in a micromass assay, identical to the protocol used for day 15 hPSC-derived paraxial mesoderm, and also generated cartilage tissue in-vitro. Histologically, TGFB3-treated and BMP4-treated fetal chondrocyte derived cartilage tissues also look very similar to cartilage tissues derived from hPSCs. FIG. 4E shows that replacing BMP-4 with GDF5 generates hypertrophic chondrocytes similar to those in FIG. 4A.

Similar differences in cell size and morphology were observed in 12-week-old cartilage tissues generated from hiPSCs with TGFbeta3 and BMP4. Tissues stained metachromatically with Toluidine blue which indicates the presence of proteoglycans (FIG. 4F). As expected, type II collagen protein was present in hPSC-derived tissues generated under both conditions (FIG. 4G). Type X collagen was not detected in either tissue at this time point. Lubricin protein was present in TGFbeta3− but not in the BMP4-treated micromass tissue (FIG. 4H), and was found preferentially in the flattened cells that line the top of the tissue structure. Taken together, these findings provide strong support for the interpretation that sustained TGFbeta3 signaling promotes the development of articular chondrocytes that can generate articular cartilage-like tissue, whereas BMP4 signaling induces the differentiation of hypertrophic (enlarged) chondrocytes that form cartilage with growth plate characteristics.

Figure 1:
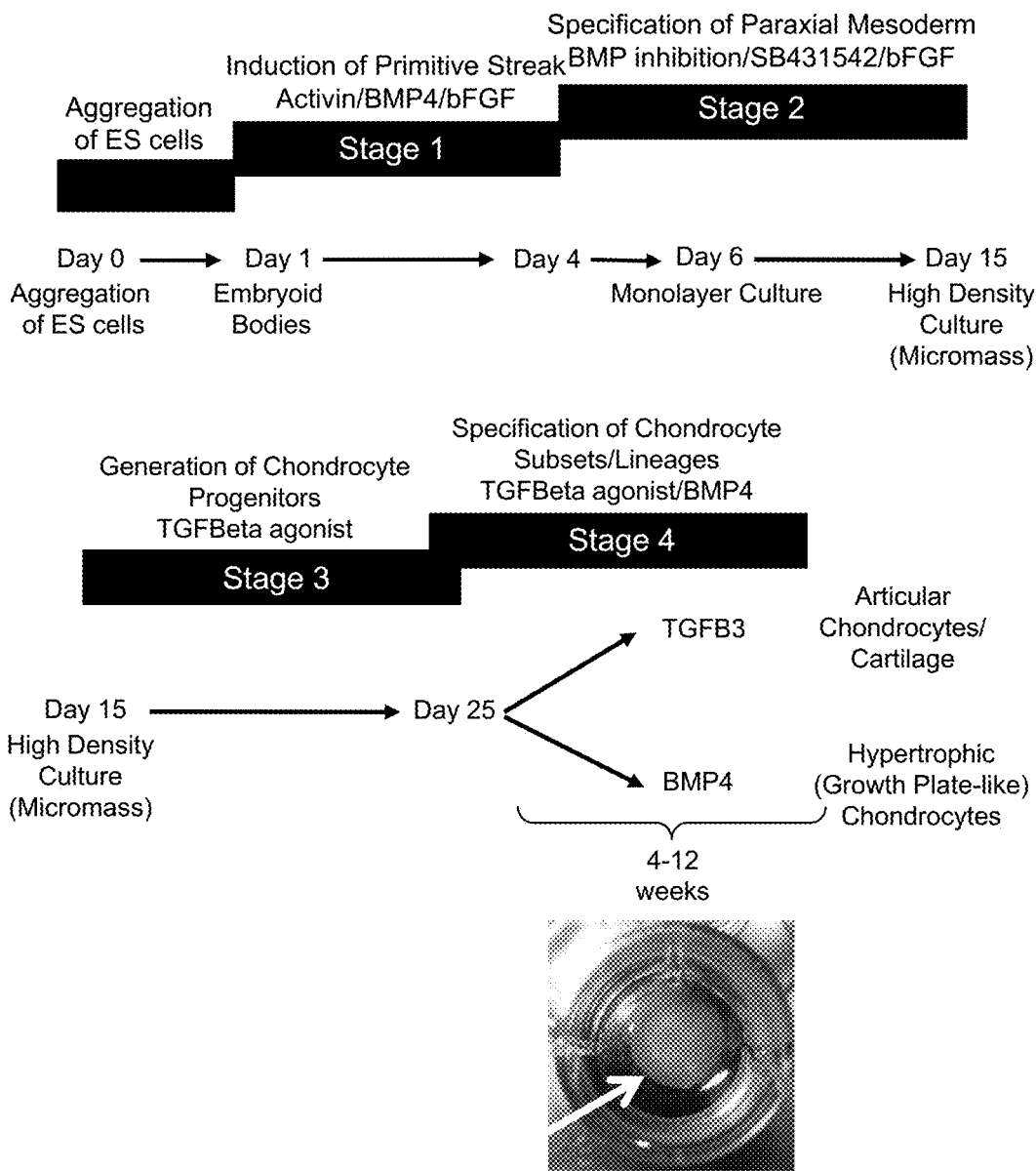
FIG. 1. Serum-free differentiation of paraxial mesoderm, chondrocyte progenitors, and cartilage tissues from human pluripotent stem cells (hPSCs). (A) hPSCs are differentiated in 4 stages including the induction of a primitive streak-like mesoderm population (stage 1) using Activin A, BMP4 and basic (b) FGF from days 1 to 4 of differentiation as embryoid bodies. On day 4 (T4), mesoderm populations are monitored by the expression of CD56 and PDGFRa on the cell surface by flow cytometry (B). Day 4 mesoderm cells are specified to a paraxial mesoderm fate in monolayer culture by treatment of Dorsomorphin, a BMP inhibitor, a TGFbeta inhibitor SB431542, and bFGF, from days 4 to 6 and bFGF from days 4 to 15 (stage 2). Day 15 paraxial mesoderm cells can generate chondrocyte progenitors by plating in a high density 'spot' termed micromass, or by plating onto collagen coated membrane filters (not shown) in the presence of TGFB3 for approximately 10 days (stage 3). Chondrocyte progenitors can be specified to articular chondrocytes or growth plate-like chondrocytes in a cartilage tissue format during stage 4 of differentiation by extended stimulation with TGFB3 (articular) or BMP3 (growth plate-like) for example for 12 weeks. Tissues have been kept in culture for at least 7 months. Efficient induction of a primitive streak-like population from hESCs (C) and hIPSCs (D,E) was confirmed by the expression of CD56 and PDGFRa by flow cytometry on day 3 of differentiation. hESCs were induced to generate a primitive streak population with the following cytokines: Activin A (2 ng/ml), BMP4 (3 ng/ml) and basic (b) FGF (5 ng/ml). hiPSCs were induced to generate a primitive streak-like mesoderm population (Stage 1) using Activin A (3 ng/ml), BMP4 (1 ng/ml), bFGF (5 ng/ml) in the presence (C) or absence (D) of the Wnt pathway agonist CHIR99061 (1 µM) from days 1 to 3 of differentiation as embryoid bodies.
Figure 1:
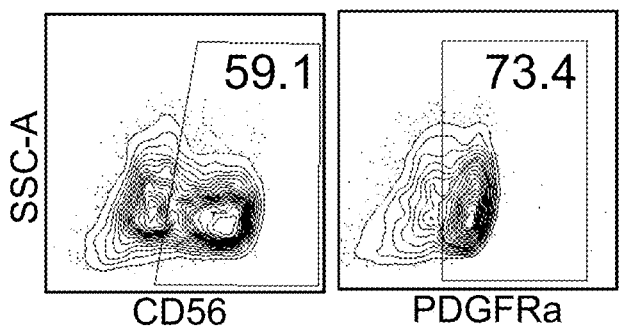
Figure 1:
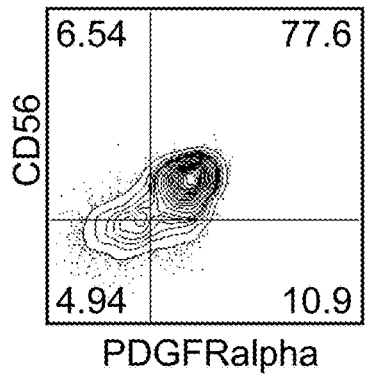
Figure 1:
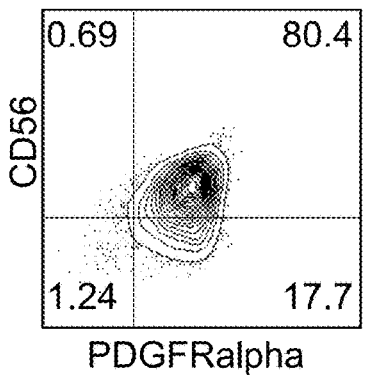
Figure 1:
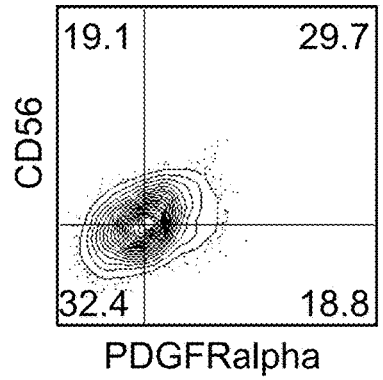
Figure 4:
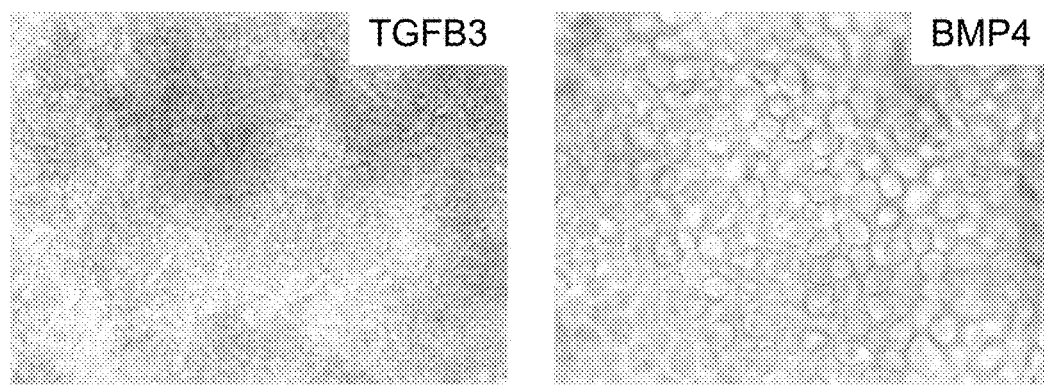
FIG. 4. TGFB3 and BMP4 specify chondrocytes and cartilage-like tissues with articular cartilage and growth plate cartilage phenotypes. (A) Micrographs of 5 week old micromasses derived with TGFB3 or BMP4, 20× magnification. (B) Tissue histology (stained with toluidine blue) of 13 week cartilage tissues derived with TGFB3 or BMP4. Toluidine blue stains cartilage tissues metachromatically, and these tissue sections are pink/purple in color indicating that cartilage tissue is present. (C) Flow cytometric analysis of forward and side cell scatter parameters of 3 week and 5 week old micromasses. Side scatter indicates cell granularity and forward cell scatter indicates cell size. (D) Comparison of hPSC-derived micromass tissues to fetal primary chondrocyte derived micromass tissues and the developing human fetal femur cartilage. Articular cartilage regions appear to have smaller cells in size compared to growth plate like regions, which contain cells which appear enlarged (hypertrophic). Cartilage tissues in micromass as well as in the fetal femur stain uniformly with the toluidine blue stain (images are pink/purple in color and indicate the presence of cartilage proteins). The BMP4-treated micromass tissues contain a large number of enlarged cells which is similar to the bottom panel of the fetal cartilage which represents a growth plate cartilage. TGFB3 treated micromass cultures contain fewer, if any, enlarged chondrocytes, and appear similar to the upper panel of the fetal cartilage which is the site of articular cartilage. (E) Micrograph using GDF5 instead of BMP4 to generate hypertrophic chondrocytes. (F) Histological analyses of cartilage tissues derived from hiPSCs stained with Toluidine blue after 12 weeks. (G,H) Immunohistochemical staining of hESC-derived cartilage tissues for type II Collagen (G, 8 week tissues), and lubricin (H, 12 week tissues).
Figure 4:
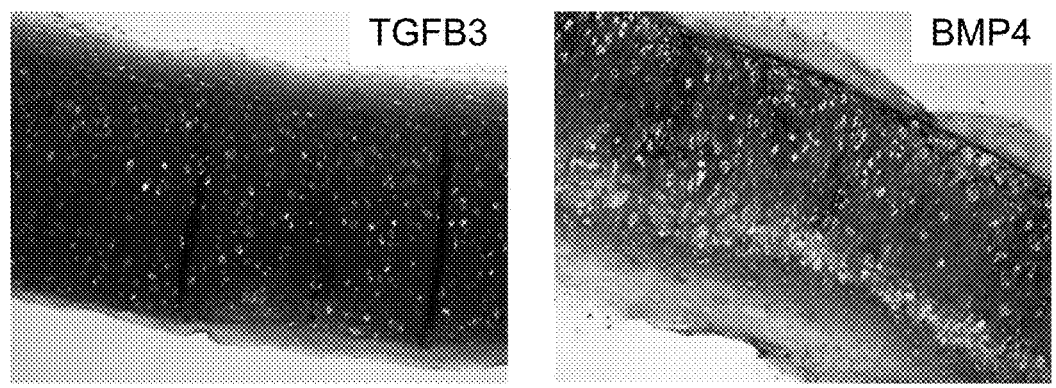
Figure 4:
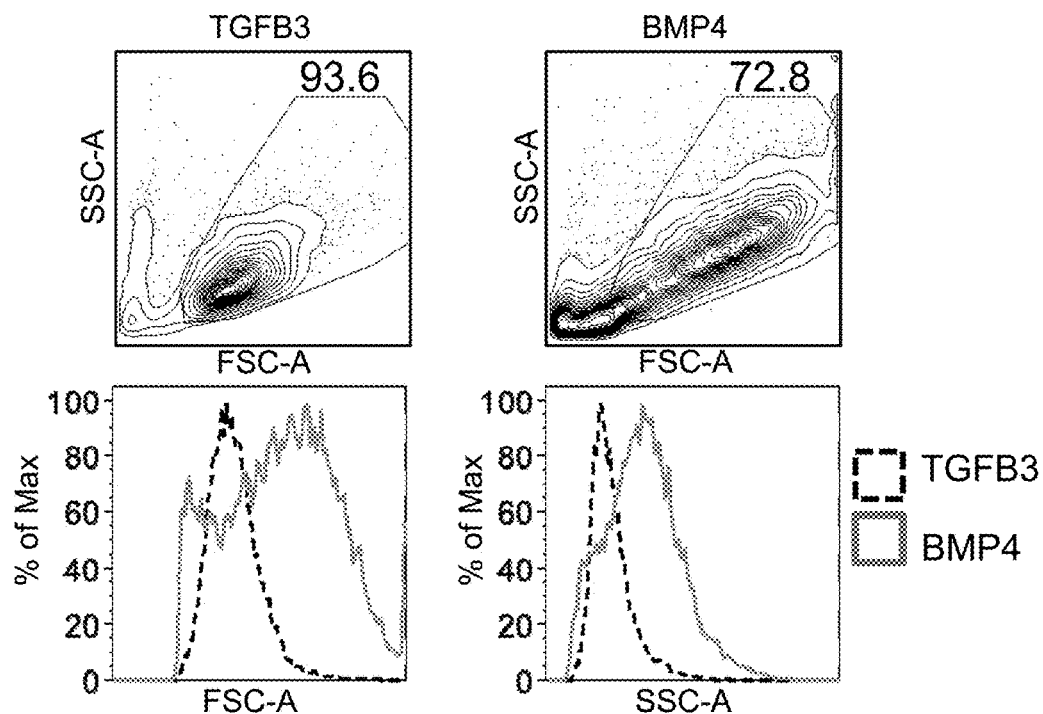
Figure 4:
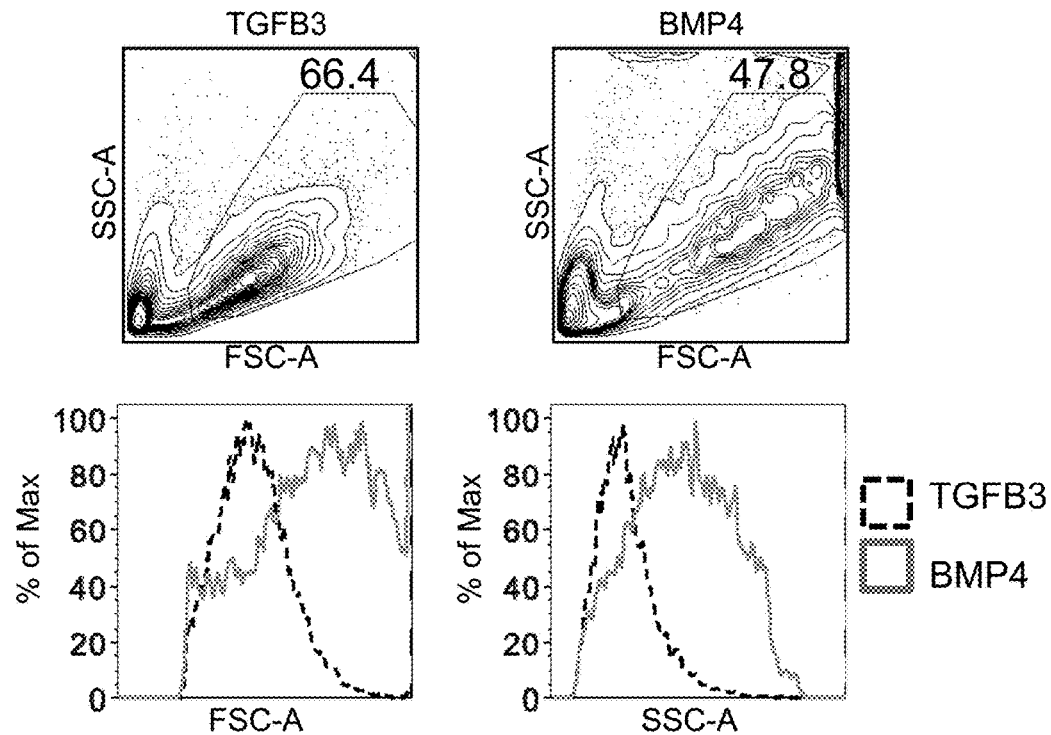
Figure 4:
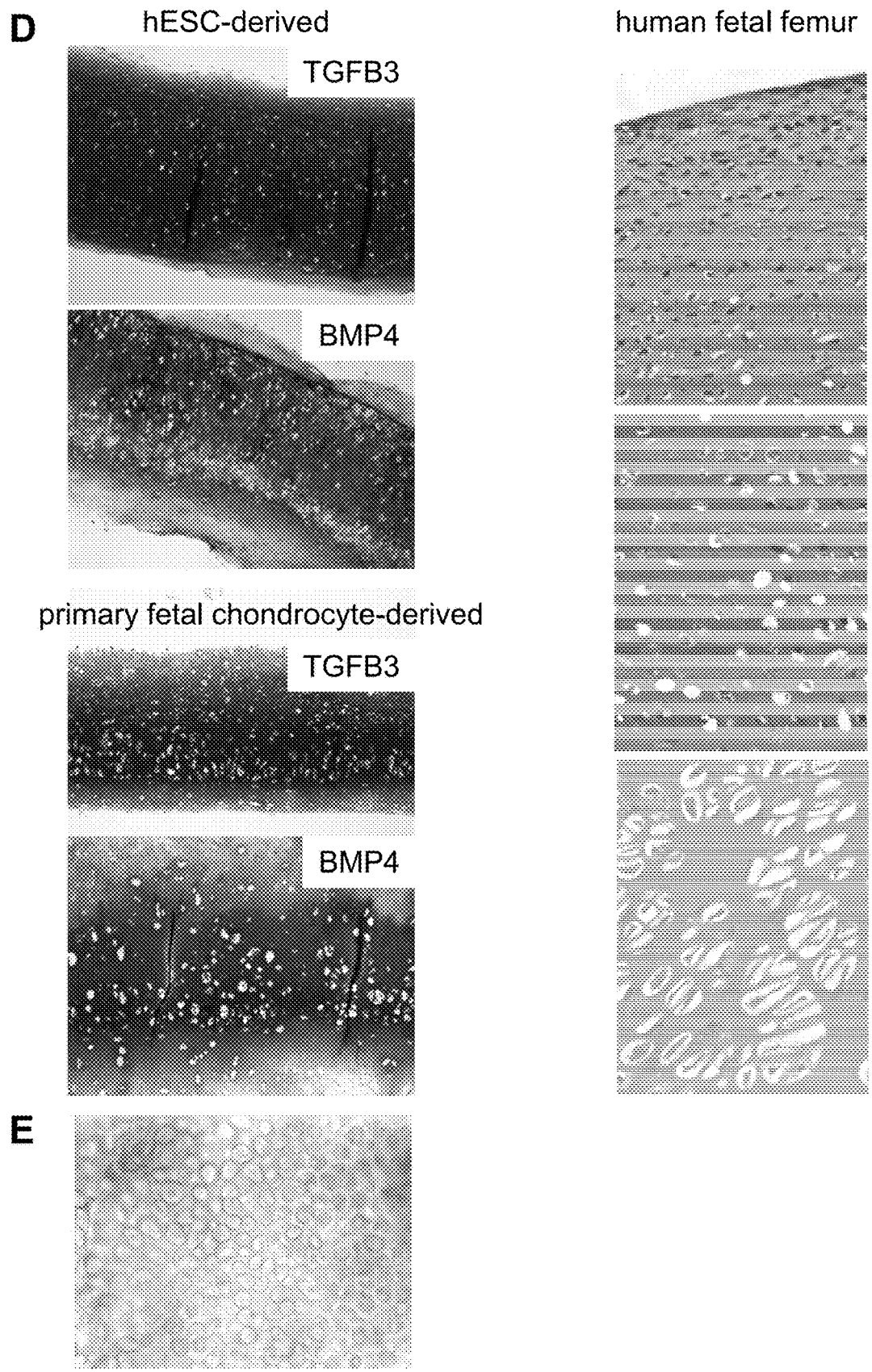
Figure 4:
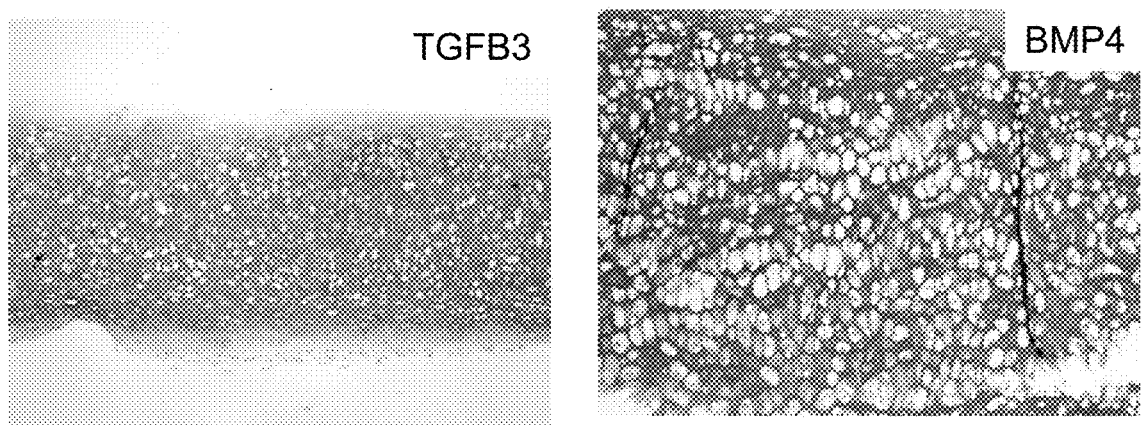
Figure 4:
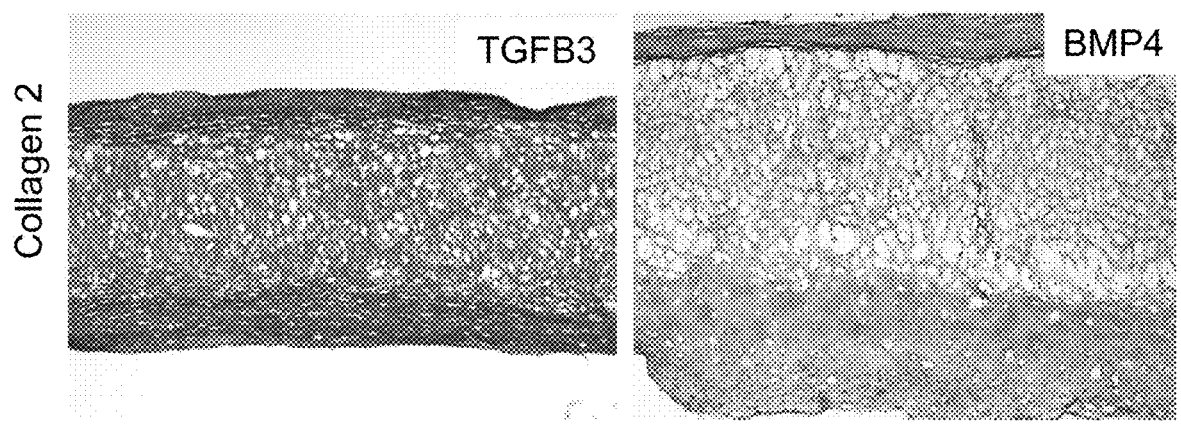
Figure 4:
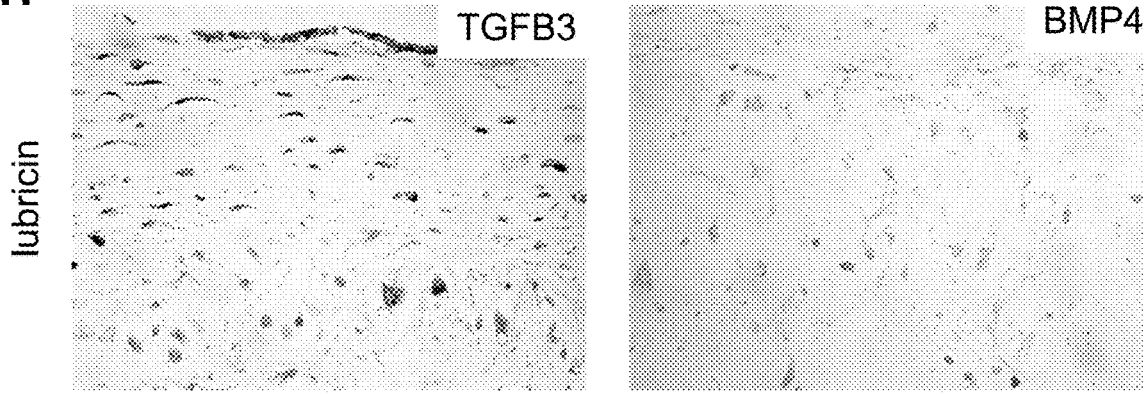
Figure 5:
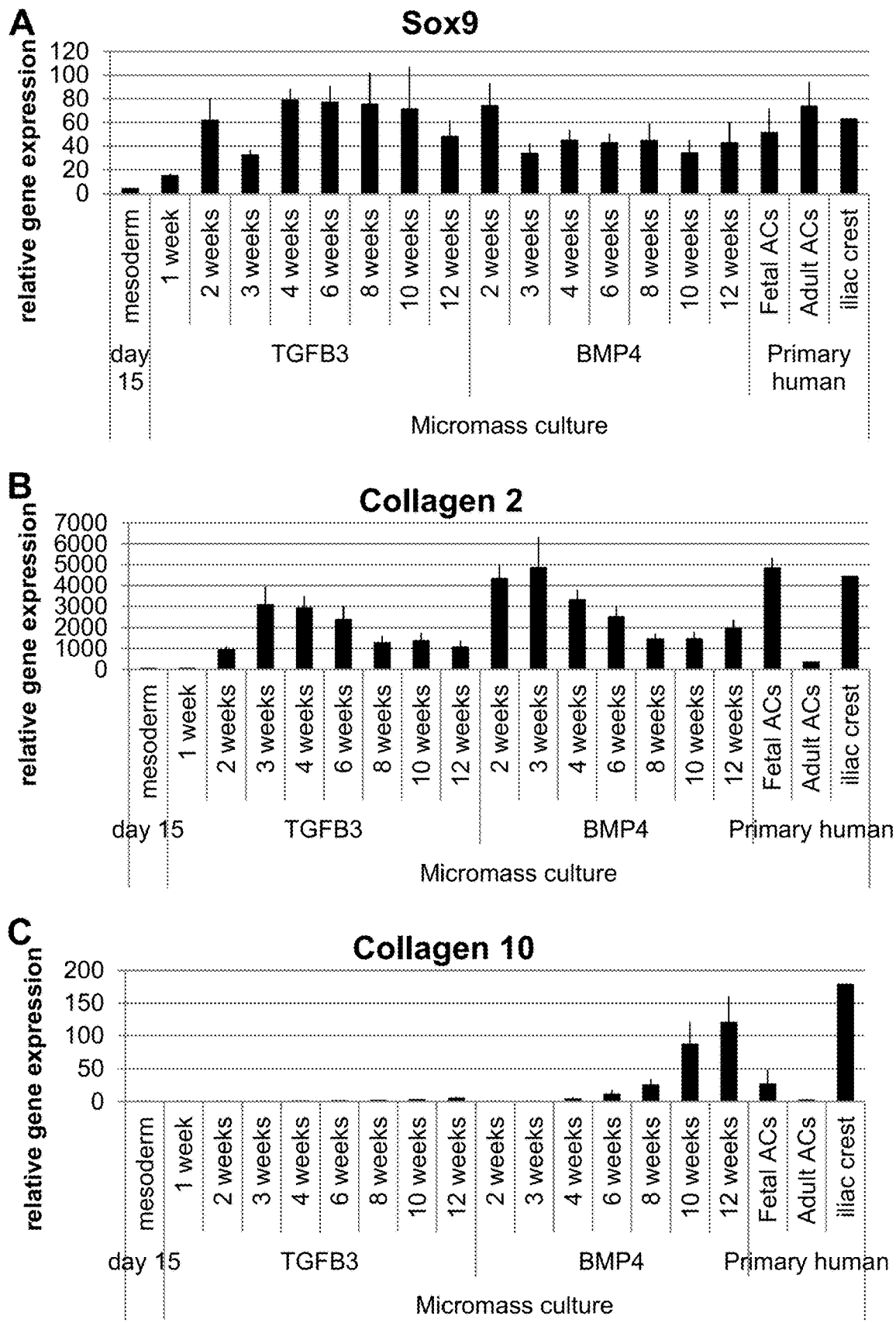
FIG. 5. Gene expression analyses of chondrocyte specification in the presence of TGFB3 or BMP4 during stages 3 and 4 of differentiation respectively. General chondrocyte genes Sox9 (A) and collagen 2 (B), hypertrophic genes collagen 10 (C), Runx2 (D), osterix (E) and alkaline phosphatase (F), articular cartilage associated genes lubricin (G) and cartilage intermediate layer protein 2 (CILP2) (H), interzone-related (joint progenitor) genes GDF5 (I), ERG (J) and Wnt9a (K). Expression is copy number relative to TBP (n=3 to 8 biological replicates) and is compared to primary fetal chondrocytes (aged 16 to 19 weeks, n=4), primary healthy adult articular chondrocytes (n=2), and growth plate-like chondrocytes isolated from the iliac crest of an adult (n=1). T15 Mesoderm indicates day 15 hESC-derived paraxial mesoderm (DM+FGF-treated). Error bars indicate s.e.m.
Figure 5:
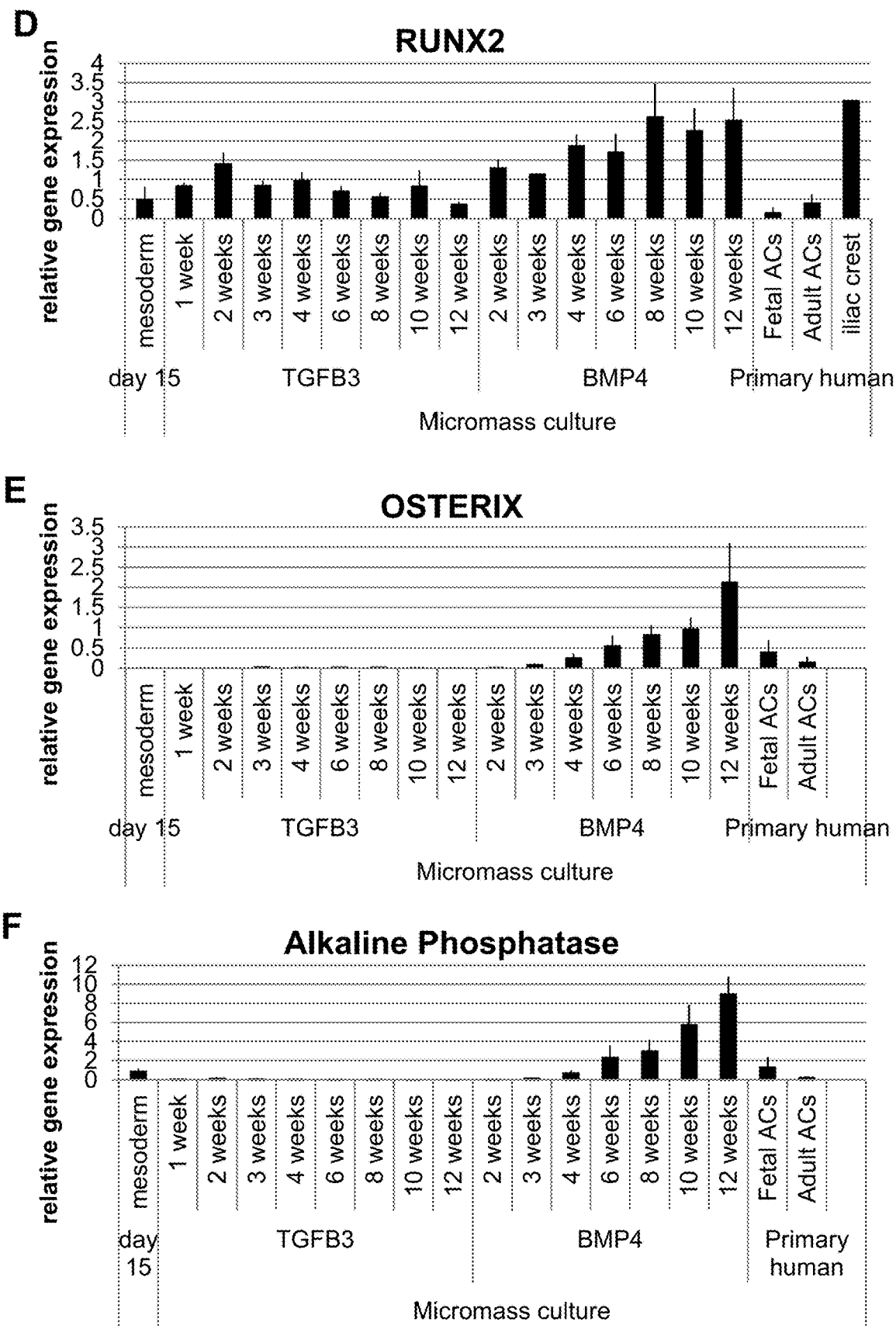
Figure 5:
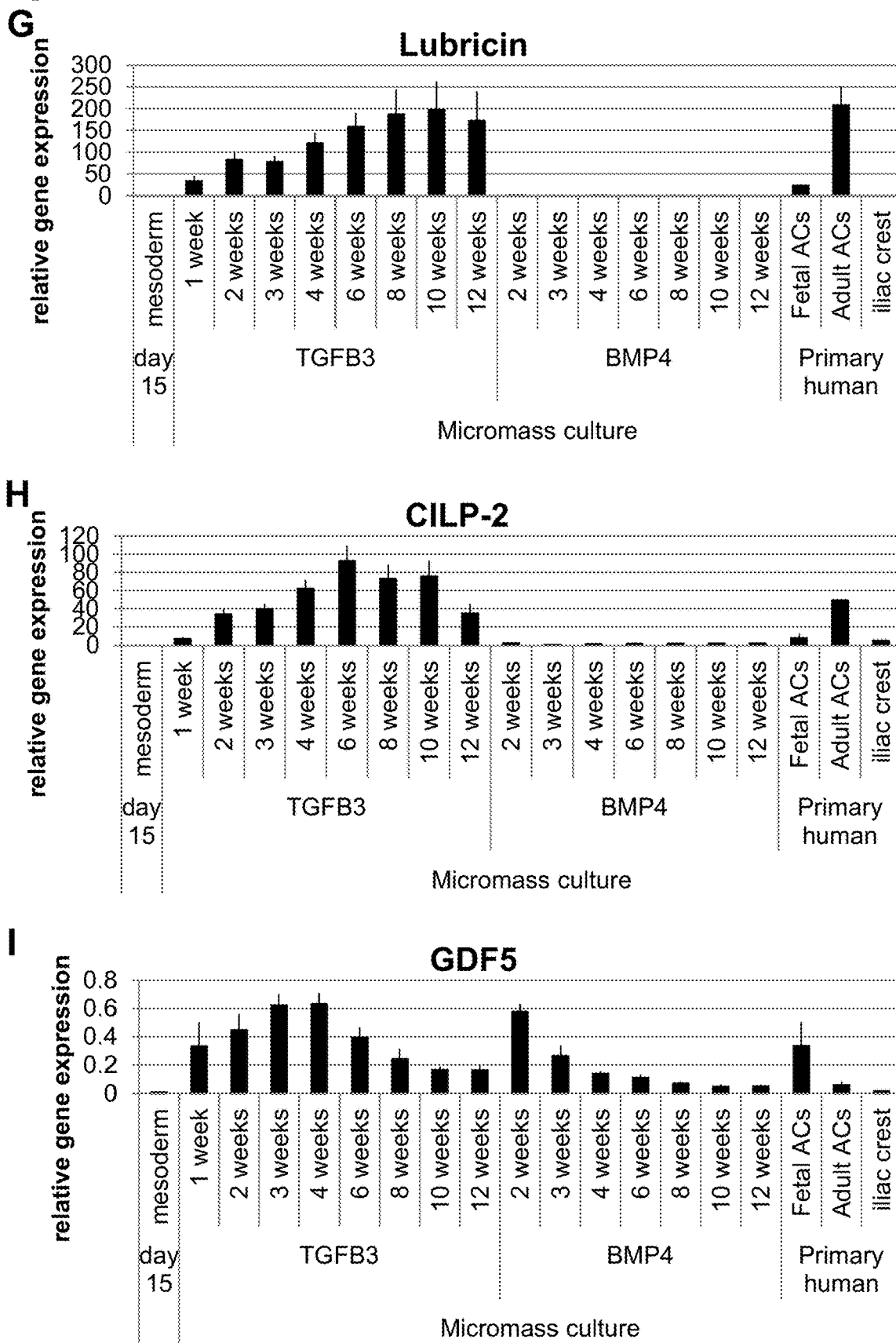
Figure 5:
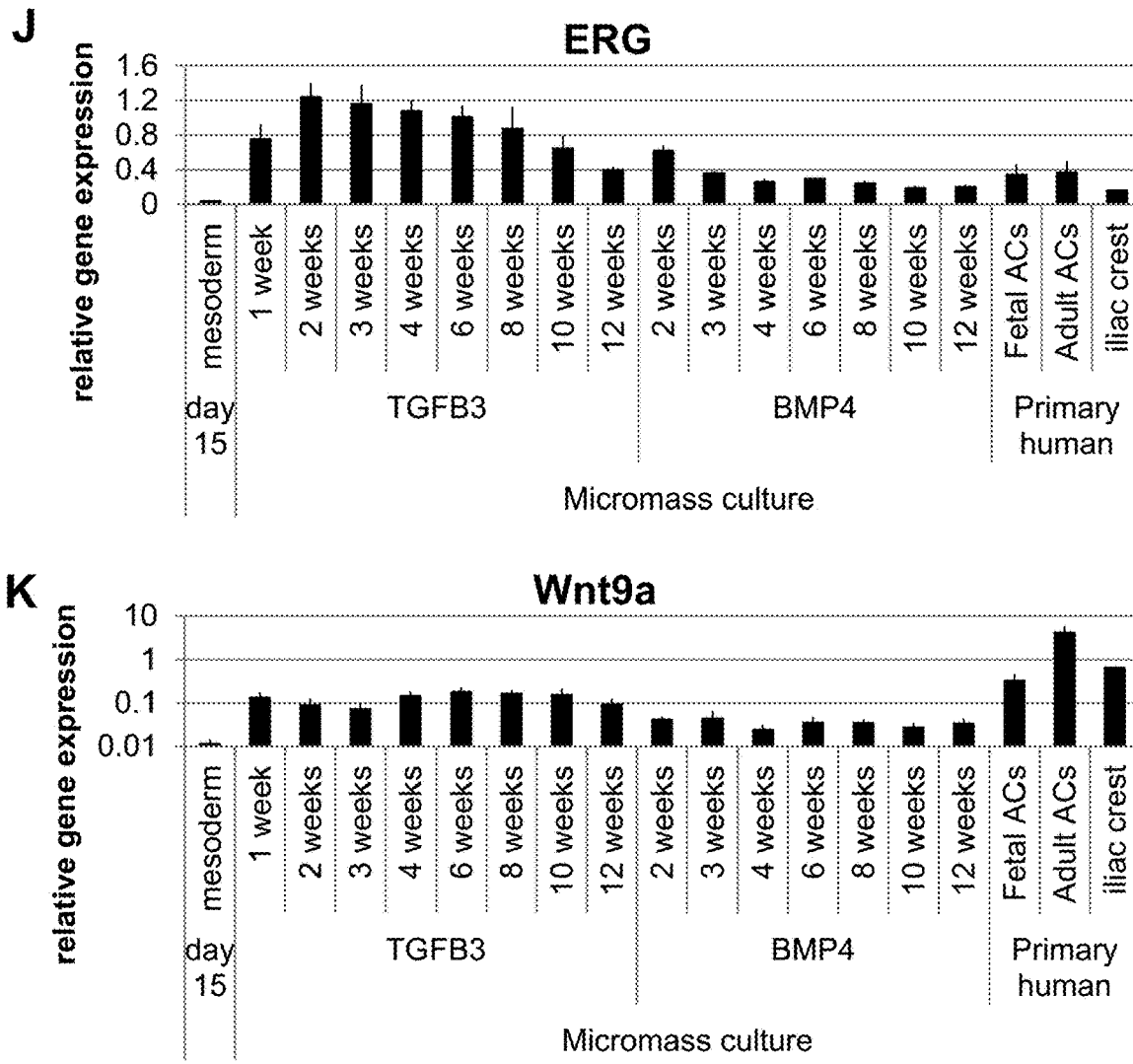

The tissue generated under the two conditions was next analyzed for gene expression patterns by qRT-PCR (FIG. 5) and for the presence of specific proteins associated with cartilage development by immunohistochemistry and immunostaining (FIG. 4). Expression of SOX9 and COL2A1, genes expressed by both articular and hypertrophic chondrocytes, was upregulated by 2 weeks of culture in both TGFbeta3- and BMP4-treated tissues (FIG. 5A-B). The levels of expression were similar to those found in primary human fetal ACs, healthy adult ACs, and iliac crest (hypertrophic) chondrocytes. Expression of genes associated with hypertrophic chondrocytes including RUNX2, SP7, alkaline phosphatase (ALP/ALPL), and COL10A1 was significantly higher in the 8- to 12-week old BMP4-treated tissue than in the tissue maintained in TGFb3 (FIG. 5C-F). The reverse pattern was observed for genes known to be expressed by superficial zone articular chondrocytes including lubricin (PRG4) and cartilage intermediate layer protein 2 (CILP2) (FIG. 5G-H), as well as for those expressed in joint interzone cells, the progenitor population of ACs, such as GDF5, WNT9A, and ERG (FIG. 1-K).

Together, the histology and gene expression analyses of hPSC-derived cartilages derived from TGFB3-treated cells and BMP4-treated cells suggest that two unique chondrocyte populations and cartilage-like tissues have been generated in-vitro. The maturation of TGFB3-treated cartilage tissues for an extended period of time (up to 12 weeks) allows for the expression of mature AC genes, such as lubricin and CILP2. Treatment of the TGFB3 cultures with BMP4 induces a hypertrophic response that is easily observed by histology and by the upregulation of genes associated with hypertrophic chondrocytes found in the growth plate, collagen 10 and Runx2. Thus, hPSC-derived cartilage tissue derived with TGFB3 treatment represents articular-like cartilage, while BMP4-treated cartilage tissue represents growth plate-like hypertrophic cartilage.

Figure 6:
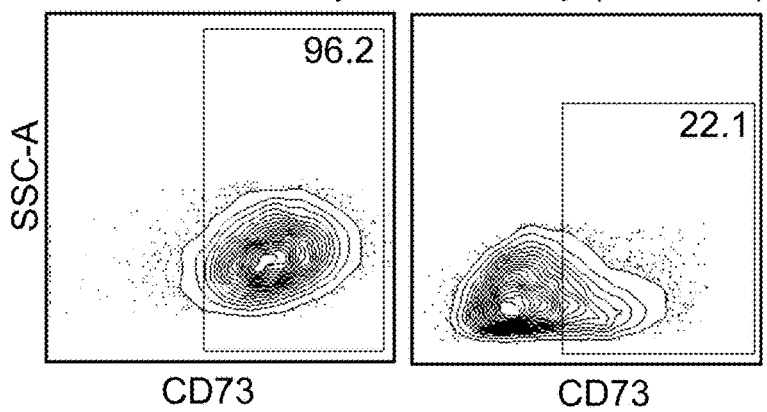
FIG. 6. CD73 is expressed by articular chondrocytes. Flow cytometric analyses of primary chondrocytes (A) Healthy adult articular chondrocytes and iliac crest GPC-like chondrocytes, (B) Primary fetal chondrocytes, primary (C) or passaged (passage (P)2, D) fetal chondrocytes after 9 to 10 weeks of micromass culture in the presence of TGFB3 or BMP4, and (E) hPSC-derived chondrocytes after 11 weeks derived in the presence of TGFB3 or BMP4. (F) Time course of CD73 and PDGFR-beta cells surface expression on T12 and T15 paraxial mesoderm populations, and micromass cultures treated with TGFB3 after 3 days, 10 days, and 2 weeks. (G) Time course of CD73 expression on TGFB3-treated micromasses after 3 days, 7 days, 10 days, and 2 to 5 weeks.
Figure 6:
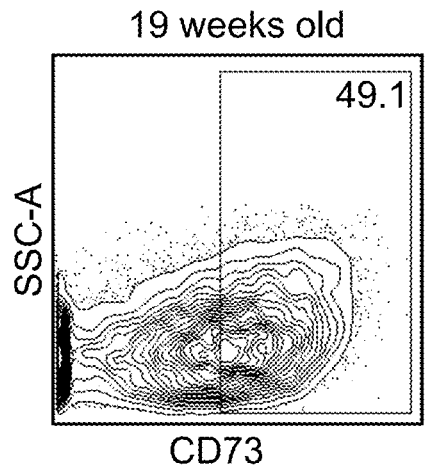
Figure 6:
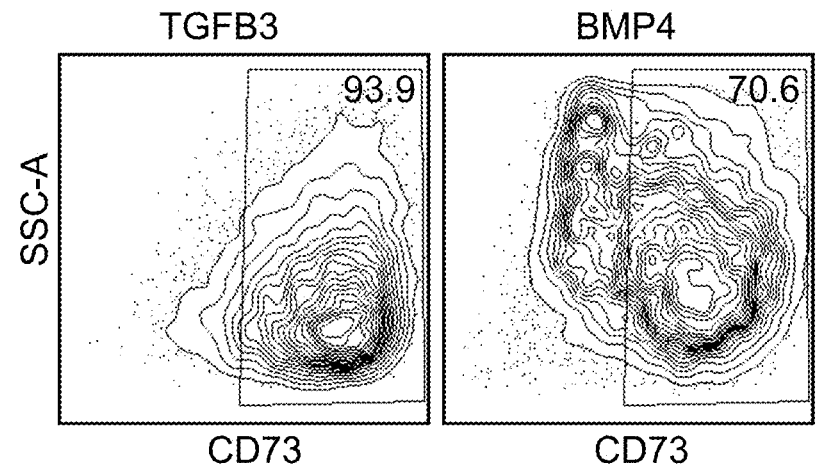
Figure 6:
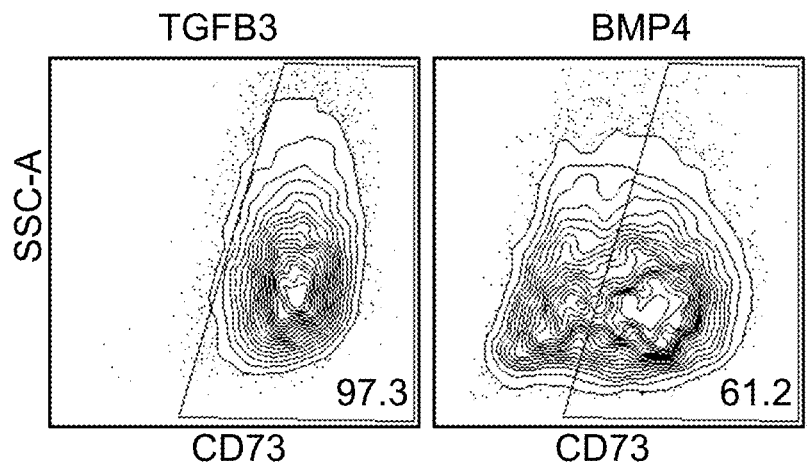
Figure 6:
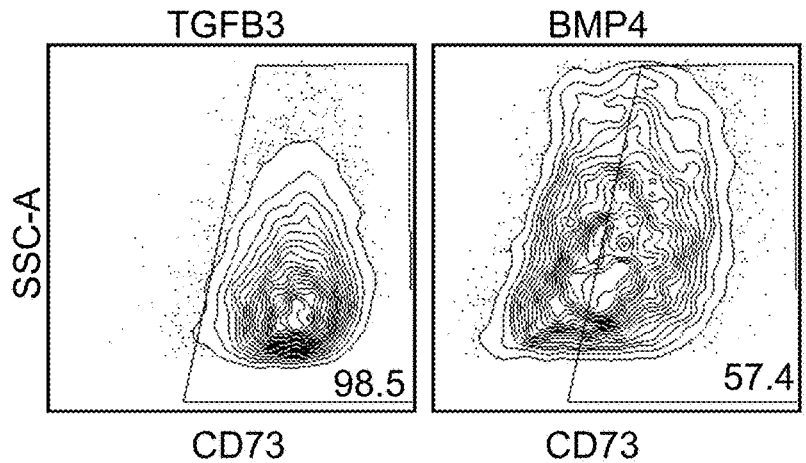
Figure 6:
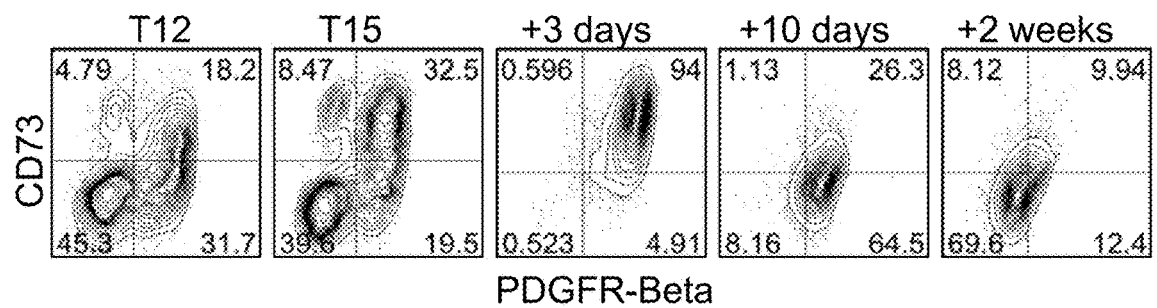
Figure 6:
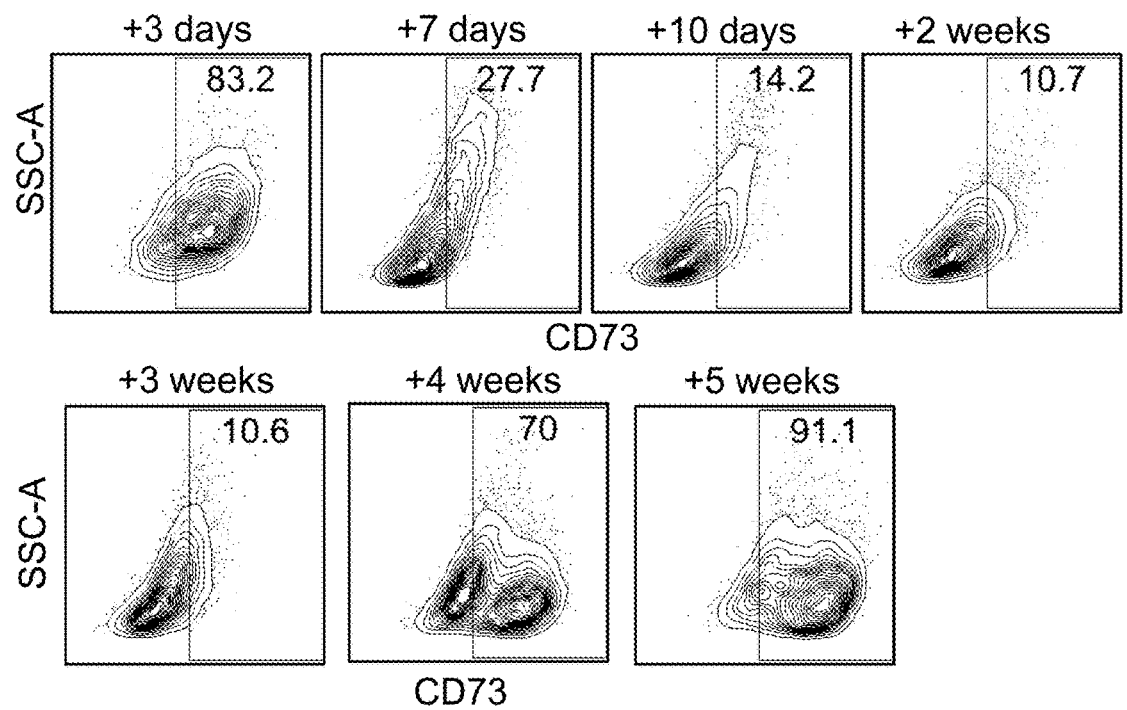

In an effort to identify cell surface markers that can be exploited for the enrichment of ACs either from hPSC differentiation cultures, or from cartilage tissue isolated from patients for the purpose of autologous chondrocyte transplantation, we performed a flow cytometry based antibody screen comprised of 350 antibodies. Several sources of primary chondrocytes from the knee joint were screened, including at least two samples of human healthy adult articular cartilage that were used for allogeneic transplantations, at least 4 human fetal chondrocytes aged 16-19 weeks of age, and 1 sample of human adult chondrocytes isolated from the iliac area in the hip area, which have growth plate characteristics. From these screens, we identified CD73 as a marker of articular chondrocytes (FIG. 6). CD73 is expressed by virtually all (>96%) of healthy adult articular chondrocytes isolated from the knee, but it is expressed by only about 22% of iliac crest GPC-like chondrocytes (FIG. 6A). CD73 is expressed by approximately half of fetal chondrocytes (FIG. 6B), which may represent an impure population of articular chondrocytes as it is difficult to isolate just these cells from the growth plate chondrocytes if the secondary ossification centre has not yet been ossified, which happens during adolescence.

Primary (P0) and passaged (P2) fetal chondrocytes can also be cultured in micromass with TGFB3 or BMP4, similar to how hPSC-derived cartilage tissues are formed. TGFB3-treated fetal P0-derived or fetal P2-derived cartilage tissues contain over 93% CD73 positive cells, while BMP4 treatment reduces the percentage of CD73+ cells to 70% and 61% respectively (FIG. 6C,D). CD73 expression is also expressed by over 98% of hPSC-derived cartilage tissues derived with TGFB3-treatment (FIG. 6E). The percentage of CD73+ cells is reduced to only about 57% of cells after BMP4-treatment. Thus, CD73 marks primary healthy adult ACs, a proportion of healthy fetal chondrocytes, fetal chondrocytes or passaged fetal chondrocytes cultured as micromasses in TGFB3, and TGFB3-treated articular chondrocyte-like cells derived from human PSCs.

It is interesting that a mesenchymal cell surface marker such as CD73 marks the hPSC-derived paraxial mesoderm early in the differentiation as well as the end-stage articular-like chondrocytes derived from that mesoderm. Paraxial mesoderm on day 12 (T12) and day 15 (T15) expresses both CD73 and PDGFR-Beta, and after the three day 'spotting' phase (day 18 total), all cells are CD73+PDGFR-Beta+ (FIG. 6F). Interestingly, both of these cell surface receptors are downregulated after 10 days to 2 weeks of micromass culture. After 4 to 5 weeks, CD73 becomes re-expressed in TGFB3-treated micromass cultures (FIG. 6G), suggesting that CD73 may become expressed when the chondrocyte progenitors are differentiating toward the articular chondrocyte fate.

Figure 7:
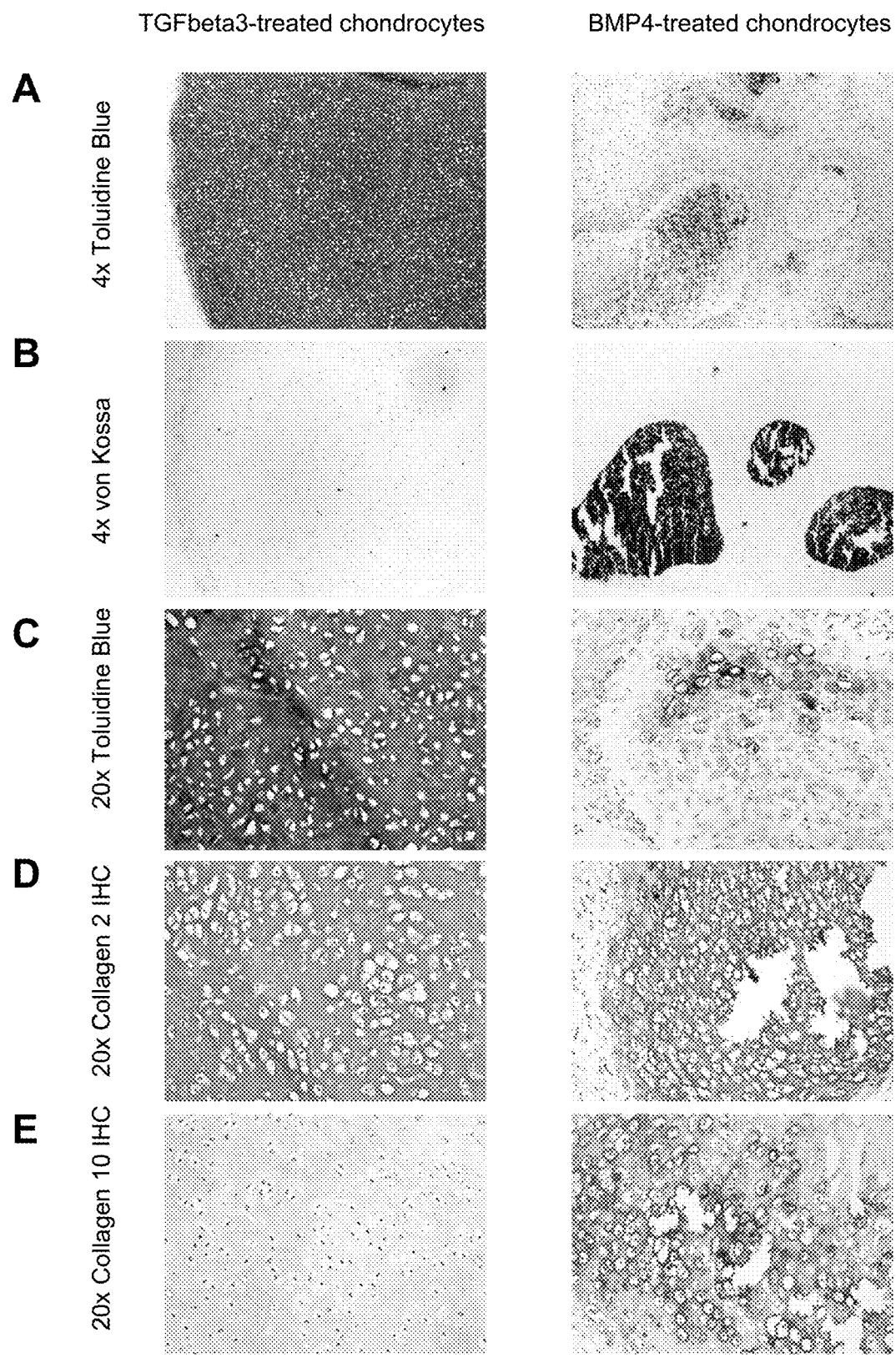
FIG. 7. hPSC-derived chondrocytes maintain respective articular or hypertrophic chondrocyte phenotypes in vivo. Micromass tissues (aged 8-12 weeks) treated with TGFβ3 or BMP4 were dissociated by collagenase treatment and chondrocytes were injected subcutaneously into immunodeficient mice for 12 weeks. Grafts were harvested and analyzed histologically after 12 weeks. Sections were stained with Toluidine blue (A, C) to indicate the presence of proteoglycans and von Kossa (B) to identify areas of mineralization. Type II (D) and type X collagen (E) was detected immunohistochemically. After 12 weeks in vivo, TGFβ3-treated chondrocyte-derived grafts stained positive for type II collagen (D) and stained metachromatically with toluidine blue (A, C), and no areas of von Kossa (B) or type X collagen positivity (E) were found. Areas of mineralization (B), von Kossa positive, black) were identified in grafts derived from BMP4-treated chondrocytes after 12 weeks, but these areas contained little proteoglycan (A, C) and stained positively for type II (D) and type X collagen (E), indicating the development of calcified cartilage.

To further characterize the potential of the two types of chondrocytes, cells from dissociated 8-12-week-old tissue were injected subcutaneously into NSG immunodeficient mice. Both populations generated proteoglycan-rich cartilage tissue that expressed type II collagen with no evidence of mineralization by 4 weeks following transplantation. Distinct differences were observed in the grafts after 12 weeks of transplantation. Tissues derived from BMP4-treated chondrocytes retained little proteoglycan (FIG. 7A, C) and contained areas of calcification/mineralization and hypertrophy as revealed by positive von Kossa (FIG. 7B) and type X collagen staining (FIG. 7E), respectively. Interestingly, grafts from the TGFbeta3-treated chondrocytes maintained a proteoglycan- (FIG. 7A, C) and type II collagen-rich ECM (FIG. 7D) with no evidence of calcification/mineralization or hypertrophy (FIG. 7 B, E). The findings from these transplantation studies demonstrate that the two chondrocyte populations are functionally distinct and provide additional evidence that the TGFbeta3-treated cells represent articular chondrocytes as they generate and maintain stable cartilage for over 12 weeks in vivo. Chondrocytes that developed in the presence of BMP4, by contrast, display characteristics of those found in the growth plate, as they gave rise to tissue that initiated endochondral ossification in vivo.

Figure 8:
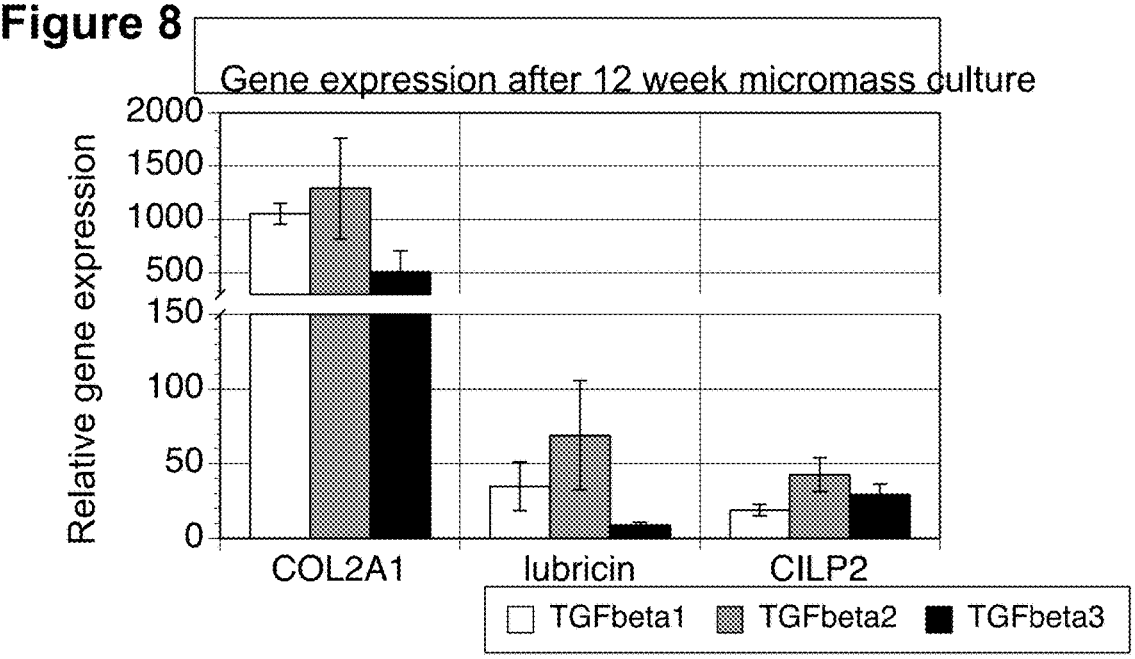
FIG. 8. TGFβ1, TGFβ2, and TGFβ3 generated articular chondrocytes from hPSC-derived paraxial mesoderm. COL2A1, lubricin, and CILP2 gene expression after 12 weeks of micromass culture in the presence of TGF agonists as indicated (10 ng/ml). Values represent copy number mRNA relative to TBP. Error bars indicate s.e.m.

COL2A1, PRG4 (lubricin) and CILP2 were also upregulated in micromass tissues treated with TGFbeta1 and TGFbeta2 for 12 weeks (FIG. 8), indicating that the generation of articular chondrocytes from hPSC-derived paraxial mesoderm response was not ligand specific.

Figure 9:
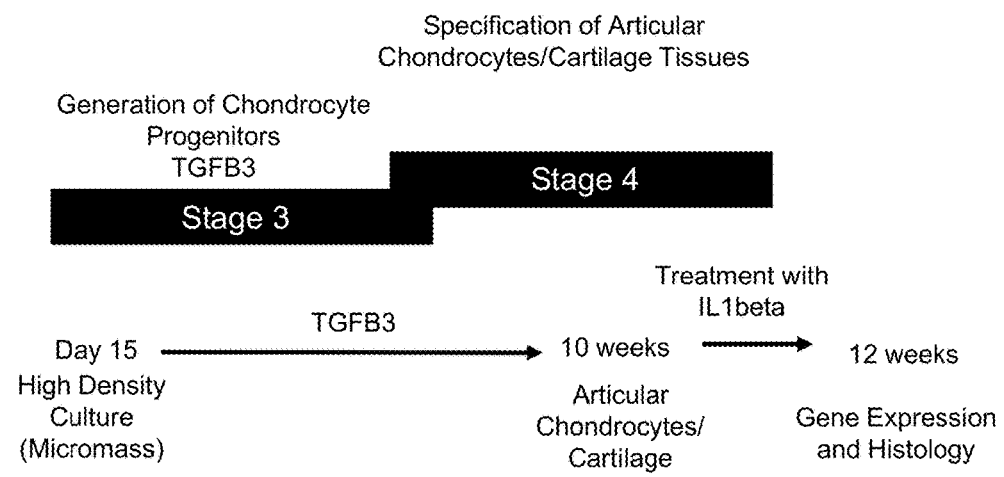
FIG. 9. hPSC-derived articular-like cartilage respond appropriately to the pro-inflammatory molecule IL1β. (A) The experimental plan is depicted. Articular cartilage tissues were derived from hPSCs for 10 weeks in the presence of TGFβ3. Cartilage tissues (micromasses) were treated for two weeks (from week 10-12) with TGFβ3 or IL1β (10 ng/ml), as indicated. Cartilage tissues were analyzed histologically or dissociated for gene expression analyses. hPSC-derived articular chondrocytes significantly upregulated the expression of MMP13 (B), MMP2 (C), ADAMTS4 (D) and ADAMTS5 (E) in response to exogenous IL1p. (F, G) Genes encoding extracellular matrix components, COL2A1 and ACAN, are significantly downregulated in response to IL1β. (H, I) Expression of superficial zone chondrocyte genes PRG4 (lubricin) and CILP2 were downregulated in presence of IL1β. (J) VEGF was upregulated in the presence of IL1β. Values represent copy number mRNA relative to TBP (n=7). Error bars indicate s.e.m. (K) Histological analysis of 12-week tissues after treatments as indicated. Metachromatic toluidine blue staining indicates proteoglycans.
Figure 9:
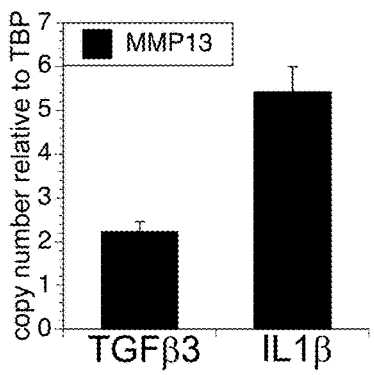
Figure 9:
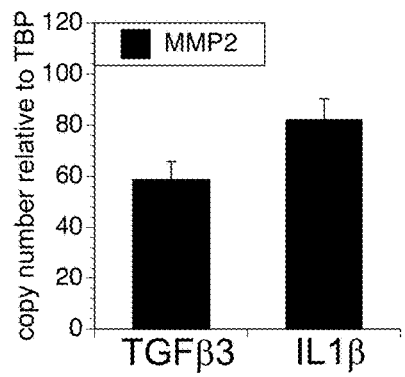
Figure 9:
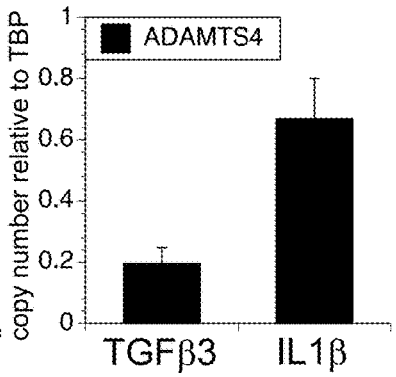
Figure 9:
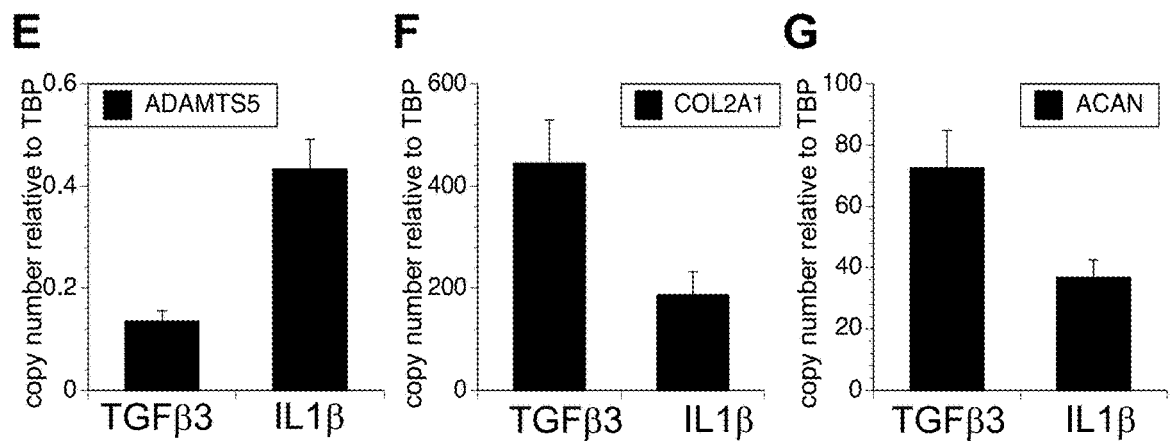
Figure 9:
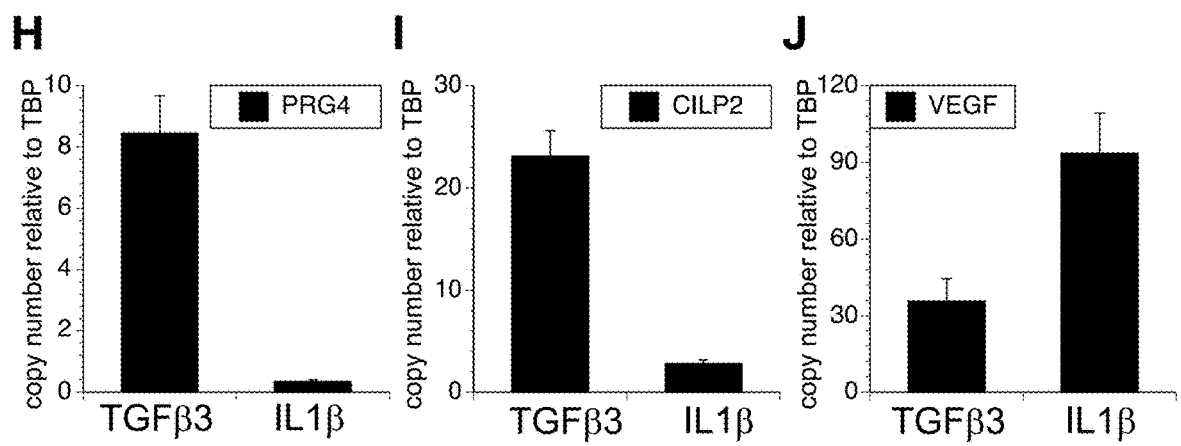
Figure 9:
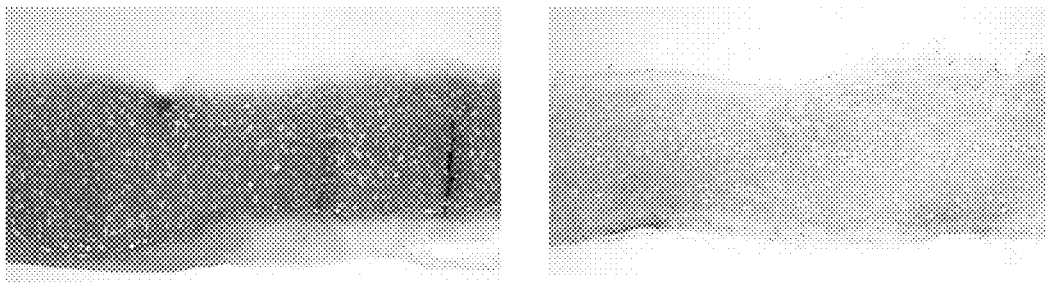

Access to an unlimited supply of hPSC-derived articular-like cartilage provides an opportunity to establish platforms to analyze the effects of pro-inflammatory cytokines such as interleukin-1α (IL1beta), known to play a role in the early stages of osteoarthritis (OA). Treatment of 10-week-old hPSC-derived ACs with IL1beta in the absence of TGFb3 for two weeks (FIG. 9A) resulted in the upregulation of expression of catabolic enzymes including matrix metallopeptidases 13 (MMP13) (FIG. 9B) and MMP2 (FIG. 9C), and ADAMTS4 & S5 (FIG. 9D,E). These enzymes cleave proteins found in cartilage extracellular matrix (ECM), such as collagens and aggrecans, which leads to the degradation of cartilage tissue. Significant upregulation of MMP13 and ADAMTS4 was observed only in the absence of TGFbeta3. ADAMTS5 was induced with or without TGFbeta3 present. The expression of lubricin (PRG4) and CILP2 was also downregulated when IL1beta was added to tissues in the absence (FIG. 9H-I) or presence of TGFbeta3. The addition of IL1beta also led to a reduction in COL2A1 and ACAN expression (FIG. 9F-G), an increase in vascular endothelial growth factor (VEGF) expression (FIG. 9J), and a noticeable loss of proteoglycans in the tissue (FIG. 9K). Together, these findings suggest that IL1beta signaling can initiate a transition from an anabolic environment to a catabolic state in the hPSC-derived ACs, similar to that observed in native cartilage during early OA pathogenesis.

Example 2

CD73+ cells represent articular non-hypertrophic chondrocytes, and the lack of CD73 positivity could identify growth plate-like hypertrophic chondrocytes.

Chondrocytes and cartilage-like tissues can be generated using a method described herein for the example the method described in Example 1. Articular chondrocyte cells can be isolated and/or separated from precursors or growth plate-like chondrocyte cells, using the CD73 cell marker. As described herein, when AC-like cells are stimulated with BMP4 they become hypertrophic and lose the expression of CD73 on their cell surface. A method of monitoring expression of the CD73 cell surface markers that can be used is the fluorescent-activated cell sorting (FACS) analysis.

Example 3

Use of hESC-Derived Chondrocytes or Cartilage for Drug Toxicology Screenings

HESC-derived chondrocytes obtained using a method described in herein for example in Example 1 could be used for predictive drug toxicology screenings as well as drug discovery. For example, the cartilage tissue and/or hypertrophic chondrocyte cells typical of growth-plate-like cartilage tissue lineages as well as their precursors can be contacted with a test substance and one or more biological endpoints measured such as cell death. For example, cell death can be measured using for example a vital cell dye exclusion assay, such as the Trypan Blue assay. For instance, AC-like chondrocytes which are exposed to a test substance (drug) can be monitored for cell toxicity after desired time-points by counting the cells that are permeable to Trypan Blue dye. Other assays include tetrazolim salt conversion assay. Examples of such assay include the MTT assay as well as the WST-1 assay. The assay can be automated for high throughput screening.

Example 4

Use of hESC-Derived Chondrocytes or Cartilage in Testing Cell Proliferation as Induced by Test Substances Another example of the use of hESC-derived chondrocytes is the testing of drugs that have an effect on cell differentiation or proliferation. Of particular interest would be the testing of drugs that can influence the proliferation of primary articular chondrocytes into articular cartilage tissue, as monitored by the use of the CD73 marker which indicates an AC-like fate. A variety of cell proliferation assays are available and can monitor response to a test substance of interest. For instance the $^3$H Thymidine incorporation assay monitors the proliferation of cells after treatment with a test substance or growth factor. Following such treatment, cells are incubated with $^3$H-thymidine for 16-24 hours. An alternative assay is a 5-bromo-2'-deoxyuridine (BrdU) incorporation assay. Yet another alternative is the use of the use of the propidium iodine test. The fluorescence is directly proportional to the DNA content in the samples. This method of monitoring cell proliferation can be particularly useful in the context of hESC-derived chondrocytes as it can be used with cells that are grown on a monolayer.

Example 5

Use of Size and Granularity of Chondrocytes as a Way to Distinguish Cell Lineage The disclosure describes methods for generating different lineages of chondrocytes, more specifically the AC-like chondrocyte as well the growth-plate like chondrocytes. These lineages can for example be distinguished based on size. For example, using the forward scatter (FSC-A) and side scatter (SSC-A) of hESC-derived chondrocytes, in the absence of an antibody based staining observed during flow cytometric analysis of live cells could be used. TGFB3 treated AC like cell population displayed as a tight population of cells with generally uniformly size and granularity, while BMP4-treated hypertrophic chondrocytes display a heterogeneous cell population that generally have larger FSC-A and SSC-A attributes. Thus, FSC-A and SSC-A attributes of live cells can be a useful readout in experiments where factors that induce or prevent chondrocyte hypertrophy are being tested.

Example 6

Monitoring of Cell Development and Cell Lineage Using Reporter Gene Assays

A reporter gene assay can be used with the methods described herein to identify factors and substances that maintain or alter the expression of chondrocyte specific genes including mature cartilage genes such as lubricin or collagen 10. For example, a lubricin promoter-RFP (red fluorescent protein) targeted hESC line could be used for screening test substances that induce lubricin promoter activity and the expression of RFP detectable by fluorescent microscopy. An increase in lubricin promoter RFP+ expression, fluorescence, or an increase in the percentage of cells that express lubricin promoter RFP+ would indicate an increase in the percentage of cells that displayed non-hypertrophic articular like chondrocyte characteristics. In contrast, a loss of lubricin promoter RFP+ may indicate a loss of these cells and/or articular chondrocyte like characteristics.

Likewise, a collagen 10 reporter (such as collagen 10 promoter-Green Fluorescent Protein-GFP) would be useful in detecting an increase or decrease in the level of collagen 10 expression in cartilage cells or tissues. An increase in collagen 10-GFP+ expression, fluorescence, or an increase in the percentage of cells that express collagen 10-GFP would indicate an increase in the percentage of cells that displayed hypertrophic chondrocyte characteristics. In contrast, a loss of collagen 10-GFP may indicate a loss of hypertrophy.

The reporter lines can also be used in flow cytometry based screens.

Alternatively, a non-hypertrophic chondrocyte cell and/or hypertrophic chondrocyte cell can be transiently or stably transfected with a reporter gene system where the reporter gene is functionally coupled to an articular chondrocyte specific promoter (i.e. articular chondrocyte reporter system), optionally a lubricin promoter element and/or a reporter gene functionally coupled to a hypertrophic chondrocyte specific promoter, optionally a collagen 10 promoter element (i.e. hypertrophic chondrocyte reporter system). The cells can be selected and then contacted with a test substance. Test substances that induce articular chondrocyte differentiation can be identified by measuring the articular chondrocyte reporter system activity (e.g. relative to a control) and test substances that induce hypertrophic chondrocyte differentiation can be identified by measuring hypertrophic chondrocyte reporter system activity (e.g. relative to a control).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirety.

CITATIONS FOR REFERENCES REFERRED TO IN THE SPECIFICATION

Akiyama, H., M. C. Chaboissier, J. F. Martin, A. Schedl and B. de Crombrugghe (2002). "The transcription factor Sox9 has essential roles in successive steps of the chondrocyte differentiation pathway and is required for expression of Sox5 and Sox6." *Genes Dev* 16(21): 2813-2828.

Archer, C. W., G. P. Dowthwaite and P. Francis-West (2003). "Development of synovial joints." *Birth Defects Res C Embryo Today* 69(2): 144-155.

Blumer, M. J., S. Longato, C. Schwarzer and H. Fritsch (2007). "Bone development in the femoral epiphysis of mice: the role of cartilage canals and the fate of resting chondrocytes." *Dev Dyn* 236(8): 2077-2088.

Burgess, R., A. Rawls, D. Brown, A. Bradley and E. N. Olson (1996). "Requirement of the paraxis gene for somite formation and musculoskeletal patterning." *Nature* 384(6609): 570-573. Bussen, M., M. Petry, K. Schuster-Gossler, M. Leitges, A. Gossler and A. Kispert (2004). "The T-box transcription factor Tbx18 maintains the separation of anterior and posterior somite compartments." *Genes Dev* 18(10): 1209-1221.

Craft, A. M., N. Ahmed, J. S. Rockel, G. S. Baht, B. A. Alman, R. A. Kandel, A. E. Grigoriadis and G. M. Keller (2013). "Specification of chondrocytes and cartilage tissues from embryonic stem cells." *Development* 140(12): 2597-2610.

Dao, D. Y., J. H. Jonason, Y. Zhang, W. Hsu, D. Chen, M. J. Hilton and R. J. O'Keefe (2012). "Cartilage-specific ss-CATENIN signaling regulates chondrocyte maturation, generation of ossification centers, and perichondrial bone formation during skeletal development." *J Bone Miner Res*.

Darabi, R., K. Gehlbach, R. M. Bachoo, S. Kamath, M. Osawa, K. E. Kamm, M. Kyba and R. C. Perlingeiro (2008). "Functional skeletal muscle regeneration from differentiating embryonic stem cells." *Nat Med* 14(2): 134-143.

Hirsinger, E., C. Jouve, J. Dubrulle and O. Pourquie (2000). "Somite formation and patterning." *Int Rev Cytol* 198: 1-65.

Hwang, N. S., M. S. Kim, S. Sampattavanich, J. H. Baek, Z. Zhang and J. Elisseeff (2006). "Effects of three-dimensional culture and growth factors on the chondrogenic differentiation of murine embryonic stem cells." *Stem Cells* 24(2): 284-291.

Hwang, N. S., S. Varghese, H. J. Lee, Z. Zhang, Z. Ye, J. Bae, L. Cheng and J. Elisseeff (2008). "In vivo commitment and functional tissue regeneration using human embryonic stem cell-derived mesenchymal cells." *Proc Natl Acad Sci USA* 105(52): 20641-20646.

Jukes, J. M., S. K. Both, A. Leusink, L. M. Sterk, C. A. van Blitterswijk and J. de Boer (2008). "Endochondral bone tissue engineering using embryonic stem cells." *Proc Natl Acad Sci USA* 105(19): 6840-6845.

Kattman, S. J., A. D. Witty, M. Gagliardi, N. C. Dubois, M. Niapour, A. Hotta, J. Ellis and G. Keller (2011). "Stage-specific optimization of activin/nodal and BMP signaling promotes cardiac differentiation of mouse and human pluripotent stem cell lines." *Cell Stem Cell* 8(2): 228-240.

Kinder, S. J., T. E. Tsang, G. A. Quinlan, A. K. Hadjantonakis, A. Nagy and P. P. Tam (1999). "The orderly allocation of mesodermal cells to the extraembryonic structures and the anteroposterior axis during gastrulation of the mouse embryo." *Development* 126(21): 4691-4701.

Koyama, E., Y. Shibukawa, M. Nagayama, H. Sugito, B. Young, T. Yuasa, T. Okabe, T. Ochiai, N. Kamiya, R. B. Rountree, D. M. Kingsley, M. Iwamoto, M. Enomoto-lwamoto and M. Pacifici (2008). "A distinct cohort of progenitor cells participates in synovial joint and articular cartilage formation during mouse limb skeletogenesis." *Dev Biol* 316(1): 62-73.

Kramer, J., C. Hegert, K. Guan, A. M. Wobus, P. K. Muller and J. Rohwedel (2000). "Embryonic stem cell-derived chondrogenic differentiation in vitro: activation by BMP-2 and BMP-4." *Mech Dev* 92(2): 193-205.

Kulesa, P. M. and S. E. Fraser (2002). "Cell dynamics during somite boundary formation revealed by time-lapse analysis." *Science* 298(5595): 991-995.

LaPrade, R. F., L. S. Bursch, E. J. Olson, V. Havlas and C. S. Carlson (2008). "Histologic and immunohistochemical characteristics of failed articular cartilage resurfacing procedures for osteochondritis of the knee: a case series." *Am J Sports Med* 36(2): 360-368.

Lawrence, R. C., D. T. Felson, C. G. Helmick, L. M. Arnold, H. Choi, R. A. Deyo, S. Gabriel, R. Hirsch, M. C. Hochberg, G. G. Hunder, J. M. Jordan, J. N. Katz, H. M. Kremers and F. Wolfe (2008). "Estimates of the prevalence of arthritis and other rheumatic conditions in the United States. Part II." *Arthritis Rheum* 58(1): 26-35.

Lawson, K. A., J. J. Meneses and R. A. Pedersen (1991). "Clonal analysis of epiblast fate during germ layer formation in the mouse embryo." *Development* 113(3): 891-911.

Mankoo, B. S., S. Skuntz, I. Harrigan, E. Grigorieva, A. Candia, C. V. Wright, H. Arnheiter and V. Pachnis (2003). "The concerted action of Meox homeobox genes is required upstream of genetic pathways essential for the formation, patterning and differentiation of somites." *Development* 130(19): 4655-4664.

Murakami, S., G. Balmes, S. McKinney, Z. Zhang, D. Givol and B. de Crombrugghe (2004). "Constitutive activation of MEK1 in chondrocytes causes Stat1-independent achondroplasia-like dwarfism and rescues the Fgfr3-deficient mouse phenotype." *Genes Dev* 18(3): 290-305.

Nakayama, N., D. Duryea, R. Manoukian, G. Chow and C. Y. Han (2003). "Macroscopic cartilage formation with embryonic stem-cell-derived mesodermal progenitor cells." *J Cell Sci* 116(Pt 10): 2015-2028.

Nostro, M. C., X. Cheng, G. M. Keller and P. Gadue (2008). "Wnt, activin, and BMP signaling regulate distinct stages in the developmental pathway from embryonic stem cells to blood." *Cell Stem Cell* 2(1): 60-71.

Oldershaw, R. A., M. A. Baxter, E. T. Lowe, N. Bates, L. M. Grady, F. Soncin, D. R. Brison, T. E. Hardingham and S. J. Kimber (2010). "Directed differentiation of human embryonic stem cells toward chondrocytes." *Nat Biotechnol* 28(11): 1187-1194.

Pacifici, M., E. Koyama, Y. Shibukawa, C. Wu, Y. Tamamura, M. Enomoto-lwamoto and M. Iwamoto (2006). "Cellular and molecular mechanisms of synovial joint and articular cartilage formation." *Ann N Y Acad Sci* 1068: 74-86.

Pelttari, K., E. Steck and W. Richter (2008). "The use of mesenchymal stem cells for chondrogenesis." *Injury* 39 Suppl 1: S58-65.

Pelttari, K., A. Winter, E. Steck, K. Goetzke, T. Hennig, B. G. Ochs, T. Aigner and W. Richter (2006). "Premature induction of hypertrophy during in vitro chondrogenesis of human mesenchymal stem cells correlates with calcification and vascular invasion after ectopic transplantation in SCID mice." *Arthritis Rheum* 54(10): 3254-3266.

Singh, M. K., M. Petry, B. Haenig, B. Lescher, M. Leitges and A. Kispert (2005). "The T-box transcription factor Tbx15 is required for skeletal development." *Mech Dev* 122(2): 131-144.

Steinert, A. F., S. C. Ghivizzani, A. Rethwilm, R. S. Tuan, C. H. Evans and U. Noth (2007). "Major biological obstacles for persistent cell-based regeneration of articular cartilage." *Arthritis Res Ther* 9(3): 213.

Tam, P. P. and S. S. Tan (1992). "The somitogenetic potential of cells in the primitive streak and the tail bud of the organogenesis-stage mouse embryo." *Development* 115(3): 703-715.

Tanaka, M., V. Jokubaitis, C. Wood, Y. Wang, N. Brouard, M. Pera, M. Hearn, P. Simmons and N. Nakayama (2009). "BMP inhibition stimulates WNT-dependent generation of chondrogenic mesoderm from embryonic stem cells." *Stem Cell Res* 3(2-3): 126-141.

Tins, B. J., I. W. McCall, T. Takahashi, V. Cassar-Pullicino, S. Roberts, B. Ashton and J. Richardson (2005). "Autologous chondrocyte implantation in knee joint: MR imaging and histologic features at 1-year follow-up." *Radiology* 234(2): 501-508.

Umeda, K., J. Zhao, P. Simmons, E. Stanley, A. Elefanty and N. Nakayama (2012). "Human chondrogenic paraxial mesoderm, directed specification and prospective isolation from pluripotent stem cells." *Sci Rep* 2: 455.

Yamashita, A., R. Krawetz and D. E. Rancourt (2008). "Loss of discordant cells during micromass differentiation of embryonic stem cells into the chondrocyte lineage." *Cell Death Differ*. zur Nieden, N. I., G. Kempka, D. E. Rancourt and H. J. Ahr (2005). "Induction of chondro-, osteo- and adipogenesis in embryonic stem cells by bone morphogenetic protein-2: effect of cofactors on differentiating lineages." *BMC Dev Biol* 5: 1.

The invention claimed is:

1. A method for generating hypertrophic chondrocyte-like cells, cartilage-like tissue, cartilage, or a combination thereof, the method comprising:
   a. culturing a $CD56^+$ and $PDGFRalpha^+$ primitive streak-like mesoderm population with a paraxial mesoderm specifying cocktail comprising:

i. an FGF agonist; and
ii. an BMP inhibitor to generate a CD73$^+$CD104$^+$, or CD73$^+$PDGFRbeta$^+$, or CD73$^+$CD105$^+$ PDGFRbeta$^+$ paraxial mesoderm population;
b. culturing the paraxial mesoderm population at a high cell density with a TGFbeta agonist to produce a high cell density, Sox9$^+$, collagen 2$^+$, chondrocyte precursor population; and
c. further culturing the high cell density, Sox9$^+$, collagen 2$^+$ chondrocyte precursor population with a BMP4 agonist for an extended period of time to produce a hypertrophic chondrocyte-like cell population or cartilage-like tissue, cartilage, or a combination thereof.

2. The method of claim 1, wherein the CD56$^+$ and PDGFRalpha$^+$ primitive streak-like mesoderm population is derived from a human embryonic stem cell population (hESC) or a human induced pluripotent stem cell population (iPSC).

3. The method of claim 1, wherein the FGF agonist is selected from the group consisting of FGF2, FGF4, FGF9, FGF19, FGF21, FGF3, FGF5, FGF6, FGF8a, FGF16, FGF17, FGF18, FGF20 and FGF23.

4. The method of claim 1, wherein the BMP inhibitor is selected from the group consisting of Chordin, soluble BMPR1a, soluble BMPR1b, Noggin, LDN-193189, and Dorsomorphin.

5. The method of claim 1, wherein the paraxial mesoderm specifying cocktail further comprises a Wnt inhibitor.

6. The method of claim 5, wherein the Wnt inhibitor is selected from the group consisting of DKK1, IWP2, and XAV939.

7. The method of claim 1, wherein the paraxial mesoderm specifying cocktail further comprises a TGFbeta inhibitor.

8. The method of claim 7, wherein the TGFbeta inhibitor is SB431524.

9. The method of claim 1 wherein the paraxial mesoderm population is comprised in embryoid bodies, monolayer culture and/or a combination thereof.

10. The method of claim 1, wherein the paraxial mesoderm population also expresses transcription factors Meox1 and Nkx3.2 and is negative for Nkx2.5.

11. The method of claim 1, wherein the Sox9$^+$, collagen 2$^+$ chondrocyte precursor population is further cultured with the TGFbeta agonist until lubricin, cartilage intermediate layer protein 2 (CILP2), or both are expressed.

12. The method of claim 1, wherein the further culturing the high cell density, Sox9+, collagen 2$^+$ chondrocyte precursor population with the TGFbeta agonist is performed in serum free media.

13. The method of claim 1, further comprising administering the hypertrophic chondrocyte-cells to a subject.

14. The method of claim 1, further comprising administering the hypertrophic cartilage-like tissue to a subject.

15. The method of claim 1, further comprising administering the hypertrophic cartilage to a subject.

16. The method of claim 13, wherein the subject has osteoarthritis, osteochondritis dissecans, polychondritis, other chondropathies, or joint injuries affecting the cartilage, to ameliorate symptoms and/or treat osteoarthritis, osteochondritis dissecans, polychondritis, other chondropathies, or joint injuries affecting the cartilage.

17. The method of claim 14, wherein the subject has osteoarthritis, osteochondritis dissecans, polychondritis, other chondropathies, or joint injuries affecting the cartilage, to ameliorate symptoms and/or treat osteoarthritis, osteochondritis dissecans, polychondritis, other chondropathies, or joint injuries affecting the cartilage.

18. The method of claim 15, wherein the subject has osteoarthritis, osteochondritis dissecans, polychondritis, other chondropathies, or joint injuries affecting the cartilage, to ameliorate symptoms and/or treat osteoarthritis, osteochondritis dissecans, polychondritis, other chondropathies, or joint injuries affecting the cartilage.

19. A method of testing candidate chondrogenic modulating substances selected from the group consisting of a factor isolated from a subject with diseased cartilage or bone, a factor isolated from a fat pad in a joint of a subject with arthritis, a factor isolated from a fat pad in a joint of an obese subject, and a factor isolated from a fat pad in a joint of a healthy subject, the method comprising:
a. carrying out the method of claim 1, wherein said test substance is included in any one, or more, of the culture steps of the method of claim 1;
b. assessing the effect of the test substance on chondrocyte proliferation, maintenance and/or differentiation compared to a control population generated in the absence of test substance; and
c. identifying the test substance as a candidate chondrogenic modulating substance if the test substance increases or decreases proliferation, and/or affects chondrocyte maintenance or differentiation compared to the control.

* * * * *